US008940271B2

(12) United States Patent
Heit et al.

(10) Patent No.: US 8,940,271 B2
(45) Date of Patent: *Jan. 27, 2015

(54) TRANSMUCOSAL ADMINISTRATION OF DRUG COMPOSITIONS FOR TREATING AND PREVENTING DISORDERS IN ANIMALS

(75) Inventors: Mark C. Heit, Lansdale, PA (US); Antonio M. Benitz, Portage, MI (US); Dennis F. Steadman, Yardley, PA (US); David M. Petrick, Princeton, NJ (US)

(73) Assignee: Abbott Laboratories, Abbott Park, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/327,028

(22) Filed: Dec. 15, 2011

(65) Prior Publication Data
US 2012/0289470 A1 Nov. 15, 2012

Related U.S. Application Data

(63) Continuation of application No. 11/356,451, filed on Feb. 17, 2006, now Pat. No. 8,097,614.

(60) Provisional application No. 60/664,183, filed on Mar. 23, 2005, provisional application No. 60/653,964, (Continued)

(51) Int. Cl.
*A61K 31/4178* (2006.01)
*A61K 9/00* (2006.01)
(Continued)

(52) U.S. Cl.
CPC ............ *A61K 31/4178* (2013.01); *A61K 9/006* (2013.01); *A61K 9/12* (2013.01); *A61K 31/704* (2013.01); *A61K 31/7048* (2013.01); *A61K 38/13* (2013.01)
USPC ............ 424/1.13; 424/45; 424/434; 424/435; 128/200.14; 128/200.23; 514/226.5; 514/371; 544/49; 544/52; 548/146; 548/190; 548/195

(58) Field of Classification Search
CPC ..... A61K 9/006; A61K 9/12; A61K 31/4178; A61K 31/7048; A61K 38/13
USPC ............ 424/1.13, 45, 434, 435; 128/200.14, 128/200.23; D09/448, 682, 686; 514/226.5, 514/371; 544/49, 52; 548/146, 190, 195
See application file for complete search history.

(56) References Cited

U.S. PATENT DOCUMENTS 3,666,182 A * 5/1972 Cureton ................. 239/327
4,232,002 A 11/1980 Nogrady
(Continued)

FOREIGN PATENT DOCUMENTS

DE 3338978 A1 5/1984
DE 3544692 A1 6/1987
(Continued)

OTHER PUBLICATIONS

A. Shojaei, "Buccal Mucosa As a Route for Systemic Drug Delivery7: A Review," 1998; J. Pharm. Pharmaceut. Sci.; 1(1): 15-30.*
(Continued)

*Primary Examiner* — Jane C Oswecki
(74) *Attorney, Agent, or Firm* — Whyte Hirschboeck Dudek S.C.

(57) ABSTRACT

The invention includes compositions for transmucosal administration to an animal comprising at least one active agent and a pharmaceutically acceptable carrier. A preferred active agent is selected from the group consisting of meloxicam, carprofen, enrofloxacin, clemastine, diphenhydramine, digoxin, levothyroxine, cyclosporine, ondansetron, lysine, zolpidem, propofol, nitenpyram, ivermectin, milbemycin, and pharmaceutically acceptable salts, solvates and esters thereof. In another embodiment, the invention includes methods of treating or preventing a condition in an animal comprising transmucosally administering a composition comprising a therapeutically or prophylactically effective amount of an active agent and a pharmaceutically acceptable carrier.

18 Claims, 45 Drawing Sheets

Mean (± SD) plasma concentrations of meloxicam following administration via transmucosal oral mist and oral suspension at 0.2 mg/kg in dogs.

Related U.S. Application Data filed on Feb. 17, 2005, provisional application No. 60/661,920, filed on Mar. 16, 2005, provisional application No. 60/664,939, filed on Mar. 25, 2005, provisional application No. 60/665,525, filed on Mar. 28, 2005, provisional application No. 60/664,181, filed on Mar. 23, 2005, provisional application No. 60/664,938, filed on Mar. 25, 2005, provisional application No. 60/669,888, filed on Apr. 11, 2005, provisional application No. 60/670,651, filed on Apr. 13, 2005, provisional application No. 60/693,942, filed on Jun. 27, 2005.

(51) Int. Cl.
*A61K 9/12* (2006.01)
*A61K 31/704* (2006.01)
*A61K 31/7048* (2006.01)
*A61K 38/13* (2006.01)

(56) References Cited

U.S. PATENT DOCUMENTS

| | | | |
|---|---|---|---|
| 4,857,312 A | | 8/1989 | Hegasy et al. |
| 4,919,919 A | | 4/1990 | Aouda et al. |
| 5,047,230 A | * | 9/1991 | Nagy et al. ............... 424/45 |
| 5,370,862 A | * | 12/1994 | Klokkers-Bethke et al. ... 424/47 |
| 5,407,663 A | | 4/1995 | Eisen |
| 5,869,082 A | | 2/1999 | Dugger, III |
| 5,955,098 A | | 9/1999 | Dugger, III |
| 6,110,486 A | | 8/2000 | Dugger, III |
| 6,184,220 B1 | | 2/2001 | Turck et al. |
| 6,610,711 B2 | | 8/2003 | Armer |
| 8,097,614 B2 | | 1/2012 | Heit et al. |
| 2002/0035107 A1 | | 3/2002 | Henke et al. |
| 2004/0204413 A1 | * | 10/2004 | Faour et al. .............. 514/248 |
| 2004/0229038 A1 | * | 11/2004 | Cooper et al. ......... 428/402.21 |
| 2005/0025715 A1 | | 2/2005 | Duggger, III |
| 2006/0239928 A1 | | 10/2006 | Heit et al. |

FOREIGN PATENT DOCUMENTS

| | | |
|---|---|---|
| DE | 3922650 A1 | 1/1990 |
| EP | 0391342 A1 | 10/1990 |
| EP | 0557129 A1 | 8/1993 |
| EP | 1064964 A2 | 1/2001 |
| EP | 1 275 374 A1 | 1/2003 |
| GB | 2285921 A | 8/1995 |
| GB | 2 291 593 A | 1/1996 |
| JP | 8-169829 A | 7/1996 |
| JP | 2003-535902 A | 12/2003 |
| WO | WO 91/16929 A1 | 11/1991 |
| WO | WO 94/13280 A1 | 6/1994 |
| WO | WO 97/01329 A1 | 1/1997 |
| WO | WO 97/29735 A1 | 8/1997 |
| WO | WO 99/32081 | 7/1999 |
| WO | 01/85245 A1 | 11/2001 |
| WO | 01/97813 A2 | 12/2001 |
| WO | WO 03/049733 A1 | 6/2003 |
| WO | 03/061704 A2 | 7/2003 |
| WO | WO 2004/016244 A2 | 2/2004 |
| WO | 2004/019903 A1 | 3/2004 |
| WO | WO2004/019903 A1 * | 3/2004 |
| WO | WO2004019903 A1 * | 3/2004 |
| WO | WO 2004/041271 A1 | 5/2004 |
| WO | 2004/056394 A1 | 7/2004 |
| WO | WO 2004/080382 A2 | 9/2004 |

OTHER PUBLICATIONS

Streisand et al., "Buccal Absorption of Fentanyl Is pH-dependent in Dogs," 1995; Anesthesiology, 82:759-764.*
"Acid", Merriam-Webster Online Dictionary, [retrieved May 31, 2013] Retrieved from the Internet: <URL: http://www.merriam-webster.com/dictionary/acid>.*
A. Shojaei, "Buccal Mucosa As A Route for Systemic Drug Delivery7: A Review," 1998; J. Pharm. Pharmaceut. Sci.; 1(1):15-30.*
Striesand et al., "Buccal Absorption of Fentanyl is pH-dependent in Dogs," 1995; Anesthesiology, 82:759-764.*
"Supplementary European Search Report," 7 pages, EP appl. No. 06735301.1 (mailed Jun. 25, 2012).
Bergvall, "Clinical efficacy of milbemycin oxime in the treatment of canine scabies: a study of 56 cases," Jpn. J. Vet. Dermatol. 9(4):270-272 (2000).
Chen, F.-C. and Li, W.-H., "Genomic Divergences between Humans and Other Hominids and the Effective Population Size of the Common Ancestor of Humans and Chimpanzees," Am. J. Hum. Genet. 2001, 68, pp. 444-456.
Fukash et al., "Anthelmintic Efficacy of Milbemycin D against *Toxocava canis* and *Ancylostovica caninum* in Dogs," J. Vet. Med. 45(10):775-782 (1982).
International Search Report for PCT/US06/05575; 2 pages (mailed Apr. 10, 2007).
Kamada et al., "Studies on Safety of Nitroglycerin Spray (RJ0019) (Report II)—Oral Mucosal Irritation and Effects on the Whole Body by Repeated Administration for 30 Days," Clin. Report 24(10):5303-5320 (1990).
Kondo et al., "Effects of cyclodextrin derivatives on sytemic absorption of morphine through nasal cavity and entry into central nervous system in rats," Drug Deliv. System 11(2):99-104 (1996).
Muragugi et al., "Clinical efficacy of enrofloxacin in dogs and cats," J. Vet. Med. 48(10):801-806 (1995).
Nozaki et al., "Studies on the Metabolic Fate of TYB-3215: Absorption, Distribution and Excretion after Application to the gingiva of Dogs," Pharmacokinet. 6(2):191-199 (1991) Abstract.
Okumura et al., "Pharmacokinetic Analysis of Plasma Concentration after Oral Administration of Clemastine Funarate in Dogs," Jpn. Pharmacol. Ther. Med. Treatment 13(10):5605-5615 (1985).
Stalker and Pollock, "Bioavailability of Flurbiprofen Following Buccal Administration," Pharm Res. 8(5):605-607 (1991).
Unknown Author and Title, Jpn. J. Clin. Pharmacol. Ther. 30(1):247-248 (1999).
Accili, et al., European Jornal of Pharmaceutical Sciences, 2004, 22, pp. 225-234.
Barrera, et al., "Ehlers-Danlos syndrome in a dog," Can. Vet. J., Apr. 2004, 45, pp. 355-356.
Braga, et al., "Making Cyrstals from Crystals: a green route to crystal engineering and polymorphism,", Chem. Commun., 2005, pp. 3635-3645.
Brooks, M., "A Review of Canine Inherited Bleeding Disorders: Biochemical and Molecular Strategies for Disease Characterization and Carrier Detection," The Jornal of Heredity, 1999, 90(1), pp. 112-118.
Dali, et al., "A Rabbit Model for Sublingual Drug Delivery: Comparison with Human Pharmacokinetic Studies of Propranolol, Verapamil, and Captopril," Journal of Pharmaceutical Sciences, Jan. 2006, 95(1), pp. 37-44, published online on Nov. 23, 2005.
Fries, C.L. and Remedios, A.M., "The pathogenesis and diagnosis of canine hip dysplasia: A review," Can. Vet. J., Aug. 1995, 36, pp. 494-502.
Junginger, et al., "Recent advances in buccal drug delivery and absorption-in vitro and in vivo studies," J. Controlled Release, 1999, vol. 62, pp. 149-159.
The Merck Index, 11*th* Edition, published in 1989, by Merck & Co., Inc., see p. 366, citation No. 2345, "Clemastine", 2 pages.
Myz, et al., "Synthesis of co-crystals of meloxicam with carboxylic acids by grinding," Mendeleev Commun. 2009, 19, p. 272-274.
Peleg, A., et al., "*Acinetrobacter baumannii*: Emergence of a Successful Pathogen," Clinical Microbiology Reviews, Jul. 2008, 21(3), pp. 538-540, 549-550, and 568-582.
Sandri, et al., "Buccal penetration enhancement properties . . . " International Journal of Pharmaceutics, 2005, 297, pp. 146-155.
Seddon, K.R., "Pseudopolymorph: a polemic," Crystal Growth & Design, 2004, 4(6), pp. 1087, web release date Oct. 19, 2004.
Shojaei, A. H., "Buccal Mucosa as a Route for Systemic Drug Delivery: A Review," J. Pharm. Pharmaceut. Sci., 1998, 1(1), pp. 15-30.
Streisand, et al., "Buccal Absorption of Fentanyl is pH-Dependent in Dogs," Anesthesiology, 1995, 82, pp. 759-764.

(56) References Cited

OTHER PUBLICATIONS

Tiwari, et al., AAPS Pharmsci. 1999, 1(3), article 13, published online at www.pharmscie.org-accessed on Nov. 22, 2010.

Vippagunta, et al., "Crystalline Solids", Advanced Drug Delivery Reviews, 2001, 48, 3-26.

Volund, A., "Conversion of insulin units to SI units," American Journal of Clinical Nutrition, 1993 Nove., 58(5), pp. 714-715.

Xu, et al., "Hypoglycemic Effect of a Novel Insulin Buccal Formulation on Rabbits," Pharmacological Research, 2002, 46(5), pp. 459-467.

Cesar et al., "Correlation of Microenvironmental Drug Concentration With Inhibition of Growth of Microorganisms on Surfaces." Antimicrob. Agents Chemother. 24(6):941-946 (1983).

Declaration submitted by Applicant to the examining division, in opposition to EP appl. No. 97914779.0 (2004).

Declaration of Mr. Kenneth Cleaver, U.S. Appl. No. 09/199,380, 18 pages (2000).

Remington:The Science and Practice of Pharmacy, $19^{th}$ Edition, p. 710 (1995).

Goodman & Gilman's The Pharmacological Basis of Therapeutics, $10^{th}$ Edition, pp. 704 and 1924 (2001).

Goodman & Gilman's The Pharmacological Basis of Therapeutics, $10^{th}$ Edition, pp. 711 and 1966 (2001).

Martindale; The Extra Pharmacopoeia, $31^{st}$ Edition, p. 1501 (1996).

Experimental report filed by the proprietor in opposition to EP appl. No. 97914779.0 (2007).

Watanabe et al., Pre-Clinical Evaluation of the Transmucosal Oral Absorption System Using a Special Transport System, Jpn J Clin Pharmacol Ther 30(1) Jan. 1999.

Novadel Expert Report to EPO Regarding Opposition to EP 97914779.0 Submitted Sep. 18, 2007.

\* cited by examiner

Mean (± SD) plasma concentrations of meloxicam following administration via transmucosal oral mist and oral suspension at 0.2 mg/kg in dogs.

Figure 2

Pharmacokinetic parameters following dose administration of meloxicam administered to dogs via oral suspension and TMOM.

| | Oral Suspension | TMOM | p-value paired t-test |
|---|---|---|---|
| AUC (µg*h/mL) | 32.3 (20.4-43.8) | 26.8 (17.1-35.4) | 0.08 |
| $C_{max}$ (µg/mL) | 0.93 ± 0.2 | 0.98 ± 0.1 | 0.76 |
| $T_{max}$ (h) | 3.33 ± 1.0 | 2.50 ± 1.2 | 0.19 |
| $t_{½}$ (h) | 30.6 (11.9-50.5) | 28.8 (10.8-57.3) | 0.54 |
| Absorption $t_{½}$ (min) | 96.3 (38.1-242.9) | 35.3 (17.6-74.3) | 0.01 |

Figure 3

Bioequivalence testing between meloxicam administered via TMOM and oral suspension at 0.2 mg/kg in dogs.

| Pharmacokinetic Variable | Geometric mean | 90 % Confidence Interval | |
|---|---|---|---|
| | | Lower Bound (%) | Upper Bound (%) |
| $C_{max}$ (ng/mL) | | | |
| TMOM | 972 | -19.4 | 41.6 |
| Oral Suspension | 910 | | |
| AUC (μg*h/mL) | | | |
| TMOM | 26.8 | -29.5 | -2.0 |
| Oral Suspension | 32.3 | | |

Mean plasma jugular and cephalic concentrations following oral transmucosal administration of meloxicam at 0.1 mg/kg in three anesthetized dogs.

Mean plasma concentrations following oral transmucosal administration of meloxicam at 0.1 mg/kg in three anesthetized dogs and at 0.2 mg/kg in six awake dogs.

Mean (±SD) plasma concentrations of carprofen following administration via transmucosal oral mist, caplet and subcutaneous injection 2.2 mg/kg in dogs.

Figure 7

Pharmacokinetic parameters following administration of carprofen to dogs via caplets, *TMOM* and subcutaneous injection

| | Caplet | *TMOM* | Injectable | ANOVA p value |
|---|---|---|---|---|
| AUC (ng*h/mL) | 114.6 (73.4-132.0) | 122.1 (95.8-173.4) | 119.2 (81.2-162.1) | 0.9 |
| $C_{max}$ (ng/mL) | 22.4 ± 6.2[a] | 22.0 ± 9.1[a] | 10.6 ± 3.4[b] | 0.01 |
| $T_{max}$ (h) | 1.1 ± 0.5[a] | 0.8 ± 0.3[a] | 3.7 ± 0.8[b] | <0.001 |
| $t_{½}$ (h) | 8.1 (6.8-9.5) | 6.6 (4.3-8.6) | 8.2 (6.5-7.6) | 0.2 |
| Lag time (min) | 4.3 ± 2.1[a] | 0 ± 0[b] | 0 ± 0[b] | <0.001 |

Arithmetic Mean ± SD or Geometric Mean (Range) presented
[a,b]Numbers with different superscripts are statistically different via pairwise paired t-tests.

Bioequivalence testing of carprofen administered to dogs via caplets, *TMOM* and subcutaneous injection a. between carprofen administered via caplet and TMOM.

| | | 90 % Confidence Interval | |
|---|---|---|---|
| Pharmacokinetic Variable | Geometric mean | Lower Bound (%) | Upper Bound (%) |
| $C_{max}$ (ng/mL) | | | |
| TMOM | 20.7 | | |
| Caplet | 21.6 | -31 | 32 |
| AUC (µg*h/mL) | | | |
| TMOM | 122 | | |
| Caplet | 115 | -21 | 28 | b. between carprofen administered via caplet and subcutaneous injection.

| | | 90 % Confidence Interval | |
|---|---|---|---|
| Pharmacokinetic Variable | Geometric mean | Lower Bound (%) | Upper Bound (%) |
| $C_{max}$ (ng/mL) | | | |
| Injection | 10.1 | | |
| Caplet | 21.6 | -68 | -32 |
| AUC (µg*h/mL) | | | |
| Injection | 119 | | |
| Caplet | 115 | -11 | 22 |

Mean plasma jugular and cephalic concentrations following oral transmucosal administration of carprofen at 2.2 mg/kg in three anesthetized dogs.

Mean plasma concentrations following oral transmucosal administration of carprofen at 2.2 mg/kg in three anesthetized dogs and six awake dogs.

Mean (± SD) plasma concentrations of clemastine following administration of transmucosal oral mist and tablet formulations at 1.0 mg/kg in cats.

Figure 11

Pharmacokinetic parameters following dose administration of clemastine fumarate administered to cats via tablet and TMOM.

| | Tablet | TMOM | p-value, t test |
|---|---|---|---|
| AUC (ng*h/mL) | 985 (825-1122) | 528 (368-837) | 0.002 |
| $C_{max}$ (ng/mL) | 60.1 ± 5.7 | 59.6 ± 30.2 | 0.97 |
| $T_{max}$ (h) | 5.2 ± 1.6 | 1.0 ± 1.7 | 0.004 |
| $t_{½}$ (h) | 13.6 (10.6-19.6) | 10.5 (6.1-21.3) | 0.4 |

Mean (± SD) plasma concentrations of clemastine following administration of transmucosal oral mist and tablet formulations at 0.1 mg/kg in horses.

Figure 13

Pharmacokinetic parameters following administration of clemastine fumarate to horses via TMOM and oral gavage.

|  | Oral Gavage[1] | TMOM |
|---|---|---|
| $T_{max}$ (h) | 1.0 (0.50-1.50) | 0.8 (0.24-1.01) |
| $t_{½}$ (h) | 2.9 (2.2-5.0) | 2.8 (1.8-5.1) |

[1]From Torneke K, Ingvast-Larsson, Pettersson K, et al., 2003 Pharmacokinetics and pharmacodynamics of clemastine in healthy horses. J Vet Pharmacol Therap 25:151-157

Mean (± SD) plasma concentrations of clemastine following administration via transmucosal oral mist and tablets at 1.0 mg/kg in dogs.

Figure 15

Pharmacokinetic parameters following oral tablet and TMOM administration of clemastine fumarate to dogs.

|  | Tablet | TMOM | p-value, t test |
|---|---|---|---|
| AUC (ng*h/mL) | 3.4 ± 2.4 | 109.3 ± 14.8 | <0.001 |
| $C_{max}$ (ng/mL) | 1.1 ± 0.5 | 23.4 ± 8.1 | <0.001 |
| $T_{max}$ (h) | 0.63 ± 0.3 | 0.46 ± 0.3 | 0.36 |
| $t_{½}$ (h) | 3.6 ± 1.3* | 6.5 ± 0.7 | 0.001 |

*based on 5 of 6 animals, low concentrations achieved, may reflect distribution rather than elimination Mean plasma jugular and cephalic concentrations following oral transmucosal administration of clemastine at 1.0 mg/kg in three anesthetized dogs.

Mean plasma concentrations following oral transmucosal administration of clemastine at 1.0 mg/kg in three anesthetized dogs and six awake dogs.

Mean plasma jugular and cephalic concentrations following oral transmucosal administration of diphenhydramine at 3.0 mg/kg in three dogs.

Figure 20

Pharmacokinetic parameters following administration of diphenhydramine hydrochloride to dogs via TMOM.

| | *TMOM* |
|---|---|
| AUC (µg*h/mL) | 289 (243-322) |
| $C_{max}$ (µg/mL) | 92.8 ± 23.6 |
| $T_{max}$ (h) | 0.4 ± 0.2 |
| $t_{½}$ (h) | 1.9 (1.8-2.0) |

Arithmetic Mean ± SD or Geometric Mean (Range) presented

Mean (± SD) plasma concentrations of zolpidem tartrate following administration via transmucosal mist and tablet at 0.5 mg/kg in dogs.

Mean (± SD) plasma concentrations of zolpidem tartrate following administration via transmucosal mist and tablet at 0.6 mg/kg in cats.

Figure 23

Pharmacokinetic parameters following administration of zolpidem tartrate to dogs via tablet and transmucosal oral mist.

| | Tablet | TMOM | p-value, t test |
|---|---|---|---|
| AUC (ng*min/mL) | 2417 ± (894-5168) | 3937 (2576-6782) | 0.1 |
| $C_{max}$ (ng/mL) | 28.3 ± 16.1 | 68.8 ± 24.5 | 0.005 |
| $T_{max}$ (min) | 52.7 ± 37.5 | 8.1 ± 5 | 0.01 |
| t½ (min) | 57.0 (49.2-74.7) | 50.2 (29.7-67.9) | 0.45 |
| Absorption t½ (min) | 43.5 (25.1-62.5) | 4.7 (0.9-40.7) | 0.005 |

Figure 24

Pharmacokinetic parameters following administration of zolpidem tartrate to cats via tablet and transmucosal oral mist.

| | Tablet | Transmucosal Oral Mist | p-value ANOVA; paired t test |
|---|---|---|---|
| AUC (ng*min/mL)$^\triangledown$ | 8378 ± 2491 | 6191 ± 1993 | |
| C$_{max}$ (ng/mL)$^\triangledown$ | 180 ± 107 | 114 ± 60 | |
| T$_{max}$ (min) | 27.9 ± 18.3 | 14.1 ± 4.3 | 0.10; 0.12 |
| t½ (min) | 41.5 ± 4.5 | 42.0 ± 5.0 | 0.87; 0.84 |

$^\triangledown$These parameters may be overestimated for TMOM due to blood sampling issues Mean plasma concentrations of propofol following intravenous administration at 6.0 mg/kg and administration via transmucosal oral mist at 30.0 mg/kg in dogs.

Figure 26

Pharmacokinetic parameters following intravenous and transmucosal oral mist administration of propofol to dogs.

| | IV | TMOM | p-value paired t-test |
|---|---|---|---|
| AUC/Dose (µg*h/mL) | 219 (145-291) | 7 (2-24) | <0.001 |
| F (%) | | 4 ± 3.5 | |
| $C_{max}$ (µg/mL) | | 267 ± 256 | |
| $T_{max}$ (h) | | 12.8 ± 5.3 | |
| $t_{½}$ (h) | 2.0 (1.5-2.7) | 1.4 (0.6-2.3) | 0.10 |

Figure 28

Pharmacokinetic parameters (corrected for dosage) following administration of milbemycin oxime to dogs via tablet and TMOM.

| | TMOM | | Tablet | p-value, t-test |
|---|---|---|---|---|
| AUC$_{0\to 8h}$/dose (h*ng/mL)/(mg/kg) | 943 (707-1309) | | 1014 (685-2037) | 0.73 |
| | 1$^{st}$ Peak | 2$^{nd}$ Peak | | |
| Corr. C$_{max}$ (ng/mL)/(mg/kg) | 151 ± 93 | 162 ± 40 | 226 ± 101 | 0.37 |
| T$_{max}$ (h) | 0.5 ± 0.1[a] | 2.8 ± 1.0[b] | 1.7 ± 0.5[c] | <0.01 |
| t$_{½}$ (h) | 7.8 (4.8-15.4) | | 7.9 (5.5-11.2) | 0.54 |

Mean (±SD) plasma concentrations of enrofloxacin following administration via transmucosal oral mist and tablets at 5.0 mg/kg in cats.

Figure 30

Pharmacokinetic parameters following administration of enrofloxacin to cats via tablets and *TMOM*.

| | Tablet | *TMOM* | p-value t-test |
|---|---|---|---|
| AUC (μg*h/mL) | 24.6 (21.5-28.2) | 18.1 (13.1-29.8) | 0.07 |
| $C_{max}$ (μg/mL) | 3.5 ± 0.8 | 2.5 ± 1.0 | 0.07 |
| $T_{max}$ (h) | 0.6 ± 0.2 | 0.7 ± 0.3 | 0.45 |
| $t_{½}$ (h) | 7.8 (6.6-8.8) | 7.5 (5.8-8.8) | 0.68 |
| Lag time (min) | 2.6 ± 2.9 | 0 ± 0 | 0.07 |

Arithmetic Mean ± SD or Geometric Mean (Range) presented

Five minute concentrations achieved following administration of enrofloxacin to cats via tablets and *TMOM*.

| Time | 704 | 805 | AMS1 | IJG2 | QJQ1 | QKD2 |
|---|---|---|---|---|---|---|
| Tablet 5 min | 0 | 0 | 0 | 2.6 | 3.1 | 0.3 |
| TMOM 5 min | 45 | 20 | 1485.3 | | 1716.4 | 1600.4 |

Figure 31

Jugular and cephalic sampling following enrofloxacin administration to cats via *TMOM*

| Cat ID Number | Jugular Sample Time | Jugular Sample Concentration | Cephalic Sample Time | Cephalic Sample Concentration |
|---|---|---|---|---|
| 704 | 0:04:16 | 45.7 | 0:04:51 | 45 |
| 805 | 0:05:35 | 52.2 | 0:08:47 | 20 |
| AMS1 | 0:04:45 | 4762.8 | 0:06:20 | 1485.3 |
| IJG2 | 0:09:50 | 30.9 | 0:05:56 | 262.7 |
| QJQ1 | 0:05:51 | 2855.4 | 0:05:54 | 1716.4 |
| QKD2 | 0:04:49 | 4170.7 | 0:07:41 | 1600.4 |

Acceptability of three flavored vehicles and water administered via transmucosal oral mist to dogs.

Severity of reaction after administration of three vehicles and water via transmucosal oral mist to dogs.

Acceptability of three flavored vehicles and water administered via transmucosal oral mist to cats.

Severity of reaction after administration of three vehicles and water via transmucosal oral mist to cats.

Acceptability of three formulations of meloxicam with and without sweeteners administered via transmucosal oral mist to dogs.

Severity of reaction after administration of three formulations of meloxicam with and withou sweeteners administered via transmucosal oral mist to dogs.

Severity of reaction after administration of five formulations with and without sweeteners and/or flavoring agents administered via transmucosal oral mist to dogs.

Severity of reaction after multiple administrations of three vehicles and water via transmucosal oral mist to dogs.

Severity of reaction after multiple administrations of three vehicles and water via transmucosal oral mist to cats.

Severity of reaction after multiple administrations of three formulations of meloxicam with and without sweeteners administered via transmucosal oral mist to dogs.

Severity of reaction after multiple administrations of five formulations with and without sweeteners and/or flavoring agents administered via transmucosal oral mist to dogs.

Figure 44

Overall acceptability of the transmucosal oral mist administration of various vehicles and formulations in dogs over three different studies

| Acceptability Study | Percentage of Successful Dose Administrations | Percentage of Dose Administrations Requiring No Assistance | Percentage of Dose Administrations Considered Acceptable | Number of Dose Administrations |
|---|---|---|---|---|
| #1 | 99.3 | 100.0 | 99.5 | 600 |
| #3 | 99.4 | 100.0 | 100 | 180 |
| #4 | 97.7* | 98.7 | 100 | 300 |
| Total | 98.9 | 99.6 | 99.7 | 1080 |

*inadequate fill volume resulted in incomplete dosing

Overall acceptability of the transmucosal oral mist administration of various vehicles in cats.

| Acceptability Study | Percentage of Successful Dose Administrations | Percentage of Dose Administrations Requiring No Assistance | Percentage of Dose Administrations Considered Acceptable | Number of Dose Administrations |
|---|---|---|---|---|
| #2 | 95.8 | 99.5 | 96.3 | 600 |

TRANSMUCOSAL ADMINISTRATION OF DRUG COMPOSITIONS FOR TREATING AND PREVENTING DISORDERS IN ANIMALS

This application is a continuation of U.S. application Ser. No. 11/356,451, filed on Feb. 17, 2006, now U.S. Pat. No. 8,097,614 which claims priority to U.S. Provisional Application Ser. Nos. 60/664,183 filed Mar. 23, 2005; 60/653,964 filed Feb. 17, 2005; 60/661,920 filed Mar. 16, 2005; 60/664,939 filed Mar. 25, 2005; 60/665,525 filed Mar. 28, 2005; 60/664,181 filed Mar. 23, 2005; 60/664,938 filed Mar. 25, 2005; 60/669,888 filed Apr. 11, 2005; 60/670,651 filed Apr. 13, 2005; and 60/693,942 filed Jun. 27, 2005, each of which is herein incorporated by reference in its entirety for all purposes.

FIELD OF THE INVENTION

In one embodiment, the present invention relates to the transmucosal administration of pharmaceutical compositions to an animal for use in treating or preventing disorders. In particular, embodiments of the invention encompass compositions comprising and methods of using various active agents for combating various diseases or conditions in an animal, preferably a domestic animal, by transmucosally administering a prophylactically or therapeutically effective amount of one or more active agents to an animal in need thereof. Preferred administering means include, but are not limited to, sprays or mists of the one or more active agents into the oral cavity of the animal.

BACKGROUND OF THE INVENTION

Pharmaceutical compounds originally developed for human use have also been used in veterinary medicine. However, the effectiveness of human drugs in non-human animals is unpredictable because of metabolic differences between humans and the various non-human animal species. Even for individuals within a species, the effectiveness of a particular drug can be highly variable. For example, $H_1$-receptor antagonists such as clemastine have been used as antihistamines for both humans and animals. However, doses which are effective in humans have been found to be ineffective in canine and equine subjects because of poor oral bioavailability and rapid elimination of the clemastine (see Hansson et al., *Veterinary Dermatology* 2004, 15, pages 152-158; and Törneke et al., *J. Vet. Pharmacol. Therap.* 26, pages 151-157, 2003). Therapeutic plasma levels of clemastine in canine and equine subjects were only obtained by intravenous administration using relatively high (compared to human) doses, which severely limit the utility of clemastine for veterinary applications.

It is known that certain biologically active compounds are better absorbed through the oral mucosa than through other routes of administration, such as through the stomach or intestine. However, formulations suitable for such administration through the oral mucosa present their own problems. For example, the biologically active compound must be compatible with the other components of the composition such as propellants, solvents, etc. Many such formulations have been proposed. For example, U.S. Pat. No. 4,689,233 to Dvorsky et al., describes a soft gelatin capsule for the administration of the anti-coronary drug nifedipine dissolved in a mixture of polyether alcohols. U.S. Pat. No. 4,755,389 to Jones et al., describes a hard gelatin chewable capsule containing nifedipine. A chewable gelatin capsule containing a solution or dispersion of a drug is described in U.S. Pat. No. 4,935,243 to Borkan et al. U.S. Pat. No. 4,919,919 to Aouda et al., and U.S. Pat. No. 5,370,862 to Klokkers-Bethke, describe a nitroglycerin spray for administration to the oral mucosa comprising nitroglycerin, ethanol, and other components. An orally administered pump spray is described by Cholcha in U.S. Pat. No. 5,186,925. Aerosol compositions containing a hydrocarbon propellant and a drug for administration to a mucosal surface are described in U.K. 2,082,457 to Su, U.S. Pat. No. 3,155,574 to Silson et al., U.S. Pat. No. 5,011,678 to Wang et al., and by Parnell in U.S. Pat. No. 5,128,132. It should be noted that these references discuss bioavailability of solutions by inhalation rather than through the membranes to which they are administered. Each of the above-identified references is incorporated herein by reference in its entirety.

Transmucosal absorption through the oral mucosal surfaces allows permeation of pharmaceuticals such as nutrients or drugs directly into the bloodstream and then into the cells within a matter of minutes. Within the oral cavity, a number of mucosal surfaces may be used to deliver pharmaceuticals, including but not limited to: (i) sublingual surfaces, i.e., the mucosal membranes lining the floor of the mouth, (ii) buccal surfaces, i.e., the mucosal membranes lining the cheeks, (iii) lingual surfaces, i.e., the surface membranes of the tongue, (iv) palatal surfaces, i.e., the membranes lining the roof of the mouth, (v) pharyngeal surfaces, i.e., the membranes of the pharynx, (vi) gingival mucosa, i.e., the gums, and (vii) gingival sulcus, i.e., the cavity formed between the teeth and gums. Conventional oral delivery of a drug via ingestion is often not easily accomplished for various reasons such as difficulty that an owner may have in obliging their animal to swallow a tablet or liquid, inability to handle an animal that dislikes the taste of the medication and resists being treated, and medical conditions that make it difficult for animals to take oral formulations. In animals, these limitations are often exacerbated because the animal is unaware that the treatment is intended to improve the animal's physical condition.

It is well known to animal owners and veterinarians alike that oral administration of a drug to an animal has its associated drawbacks (e.g., difficulty stimulating swallowing, the animal spewing out the pill, or failing to receive proper dosage). In addition, conventional oral administration of drugs to animals has disadvantages, such as hepatic first pass metabolism and enzymatic degradation within the gastrointestinal tract, that prohibit administration of certain classes of drugs, especially peptides and proteins. Although intravenous administration may overcome these drawbacks, the invasiveness to the animal, difficulties for the animal owner, as well as increased costs and risks of infection, make intravenous administration a less viable alternative.

The oral mucosa offers an attractive route of transmucosal administration for systemic drug delivery to animals. For example, an oral spray having a non-toxic aerosol pump can deliver a drug directly into the bloodstream. When sprayed into the mouth, micro-sized droplets are immediately absorbed through the mucosal lining into the capillaries, which lie close to the surface of the lining in the mouth. This process can provide for definitive absorption of the drug within a short time span without causing any extra stress to the organs.

Film delivery systems for use on mucosal surfaces are also known. These types of systems, which are water-insoluble and usually in the form of laminated, extruded or composite films, are described in U.S. Pat. Nos. 4,517,173; 4,572,832; 4,713,243; 4,900,554; and 5,137,729, which are incorporated herein by reference in their entirety. U.S. Pat. No. 4,517,173 describes and claims a membrane-adhering film consisting of at least three layers, including a pharmaceutical layer, a poorly water soluble layer, and an intermediate layer. The pharmaceutical layer includes the drug and a cellulose derivative selected from hydroxypropyl cellulose, methyl cellulose, and hydroxypropyl methyl cellulose. The poorly water soluble layer is made by the combination of one or more cellulose derivatives with a poorly water soluble fatty acid, and the intermediate layer is made of cellulose derivatives. U.S. Pat. No. 4,572,832 relates to a soft film for buccal delivery, made by the combined use of a water soluble protein, a polyol, and a polyhydric alcohol such as cellulose and polysaccharides, and also teaches the use of coloring or flavoring agents. U.S. Pat. No. 4,713,243 describes a single or multi-layered bioadhesive thin film made from 40-95% water soluble hydroxypropyl cellulose, 5-60% water-insoluble ethylene oxide, 0-10% water-insoluble ethyl cellulose, propyl cellulose, polyethylene, or polypropylene, and a medicament. The films are three-layered laminates and include a bioadhesive layer, a reservoir layer, and a non water-soluble outer protective layer. U.S. Pat. No. 4,900,554 teaches a soft adhesive film applicable to the oral mucosa containing a systemic drug and comprising a mixture of a vinyl acetate non-water-soluble homopolymer, an acrylic acid polymer, and a cellulose derivative. Finally, U.S. Pat. No. 5,137,729 describes a device for use in the oral cavity having an adhesive layer including a mixture of an acrylic acid polymer, a water-insoluble cellulose derivative, and a pharmaceutical preparation, and a water-insoluble, or sparingly soluble, backing layer. The adhesive layer contains the pharmaceutical and, upon application to the mucosal surface, delivers the drug.

Recently it has been demonstrated that buccal administration of active agents can result in absorption of active agents through the oral mucosa. For example, U.S. Pat. Nos. 5,869,082; 5,955,098; 6,110,486; and 6,676,931, each of which is incorporated by reference in its entirety for all purposes, disclose administration of active agents using a buccal aerosol spray or capsule. In addition, Published U.S. Patent Application Nos. 2005/0025717, 2005/0025716, 2005/0025715, 2005/0025714, 2005/0025713, 2005/0025712, 2005/0002867, 2004/0265239, 2004/0141923, 2004/0136915, 2004/0136914, 2004/0136913, 2004/0120896, 2004/0120895, 2004/0062716, 2003/0211047, 2003/0190286, 2003/0185761, 2003/0095927, 2003/0095926, 2003/0095925, 2003/0082107, 2003/0077229, 2003/0077228, 2003/0077227, and 2003/0039680, each of which is incorporated herein by reference in its entirety, disclose buccal aerosol sprays or capsules using polar and non-polar solvents, which provide biologically active agents for absorption through the oral mucosa.

However, the bioavailability of drugs administered using an aerosol or spray, e.g., to the respiratory system, can depend significantly on the particular formulation used, and even aerosol formulations which provide satisfactory bioavailability of the drug can exhibit undesirable side-effects such as irritation of the mucosal tissue.

SUMMARY OF THE INVENTION

In one embodiment, the present invention is directed to compositions for transmucosal administration to an animal comprising one or more active agents and a pharmaceutically acceptable carrier.

In another embodiment, the invention is directed to methods of treating or preventing a condition in an animal comprising transmucosally administering a composition comprising a therapeutically or prophylactically effective amount of an active agent and a pharmaceutically acceptable carrier.

BRIEF DESCRIPTION OF THE DRAWINGS

FIG. 2 shows a comparison of the pharmacokinetic parameters for administration of meloxicam by oral suspension and administration using TMOM™ to dogs at a dosage of about 0.2 mg/kg. The AUC represents the area under the curve or the total amount of drug exposure to the animal following administration by the two different dosage forms. The $C_{max}$ represents the maximum plasma concentration of meloxicam measured in ng/ml when administered by the dosage forms. The $T_{max}$ denotes the time it takes to reach maximum plasma concentration of meloxicam achieved following administration of both dosage forms. The $t_{1/2}$ is the calculated rate of distribution or elimination of the meloxicam when administered by both dosage forms.

FIG. 3 shows the results of bioequivalence testing in dogs between meloxicam administered via TMOM™ and administration of an oral suspension (~0.2 mg/kg).

FIG. 7 shows pharmacokinetic parameters and bioequivalence data following administration of carprofen to dogs via caplets, TMOM™ and subcutaneous injection.

FIG. 11 shows a comparison of the pharmacokinetic parameters for administration of clemastine fumarate by tablet and administration using TMOM™ to cats at a dosage of approximately 1 mg/kg.

FIG. 13 shows pharmacokinetic parameters following administration of clemastine fumarate to horses via TMOM™ and oral gavage.

FIG. 15 shows the comparison of the pharmacokinetic parameters for the tablet and the TMOM™ when clemastine fumarate is administered to dogs at a dosage of 1 mg/kg.

FIG. 18 shows the mean plasma concentrations following oral transmucosal administration of clemastine at 1.0, 0.5 and 0.125 mg/kg in nine dogs (circles; 3 dogs per dosage). Mean percent inhibition of a modified intradermal skin wheal and flare test using anti canine IgE antibodies in the same nine dogs (squares; 3 dogs per treatment).

FIG. 20 shows pharmacokinetic parameters following the administration of diphenhydramine hydrochloride to dogs, administered via TMOM™.

FIG. 23 shows a comparison of the pharmacokinetic parameters for administration of zolpidem tartrate by oral suspension and administration using TMOM™ to dogs at a dosage of about 0.5 mg/kg.

FIG. 24 shows the comparison of the pharmacokinetic parameters for the oral suspension and TMOM™ when zolpidem tartrate is administered to cats at a dosage of about 0.6 mg/kg.

FIG. 26 shows pharmacokinetic parameters following administration of propofol to dogs via intravenous administration and TMOM™

FIG. 27 shows MEAN (+/−SD) plasma concentrations (corrected for dosage) of milbemycin following administration via transmucosal oral mist at 0.28 mg/kg and via chewable tablet at 0.78 mg/kg in dogs.

FIG. 28 shows pharmacokinetic parameters (corrected for dosage) following administration of milbemycin oxime to dogs via tablet and TMOM™

FIG. 30 is a chart of pharmacokinetic parameters following administration of enrofloxacin to cats via tablets and TMOM™.

FIG. 31 is a chart of jugular and cephalic plasma concentrations of enrofloxacin in felines after administration via TMOM™.

FIG. 44 is a chart of canine and feline response to TMOM™ administration.

FIG. 45 shows mean plasma concentrations after transmucosal oral administration of clemastine at increasing dosages from 0.25 to 1 mg/kg correspondings to increasing dose volumes from 20 to 80 microliters per kilogram body weight.

DETAILED DESCRIPTION OF THE INVENTION

A. General

Figure 1:
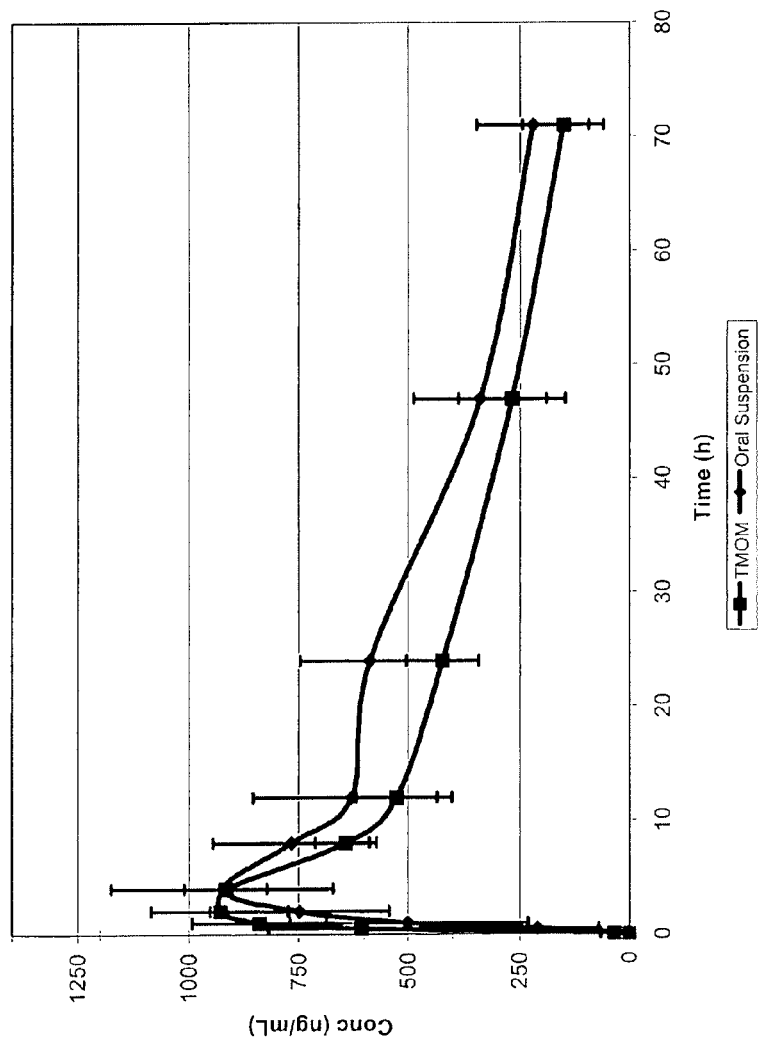
FIG. 1 shows the mean plasma concentrations of meloxicam when administered using two different dosage forms (oral suspension and transmucosal oral mist (hereinafter, "TMOM™")) at the same dosage (~0.2 mg/kg). The oral suspension was administered to the dog orally and was swallowed. The mist was sprayed into the oral cavity of the dogs.

In one embodiment, the present invention is directed to compositions for transmucosal administration to animals comprising at least one active agent and a pharmaceutically acceptable carrier.

In another embodiment, the present invention encompasses novel methods of transmucosally administering compositions comprising a therapeutically or prophylactically effective amount of at least one active agent to an animal in need thereof.

In one embodiment, the compositions of the present invention may be administered to any mucosal surface of the animal, preferably a membrane of the oral mucosa, including lingual surfaces, sublingual surfaces, buccal surfaces, palatal surfaces, and pharyngeal surfaces, preferably buccal or gingival surfaces. In other embodiments, the compositions of the present invention may also be administered to more than one membrane of the oral mucosa, for example the lingual and sublingual surfaces or the lingual, sublingual and buccal surfaces, etc. In yet other embodiments, the compositions of the present invention can be administered to the area of the oral cavity of an animal between the teeth and cheek, thereby allowing the compositions of the present invention to contact at least the buccal and gingival mucosa.

Transmucosal administration of the compositions of the present invention can be carried out using a spray, such as an aerosol or pump spray.

In another embodiment of the compositions of the present invention, at least one active agent is selected from the group consisting of a non-steroidal anti-inflammatory agent, an antiparasitic agent, an antihistamine, a cardiovascular agent, a hormone, an immunosuppressive agent, a nutraceutical, a vitamin, a mineral, a sedative/tranquilizer/behavior modifying agent, an anti-emetic, and an antibiotic, in combination with a pharmaceutically acceptable carrier. The compositions of the present invention are suitable for transmucosal administration, preferably to the oral mucosa and more preferably for administration to the buccal mucosa or other oral mucosal surfaces.

The transmucosal administration methods of the embodiments described herein provide for an easily administered, safe and highly potent method for administering drugs to animals. Compositions administered transmucosally to the oral mucosa of an animal are easier to administer than, for example a pill, may decrease the amount of drug needed, and, in turn, decrease adverse effects, while providing maximum dose response. Additionally, a shorter time frame needed to achieve maximum plasma concentration and greater bioavailability may be provided by the compositions and methods of the invention.

The present invention is described herein using several definitions, as set forth below and throughout the application.

B. Definitions

As used herein and unless otherwise indicated, the term "active agent of the invention" and "active agent" refer to an active agent selected from the group consisting of a non-steroidal anti-inflammatory agent, an antiparasitic agent, an antihistamine, a cardiovascular agent, a hormone, an immunosuppressive agent, a nutraceutical, a vitamin, a mineral, a sedative/tranquilizer/behavior modifying agent, an anti-emetic, and an antibiotic, or pharmaceutically acceptable salts, solvates or derivatives (e.g., esters) thereof.

As used herein and unless otherwise indicated, the term "non-steroidal anti-inflammatory agent" refers to a non-steroidal compound which reduces inflammation or inflammatory responses in an animal, for example COX-1 and COX-2 inhibitors.

As used herein and unless otherwise indicated, the term "antiparasitic agent" refers to any agent capable of killing or inhibiting the growth and reproduction of animal parasites.

As used herein and unless otherwise indicated, the term "antihistamine" refers to compound which counteracts the physiological effects of histamine production in an animal, e.g., in allergic reactions.

As used herein and unless otherwise indicated, the term "cardiovascular agent" refers to a compound capable of treating or ameliorating cardiac conditions or symptoms in an animal, e.g., an illness or condition caused by abnormal/irregular heartbeat, weakness, reduced exercise tolerance, lethargy, hypoxia, syncope, shortness of breath, pulmonary edema or ascites, and/or loss of consciousness, and the like, and combinations thereof.

As used herein and unless otherwise indicated, the term "hormone" refers to a substance, e.g., a peptide or steroid produced by one tissue and conveyed by the bloodstream to another to effect physiological activity in an animal, such as growth or metabolism; or a synthetically prepared compound which acts like a natural hormone.

As used herein and unless otherwise indicated, the term "immunosuppressive agent" refers to a compound which suppresses or inhibits the immune response in an animal.

As used herein and unless otherwise indicated, the term "nutraceutical" refers to a compound, extract, or product that has been isolated or purified from food, plants, or edible matter, and that provides a detectable physiological benefit.

As used herein and unless otherwise indicated, the term "vitamin" refers to an organic compound that is required in trace (or relatively small) amounts for normal growth and metabolic processes, and, to the extent that the body cannot or does not make such organic compounds, they must be obtained, at least in part, or metabolized from food or other synthetic or natural sources.

As used herein and unless otherwise indicated, the term "mineral" refers to an inorganic moiety that, like a vitamin, is required in trace (or relatively small) amounts for normal growth and metabolic processes, and, to the extent that the body cannot or does not make such organic compounds, they are typically obtained, at least in part, or metabolized from food or other synthetic or natural sources. Such inorganic moieties can be bonded to or associated with (e.g., covalently, ionically, as salts, in hydrogen-bonded form, complexed with, or the like) organic moieties to increase their bioavailability or absorption in or by the body.

As used herein and unless otherwise indicated, the term "sedative/tranquilizer/behavior modifying agent" refers to a compound which has a sedative, tranquilizing, or anesthetic effect on an animal.

As used herein and unless otherwise indicated, the term "anti-emetic" refers to a compound which prevents, reduces, or stops emesis or nausea in an animal.

As used herein and unless otherwise indicated, the term "antibiotic" refers to a compound that can destroy or inhibit the growth of other microorganisms (e.g., bacteria) in an animal.

As used herein and unless otherwise indicated, the term "about" will be understood by persons of ordinary skill in the art and will vary to some extent on the context in which the term is used. If there are uses of the term which are not clear to persons of ordinary skill in the art given the context in which it is used, "about" will mean up to plus or minus 10% of the particular term or amount.

As used herein and unless otherwise indicated, the term "alkanoyl esters" refers to a monovalent group of the formula —C(O)-alkoxy. Preferably, the hydrocarbon chain of an alkoxy group is from 1 to 8 carbon atoms in length.

As used herein and unless otherwise indicated, the term "alkoxy group" refers to an —O-alkyl group, wherein alkyl is as defined below. An alkoxy group can be unsubstituted or substituted with one or two suitable substituents. Preferably, the alkyl chain of an alkoxy group is from 1 to 8 carbon atoms in length, and an alkoxy group having 1 to 8 carbon atoms is referred to herein as a "$(C_1-C_8)$alkoxy."

The term "alkyl group" means a saturated, monovalent, unbranched (i.e., linear) or branched hydrocarbon chain, for example a saturated hydrocarbon chain (i.e., a chain of carbon atoms substituted with hydrogen) which is from 1 to 18 carbons in length (referred to herein as a "$(C_1-C_{18})$alkyl"), a $(C_1-C_8)$ hydrocarbon chain, or a $(C_1-C_6)$ hydrocarbon chain. The alkyl groups of the present invention may be unsubstituted or optionally substituted with one or two suitable substituents. Examples of alkyl groups, include but are not limited to, $(C_1-C_6)$alkyl groups, such as methyl, ethyl, propyl, isopropyl, 2-methyl-1-propyl, 2-methyl-2-propyl, 2-methyl- 1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl and octyl.

The term "hydrocarbon group" can be used interchangeably with the term "alkyl group" when the "hydrocarbon group" is a saturated hydrocarbon. However, the term "hydrocarbon group" further includes monovalent unsaturated hydrocarbons, e.g., alkenyl and alkynyl groups. Suitable hydrocarbon groups thus include, for example, monovalent groups selected from $(C_1-C_8)$alkyl, $(C_2-C_8)$alkenyl, and $(C_2-C_8)$alkynyl, optionally substituted with one or two suitable substituents. Preferably, the hydrocarbon chain of a hydrocarbon group is from 1 to 6 carbon atoms in length, referred to herein as "$(C_1-C_6)$hydrocarbon". Examples of hydrocarbon groups include, but are not limited to the alkyl groups described above, and in addition, unsaturated hydrocarbons such as vinyl, allyl, 1-propenyl, 1-butenyl, 2-butenyl, 3-butenyl, 1-ethynyl, 1-propynyl, 2-propynyl, etc.

Similarly, the term "hydrocarbon" refers to a molecule consisting of carbon and hydrogen. The hydrocarbons of the present invention may also be optionally substituted. Suitable hydrocarbons of the present invention have 4 or more carbon atoms, preferable 4 to 18 carbon atoms.

As used herein and unless otherwise indicated, the term "additional therapeutic agent(s)" refers to a second (or third, etc.) drug (and/or a pharmaceutically acceptable salt, solvate or ester thereof) added in addition to the active agent and can include agents to enhance absorption of the drug or combinations including, but not limited to, permeation enhancers or bioadhesive agents.

As used herein and unless otherwise indicated, the term "animal" refers to any non-human animal, including mammals, birds, reptiles, marsupials, amphibians, and fish. In one preferred embodiment, the term "animal" includes domesticated animals, such as a cow, horse, sheep, pig, goat, chicken, turkey, quail, duck, goose, cat, dog, mouse, rat, rabbit, or guinea pig, and is preferably a dog, cat, or horse. The term "animal" also includes wild, non-domesticated animals and exotic animals in captivity, for instance, undomesticated "pets" and animals held in zoological or other captive environments.

As used herein and unless otherwise indicated, the terms "bioadhesive agents" and "bioadhesive polymers" refer to any agents that can adhere onto a biological surface, preferably the oral mucosa and more preferably the buccal mucosa, to increase the time a drug is in contact with the oral mucosa, and therefore to increase its absorption.

As used herein and unless otherwise indicated, the term "buccal mucosa" refers to oral mucosal membranes lining the cheeks.

As used herein and unless otherwise indicated, the term "transmucosal oral administration" includes any method of administering an active agent to the oral cavity of an animal in which a substantial portion of the active agent enters the blood stream of the animal by diffusion or movement through any of the mucus membranes of the oral cavity. By "substantial portion" is meant at least 20% of the active ingredient in the dose administered enters the blood stream of the animal by movement through the mucus membranes of the oral cavity. Preferably, at least 50%, more preferably, at least 80% enters the blood stream of the animal by movement through the mucus membranes of the oral cavity.

As used herein and unless otherwise indicated, the term "transmucosal oral mist" includes forms of a formulation intended to be administered to an animal by a transmucosal oral administration method in which the formulation is administered in the form of droplets which contact the oral mucosa of the animal. The droplets can be of any size or size distribution, and includes very fine droplets capable of being suspended in air (e.g., aerosols), or coarser droplets of the sort provided by conventional spray devices, including pump sprays, aerosol sprays, etc.

As used herein and unless otherwise indicated, the term "effective amount" means an amount of an active agent, or a pharmaceutically acceptable salt thereof, that is sufficient to provide the desired local or systemic effect and performance at a reasonable benefit/risk ratio attending any medical treatment. Particularly, the term "effective amount" means an amount of active agent, or a pharmaceutically acceptable salt, solvate or ester thereof, that is sufficient to mitigate, ameliorate, substantially reduce, or cause the cessation of at least one adverse effect associated with the illness or condition being treated, or at least one discernible symptom of the condition, disease, or illness sought to be treated by the compositions according to the invention. "Therapeutically effective" also refers to an amount of active agent that results in an amelioration of at least one measurable physical parameter, not necessarily discernible, by the animal. In yet another embodiment, the term "therapeutically effective" refers to an amount of active agent sufficient to inhibit the progression of at least one adverse effect, whether physically (e.g., stabilization of a discernible symptom), physiologically (e.g., stabilization of a physical parameter), or both. In yet another embodiment, the term "therapeutically effective" refers to an amount of active agent resulting in a delayed onset of a disease or disorder. The amount of active agent constituting a "therapeutically effective amount" will vary depending on the illness, condition, disorder, or disease be treated or prevented, the severity of the condition, and the age and body weight of the animal to be treated, but can be determined routinely by one of ordinary skill in the art having regard to his/her own knowledge and to this disclosure.

When the active agent is a non-steroidal anti-inflammatory agent, the term "therapeutically effective" in regard to the amount of non-steroidal anti-inflammatory agent refers to an amount of non-steroidal anti-inflammatory agent capable of causing an amelioration of at least one adverse effect associated with pain, inflammation, and/or fever in an animal, or at least one discernible symptom thereof.

When the active agent is an antiparasitic agent, the term "therapeutically effective" in regard to the amount of antiparasitic agent refers to an amount of antiparasitic agent that results in an amelioration of at least one measurable physical parameter associated with infection of the animal by a parasite, for example, kill the parasite When the active agent is an antihistamine, the term "therapeutically effective" in regard to the amount of antihistamine refers to an amount of an antihistamine that results in an amelioration of at least one measurable physical parameter, e.g., reduction in pruritus, decrease in skin inflammation as denoted by reduced erythema, swelling or skin excoriation, reduced scratching, biting or licking to the affected areas of skin, resolution of skin lesions caused by self-trauma and resolution of secondary skin infections.

When the active agent is a cardiovascular agent, the term "therapeutically effective" in regard to the amount of cardiovascular agent refers to an amount of a cardiovascular agent capable of causing an amelioration of at least one adverse effect associated with abnormal/irregular heartbeat, weakness, reduced exercise tolerance, lethargy, hypoxia, syncope, shortness of breath, pulmonary edema or ascites, and/or loss of consciousness, or the like, in an animal, or at least one discernible symptom of the condition, disease, or illness sought to be treated by the compositions according to the invention.

When the active agent is a hormone, the term "therapeutically effective" in regard to the amount of hormone refers to an amount of hormone sufficient to mitigate, substantially reduce, or cause the cessation of at least one adverse effect associated with decreased or non-existent production of the hormone or a metabolite thereof (e.g., hypothyroidism, diabetes, insulin resistance disease, insulinemia, or a combination thereof).

When the active agent is an immunosuppressive agent, the term "therapeutically effective" in regard to the amount of immunosuppressive agent refers to an amount of immunosuppressive agent which, e.g., significantly inhibits or limits an immune response.

When the active agent is a sedative/tranquilizer/behavior modifying agent, the term "therapeutically effective" in regard to the amount of the sedative/tranquilizer/behavior modifying agent refers to an amount of a sedative/tranquilizer/behavior modifying agent capable of causing an amelioration of at least one adverse effect associated with insomnia, stress, separation anxiety, hyperactivity, motion sickness, and/or travel stress or the like, in an animal, or at least one discernible symptom of the condition, disease, or illness sought to be treated by the compositions according to the invention.

When the active agent is an antibiotic, the term "therapeutically effective" in regard to the amount of antibiotic refers to an amount of antibiotic capable of reducing or eliminating bacterial infections or the like in an animal.

When the active agent is an anti-emetic, the term "therapeutically effective" in regard to the amount of anti-emetic refers to an amount of anti-emetic capable of preventing, reducing or eliminating nausea and vomiting in an animal.

As used herein, the term "substantially reduces" refers to the ability of an active agent or composition of the invention to reduce at least one adverse effect, for example as described below. In a preferred embodiment, substantially reduces refers to the ability of an active agent or composition of the invention to reduce or prevent all adverse effects associated with the illness or condition.

When the active agent is a non-steroidal anti-inflammatory drug, an adverse effect includes, but is not limited, to pain, inflammation, fever, and combinations thereof.

When the active agent is an antiparasitic agent, an adverse effect includes, but is not limited to effects associated with an illness caused by animal parasites.

When the active agent is an antihistamine, an adverse effect includes, but is not limited to an allergic reaction. Clinical outcomes that can be interpreted to define "effective" include the following, reduction in pruritus, decrease in skin inflammation as denoted by reduced erythema, swelling or skin excoriation, reduced scratching, biting or licking to the affected areas of skin, resolution of skin lesions caused by self-trauma and resolution of secondary skin infections.

When the active agent is an immunosuppressive, an adverse effect includes, but is not limited to an enhanced or overactive immune response. For example, immunosuppressives can be used to treat arthritis, graft rejection, etc.

When the active agent is a cardiovascular agent, an adverse effect includes, but is not limited to abnormal/irregular heartbeat, weakness, shortness of breath, reduced exercise tolerance, lethargy, syncope, hypoxia, pulmonary edema, ascites, loss of consciousness, and the like, and combinations thereof.

When the active agent is a hormone, an adverse effect includes, but is not limited to decreased or non-existent production of the hormone or a metabolite thereof (e.g., hypothyroidism, diabetes, insulin resistance disease, insulinemia, or a combination thereof).

When the active agent is a sedative/tranquilizer/behavior modifying agent agent, an adverse effect includes, but is not limited to insomnia, stress, separation anxiety, hyperactivity, and the like, and combinations thereof.

When the active agent is a nutraceutical, vitamin, and/or mineral, an adverse effect includes, but is not limited to decreased or non-existent production or dietary intake of the nutraceutical, vitamin, mineral, combination thereof, or a metabolite thereof.

When the active agent is an antibiotic, an adverse effect includes, but is not limited to fever, swelling, discharge, etc. associated with a bacterial infection.

When the active agent is an anti-emetic, an adverse effect includes, but is not limited to nausea, vomiting, dehydration, and weight loss.

When the active agent is a non-steroidal anti-inflammatory agent, the term "prophylactically effective" in regard to the amount of non-steroidal anti-inflammatory agent refers to an amount of non-steroidal anti-inflammatory agent capable of preventively mitigating or preventively substantially reducing adverse effects associated with an illness or condition caused by arthritis, pain, inflammation, fever, or a combination thereof. The compositions of the invention comprising a non-steroidal anti-inflammatory agent may be used for the prevention of at least one adverse effect and concurrently treating another (e.g., prevention of adverse effects of pain, inflammation, and/or fever, while treating another symptom, illness, or condition, for example, emesis and/or diarrhea).

When the active agent is an antiparasitic agent, the term "prophylactically effective" in regard to the amount of antiparasitic agent refers to an amount of antiparasitic agent capable of mitigating or substantially reducing adverse effects associated with an illness caused by animal parasites. Accordingly, the compositions of the invention comprising an antiparasitic agent may be used for the prevention of at least one adverse effect and concurrently treating another (e.g., prevention of adverse effects of a parasite while treating emesis or diarrhea).

When the active agent is an antihistamine, the term "prophylactically effective" in regard to the amount of antihistamine refers to an amount of active agent capable of preventively mitigating or preventively substantially reducing adverse effects associated with an illness or condition caused by an allergic reaction or condition. The compositions of the invention comprising an antihistamine may be used for the prevention of at least one adverse effect and concurrently treating another (e.g., prevention of adverse effects of an allergic reaction or condition, while treating another symptom, illness, or condition, for example, emesis, diarrhea, and/or pruritis).

When the active agent is a cardiovascular agent, the term "prophylactically effective" in regard to the amount of cardiovascular agent refers to an amount of active agent capable of preventively mitigating or preventively substantially reducing adverse effects associated with an illness or condition caused by abnormal/irregular heartbeat, weakness, shortness of breath, reduced exercise tolerance, lethargy, syncope, hypoxia, pulmonary edema, ascites, loss of consciousness, and the like, and combinations thereof. The compositions of the invention comprising a cardiovascular agent may be used for the prevention of at least one adverse effect and concurrently treating another (e.g., prevention of adverse effects of abnormal/irregular heartbeat, weakness, shortness of breath, reduced exercise tolerance, lethargy, syncope, hypoxia, pulmonary edema, ascites, loss of consciousness, and the like, and combinations thereof, while treating another symptom, illness, or condition, for example, emesis and/or diarrhea). Illnesses or conditions being treated can include, but are not limited to, severe or congestive heart failure, right heart failure due to heartworm or other agent, atrial fibrillation, atrial flutter, atrial tachycardia, dilated cardiomyopathy, hypertrophic cardiomyopathy, congenital abnormalities, heart failure with glomerulonephritis, idiopathic subaortic stenosis, acute myocardial infarction, myocarditis, myxedema, chronic obstructive pericarditis, ventricular tachycardias, premature ventricular contraction, incomplete AV block, severe pulmonary disease or hypoxia, carotid sinus sensitivity, bradycardia or complete AV block (provided that the block was not caused by digoxin), and combinations thereof.

When the active agent is a hormone, the term "prophylactically effective" in regard to the amount of hormone refers to an amount of active agent capable of preventively mitigating or preventively substantially reducing adverse effects associated with an illness or condition caused by decreased or non-existent production of the hormone or a metabolite thereof. The compositions of the invention comprising a hormone may be used for the prevention of at least one adverse effect and concurrently treating another (e.g., prevention of adverse effects of decreased or non-existent production of the hormone or a metabolite thereof, while treating another symptom, illness, or condition, for example, cardiac events, emesis, and/or diarrhea).

When the active agent is an immunosuppressive agent, the term "prophylactically effective" in regard to the amount of immunosuppressive agent refers to an amount of active agent capable of preventively mitigating or preventively substantially reducing adverse effects associated with an illness or condition caused by enhanced or overactive immune response. The compositions of the invention comprising an immunosuppressive agent may be used for the prevention of at least one adverse effect and concurrently treating another (e.g., prevention of adverse effects of enhanced or overactive immune response, while treating another symptom, illness, or condition, for example, atopic dermatitis associated with allergy resulting in itching and scratching).

When the active agent is a nutraceutical, vitamin, and/or mineral, the term "prophylactically effective" in regard to the amount of nutraceutical, vitamin, and/or mineral refers to an amount of active agent capable of preventively mitigating or preventively substantially reducing adverse effects (e.g., those typical or symptomatic of nutritional deficiencies) associated with an illness or condition caused by decreased or non-existent production or dietary intake of the nutraceutical, vitamin, mineral, combination thereof, or a metabolite thereof. The term "prophylactically effective" also refers to an amount of active agent capable of therapeutically supplementing the natural production or intake of the nutraceutical, vitamin, mineral, combination thereof, or metabolite thereof. The compositions of the invention comprising a nutraceutical, vitamin, and/or mineral may be used for the prevention of at least one adverse effect and concurrently treating another (e.g., prevention of adverse effects of decreased or non-existent production or dietary intake of the nutraceutical, vitamin, mineral, combination thereof, or a metabolite thereof, while treating another symptom, illness, or condition, for example, allergic reaction, emesis, and/or diarrhea).

When the active agent is a sedative/tranquilizer/behavior modifying agent, the term "prophylactically effective" in regard to the amount of sedative/tranquilizer/behavior modifying agent refers to an amount of sedative/tranquilizer/behavior modifying agent capable of preventively mitigating or preventively substantially reducing adverse effects associated with an illness or condition caused by insomnia, stress, separation anxiety, hyperactivity, and the like, and combinations thereof. The compositions of the invention comprising a sleeping aid agent may be used for the prevention of at least one adverse effect and concurrently treating another (e.g., prevention of adverse effects of insomnia, stress, separation anxiety, hyperactivity, and the like, and combinations thereof, while treating another symptom, illness, or condition, for example, emesis and/or diarrhea).

When the active agent is antibiotic, the term "prophylactically effective" in regard to the amount of antibiotic refers to an amount of antibiotic capable of preventively mitigating or preventively substantially reducing adverse effects associated with an illness or condition caused by a bacterial infection. The compositions of the invention comprising an antibiotic may be used for the prevention of at least one adverse effect and concurrently treating another (e.g., eliminating a bacterial infection while treating another symptom, illness, or condition, for example, fever and pain).

When the active agent is anti-emetic agent, the term "prophylactically effective" in regard to the amount of anti-emetic agent refers to an amount of anti-emetic agent capable of preventively mitigating or preventively substantially reducing adverse effects associated with nausea, vomiting, and the like, and combinations thereof. The compositions of the invention comprising an anti-emetic agent may be used for the prevention of at least one adverse effect and concurrently treating another (e.g., prevention of adverse effects of dehydration, weight loss, and the like, and combinations thereof, while treating another symptom, illness, or condition, for example, cancer or pain).

As used herein, the terms "flavoring agent" and "masking agent" refer to any agent that improves the palatability or acceptability of an agent or composition to an animal. Such agents may improve taste, odor, or both, such that an animal more easily accepts treatment according to the invention.

As used herein and unless otherwise indicated, the term "nonpolar solvent" includes, but is not limited to, ($C_2$-$C_{24}$) fatty acid ($C_2$-$C_6$) esters, ($C_7$-$C_{18}$) hydrocarbons, ($C_2$-$C_6$) alkanoyl esters, and the triglycerides of the corresponding acids.

As used herein and unless otherwise indicated, the term "transmucosal administration" refers to administration of the active agent of the invention to a mucous membrane, thereby allowing diffusion of the active agent through the mucous membrane.

As used herein and unless otherwise indicated, the term "oral mucosa" refers to any mucosal surface found in the oral cavity or reachable by administration to the oral cavity, including but not limited to: (i) lingual surfaces, i.e., the surface membranes of the tongue, (ii) sublingual surfaces, i.e., the mucosal membranes lining the floor of the mouth, (iii) buccal surfaces, i.e., the mucosal membranes lining the cheeks, (iv) palatal surfaces, i.e., the membranes lining the roof of the mouth, (v) pharyngeal surfaces, i.e., mucous membranes lining the pharynx, (vi) gingival surfaces, i.e., mucous membranes of the gums, and (vii) gingival sulcus, i.e., the cavity formed between the teeth and gums. When the animal is a fish, the term "oral mucosa" includes any of the mucosa of the gills of the fish.

As used herein and unless otherwise indicated, the term "penetration enhancer(s)" refers to any substance(s) used to increase the flux of drugs through the oral mucosa.

As used herein, the term "pharmaceutical" includes, but is not limited to, any agent, compound or mixture thereof that induces a detectable physiological, metabolic, phenotypic, or other change in the animal regardless of molecular composition and can include, but is not necessarily limited to, small organic molecules, biological molecules, nutrients, vitamins, metabolites, foods, vaccines, proteins lipids, and carbohydrates.

As used herein and unless otherwise indicated, the term "pharmaceutically acceptable" means approved or approvable by a regulatory agency of the Federal or a state government or listed in the U.S. Pharmacopoeia or other generally recognized pharmacopoeia for use in animals. The term "vehicle" refers to a diluent, adjuvant, excipient, or carrier with which active agent of the invention is administered. Such pharmaceutical vehicles can be liquids, such as water or aqueous alcohol (e.g., aqueous ethanol) and oils, including those of petroleum, animal, vegetable, or synthetic origin, such as peanut oil, soybean oil, mineral oil, sesame oil, and the like. The pharmaceutical vehicles can also include, e.g., saline, aqueous alcohol, or water. When administered to an animal, the active agents of the invention and pharmaceutically acceptable vehicles are preferably sterile. Aqueous ethanol is a preferred vehicle, as the agents of the invention are administered transmucosally. The present compositions, if desired, can also contain minor amounts of wetting or emulsifying agents, and/or pH buffering agents.

As used herein and unless otherwise indicated, the term "polar solvent" includes, but is not limited to, low molecular weight polyethyleneglycols (PEG) of 400-1000 Mw (preferably 400-600), low molecular weight ($C_2$-$C_8$) mono- and polyols and alcohols of ($C_7$-$C_{18}$) linear or branch chain hydrocarbons. Glycerin may also be present, and water may also be used in the sprays. A preferred polar solvent is aqueous ethanol.

As used herein and unless otherwise indicated, the term "nonpolar solvent" includes, but is not limited to a $C_7$-$C_{18}$ hydrocarbon of a linear or branched configuration, fatty acid esters, triglycerides, or miglyol.

As used herein and unless otherwise indicated, the term "transmucosal" refers to the diffusion of the active agent of the invention through a mucous membrane, preferably the oral mucosa and more preferably the buccal mucosa.

As used herein and unless otherwise indicated, the terms "AUC", "$T_{max}$", "$C_{max}$" and "$t_{1/2}$," have their conventional meanings. Thus, "AUC" represents the area under the curve or the total amount of active agent exposure to the animal following administration. The term "$C_{max}$" represents the maximum plasma concentration of active agent measured in the indicated units, after administration to the animal. The term "$T_{max}$" denotes the time it takes the active agent to reach maximum plasma concentration in the animal following administration. The $t_{1/2}$, is the calculated rate of distribution or elimination of the active agent after administration. The absorption $t_{1/2}$, is the calculated absorption half-life of the active agent.

C. Compositions of the Invention

The invention encompasses the transmucosal administration of a non-steroidal anti-inflammatory active agent composition comprising at least one active agent, and transmucosal administration of combinations of at least one active agent and at least one additional therapeutic agent.

Formulations suitable for transmucosal administration include those described in WO 2005/030167, WO 2005/032520, WO 2005/032518, WO 2005/032519, and WO 2005/032517, each of which is herein incorporated by reference in its entirety for all purposes.

The active agent or agents of the compositions of the various embodiments of the present invention can have a concentration in the range of about 0.01 to about 10 wt. % of the composition. In other embodiments, the active agent concentration can be about 0.05 wt. %, 0.10 wt. %, 0.5 wt. %, 1.0 wt. %, 1.5 wt. %, 2.0 wt. %, 2.5 wt. %, 3.0 wt. %, 3.5 wt. %, 4.0 wt. %, 4.5 wt. %, 5.0 wt. %, 5.5 wt. %, 6.0 wt. %, 6.5 wt. %, 7.0 wt. %, 7.5 wt. %, 8.0 wt. %, 8.5 wt. %, 9.0 wt. %, and 9.5 wt. %, inclusive of all values and subranges therebetween.

Non-limiting examples of suitable non-steroidal anti-inflammatory agents are meloxicam, carprofen, tepoxalin, firocoxib, deracoxib, etodolac, ibuprofen, naproxen, ketoprofen, celecoxib, and rofecoxib. In one embodiment, the non-steroidal anti-inflammatory agent is meloxicam, (4-hydroxy-2-methyl-N-(5-methyl-2-thiazolyl)-2H-1,2-benzothiazine-3-carboxamide-1,1-dioxide) or a pharmaceutically acceptable salt, solvate or ester thereof. Various salts of meloxicam that can also be used in compositions according to the invention are described in European Patent No. EP 0 002 482 B1, U.S. Pat. No. 4,233,299, and PCT Publication No. WO 99/49867, the disclosures of each of which are each incorporated by reference in their entirety for all purposes.

Antiparasitic agents of the invention include any agent capable of therapeutically or prophylactically treating the presence of a parasite in animal, for example the macrocyclic lactones such as abamectin, ivermectin, eprinomectin, doramectin, moxidectin, selamectin, milbemycin oxime. In one embodiment, the antiparasitic agents include, but are not limited to, endoparasiticidal agents, ectoparaciticidal agents, and endectoparaciticidal agents. In a particular embodiment, the antiparasitic agent is an avermectin, milbemycin, phenylpyrazole, nodulisporic acid, clorsulon, closantel, quinacrine, chloroquine, vidarabine, nitenpyram, ivermectin, milbemycine oxime, lufenuron, salimectin, moxidectin, or dorimectin. In a more particular embodiment, the antiparasitic agent is nitenpyram, ivermectin, milbemycine oxime, lufenuron, salimectin, moxidectin, dorimectin, or paraherquamide, or pharmaceutically acceptable salts, solvates or esters thereof.

Non-limiting examples of suitable antihistamines include clemastine, clemastine fumarate (2(R)-[2-[1-(4-Chlorophenyl)-1-phenyl-ethoxy]ethyl-1-methylpyrrolidine), dexmedetomidine, doxylamine, loratidine, desloratidine and promethazine, and diphenhydramine, or pharmaceutically acceptable salts, solvates or esters thereof.

Non-limiting examples of suitable cardiovascular agents includes digoxin, or (3β,5β,12β)-3-[(O-2,6-dideoxy-β-D-ribo-hexopyranosyl-(1,4)-O-2,6-dideoxy-β-D-ribo-hexopyranosyl-(1,4)-O-2,6-dideoxy-β-D-ribo-hexopyranosyl)oxy]-12,14-dihydroxy-card-20(22)-enolide, ACE inhibitors such as lisinopril, captopril, ramipril, trandolapril, benazepril, cilazapril, enalapril, moexipril, perindopril, quinapril, and Enalaprilat, including pharmaceutically acceptable salts, solvates or esters thereof. Digoxin can exist in a white crystalline form that melts/decomposes above about 230° C. and that is practically insoluble in water and in ether, is slightly soluble in diluted (e.g., about 50%) alcohol and in chloroform, and is freely soluble in pyridine.

Non-limiting examples of suitable hormones include levothyroxin(e) salt, e.g., sodium levothyroxin(e), epinephrine, insulin, and pharmaceutically acceptable salts, solvates, or esters thereof.

Non-limiting examples of suitable sedative/tranquilizer/behavior modifying agents include zolpidem, or N,N-6-trimethyl-2-p-tolyl-imidazo[1,2-a]pyridine-3-acetamide, and propofol. A preferred salt of zolpidem is a tartrate salt, more preferably a bitartrate salt (i.e., referred to generically herein as zolpidem tartrate, which is listed as the active ingredient in, e.g., Ambient, commercially available from Sanofi-Synthelabo of New York, N.Y.). In addition, sedative/tranquilizer/behavior modifying agents can include selective serotonin reuptake inhibitors such as clomipramine, or monoamine oxidase inhibitors such as selegiline.

Non-limiting examples of suitable anti-emetic agents include phenothiazines (e.g., prochloperazine, promethazine, thiethylperazine, perphenazine, chlorpromazine, metopimazine, acepromazine, etc.); 5HT-3 receptor antagonists such as ondansetron, granisetron, tropisetron, dolasetron, hydrodolasetron, azasetron, ramosetron, lerisetron, indisetron and palonosetron; and others such as dimenhydrinate, diphenhydramine (which can also act as an antihistamine), cyclizine, meclizine, promethazine, hyroxyzine, metoclopramide, domperidone, hyoscine, hyoscine hydrobromide, hyoscine hydrochloride, scopolamine, clebopride, alizapride, itopride, bromopride, droperidol, haloperidol, benzquinamide, cerium oxalate, diphenidol, dronabinol, nabilone, ginger, levosulpiride, butorphanol and aprepitant.

Non-limiting examples of suitable antibiotics include beta-lactams such as penicillins, aminopenicillins (e.g., amoxicillin, ampicillin, hetacillin, etc.), penicillinase resistant antibiotics (e.g., cloxacillin, dicloxacillin, methicillin, nafcillin, oxacillin, etc.), extended spectrum antibiotics (e.g., axlocillin, carbenicillin, mezlocillin, piperacillin, ticarcillin, etc.); cephalosporins (e.g., cefadroxil, cefazolin, cephalixin, cephalothin, cephapirin, cephradine, cefaclor, cefacmandole, cefmetazole, cefonicid, ceforanide, cefotetan, cefoxitin, cefprozil, cefuroxime, loracarbef, cefixime, cefoperazone, cefotaxime, cefpodoxime, ceftazidime, ceftiofur, ceftizoxime, ceftriaxone, moxalactam, etc.); monobactams such as aztreonam; Carbapenems such as imipenem and eropenem; quinolones (e.g., ciprofloxacin, enrofloxacin, difloxacin, orbifloxacin, marbofloxacin, etc.); chloramphenicols (e.g., chloramphenicol, thiamphenicol, florfenicol, etc.); tetracyclines (e.g., chlortetracycline, tetracycline, oxytetracycline, doxycycline, minocycline, etc.); macrolides (e.g., erythromycin, tylosin, tlimicosin, clarithromycin, azithromycin, etc.); lincosamides (e.g., lincomycin, clindamycin, etc.); aminoglycosides (e.g., gentamicin, amikacin, kanamycin, apramycin, tobramycin, neomycin, dihydrostreptomycin, paromomycin, etc.); sulfonamides (e.g., sulfadmethoxine, sfulfamethazine, sulfaquinoxaline, sulfamerazine, sulfathiazole, sulfasalazine, sulfadiazine, sulfabromomethazine, suflaethoxypyridazine, etc.); glycopeptides (e.g., vancomycin, teicoplanin, ramoplanin, and decaplanin; and other antibiotics (e.g., rifampin, nitrofuran, virginiamycin, polymyxins, tobramycin, etc.).

Nutraceuticals can include, but are not limited to, micronutrients such as vitamins and minerals, dietary supplements such as those regulated by the U.S. Food & Drug Administration, amino acids, herbs, antioxidants, tribal medicines, prebiotics, probiotics, macrobiotics, nutritional supplements, and the like, as well as combinations thereof. Examples of nutraceuticals can include, but are not limited to, Astralagus, Bilberry, Black cohosh, *Echinacea,* Elderberry, Ginkgo, *Ginkgo Biloba*, Ginseng, Olive Leaf, Palmetto, Saw Palmetto, Saw Palmetto Berries, Amla, Chuchusai, Lion's Mane, *Agaricus*, Royal *Agaricus*, Shatavari, Aloe Vera, Artichoke Leaves, *Avena Sativa* (wild oats), Bayberry, Bayberry Bark, Bayberry Root, Bayberry Bark of Root, Beet Root, Bitter Orange Herb, Black Cohosh Root, Black Walnut Hull, Bladderwrack, Thistle, Blue Cohosh, Burdock Root, Butcher's Broom, Cascara Sagrada, *Cassia* Nomame, Cat's Claw, Cat's Claw Bark, Catuaba Bark, Cayenne, Chickweed, Chamomile, Cordyceps, Cranberry extract, Dandelion Root, Devil's Claw, Dong Quai, *Echinacea* Root, *Echinacea angustfolia* Root, *Echinacea purpurea* Herb, *Echinacea purpurea* Root, *Echinacea pillida*, Elderberry Berries, Elderberry Flowers, Sweet Elder, Eleuthero, Eyebright, Feverfew leaves, Fo-Ti, Nettle Leaf, Ginger, Goldenseal, Gotu Kola, Grapefruit Seed Extract, Guarana, Hawthorn berries, Hops, Horsetail, Hyssop, Juniper Berries, Kelp, Kelp Iodine, Lemon Balm Herb, Licorice Root, Maca, Maca Root, Maitake Mushroom, Marshmallow Root, Milk Thistle, Milk Thistle extract, Muira Puama, Muira Puama Root, Mullein Leaves, Myrrh, Myrrh Gum, Neem, Nettle Root, Nettle Root extract, Noni, Noni Fruit, Oregano oil, Grape Root, Alfalfa, St. John's Wort, Valerian Root, Parsley, Passion Flower, Pau D'Arco, Pau D'Arco inner bark, psyllium, psyllium husk, psyllium seeds, Stevia extract, Red Clover, Red Clover Blossoms, Red Raspberry Leaves, Red Root, Reishi mushroom, Rose hips, Rosemary extract, Safflower, Sarsaparilla Root, Senna leaves, Shiitake mushroom, Skullcap, Slippery Elm Bark, Spirulina, Stevia syrup, Suma, Uva Ursi, Vervain, Vitex, White Oak Bark, White Willow Bark, Wild Yam Root, Wood Betony, Yarrow, Yellow Dock, Yohimbe, Yohimbe Bark, Yohimbe Bark extract, Yucca, Co-enzyme Q10, Bovine Cartilage, Shark Cartilage, Garlic, Lysine, Mistletoe extract, Omega-3 fatty acids, S-Adenosyl-L-Methionine, Kava, Kava kava, Chapparal, Comfrey, Ma Huang, Germander, Lobelia, Magnolia, Stephania, Wormwood, Tryptophan, Andrographis, Pomegranate extract, Arjuna, Choline, Inositol, Lycopene, Pantothene (Pantethine), Pantothenic acid, Bioflavonoid, Acerola, Quercetin, Rutin, Bromelain, 5-HTP, 7-Keto DHEA, DHEA, lipoic acid, Argentine Liver Concentrate, beta-glucan, D-mannose, DMAE, gamma-oryzanol, glucosamine chondroitin, hyaluronic acid, Horny Goat Weed, L-glutamine, Grape Seed, MSM, glucosamine MSM, Oyster mushroom, Policosanol, Picolinic acid (Picolinate), Pyruvic acid (Pyruvate), Red Yeast Rice, Type II Collagen, Type I Collagen, Creatine, Nattokinase, hydrolyzed gelatin, Xylitol, Carnitine, Alpha-L-Carnitine, Chondroitin Sulfate, Colostrum, Cholestatin, Lactoferrin, Guggul, Lutein, Phosphatidylcholine, Phosphatidylserine, Soy extract, Tea Tree oil, Lecithin, Stinging Nettle, Eucalyptus, *Sambucous canadensis, Sambucous nigra, Camellia sinensis, Camellia thea, Camellia theifera, Thea sinensis, Thea bohea, Thea viridis*, Wild Cherry, curcumin, *Emblica officinalis*, eicosapentanoic acid, docosahexanoic acid, primrose oil, horseradish root, L-glutamine, antiscorbutic vitamin, cevitamic acid, membranous milk vetch, milk vetch, mongolian milk, moringa, yeast, dipeptides, tripeptides, and the like, and combinations thereof.

Examples of vitamins can include, but are not limited to, Vitamin A (retinol), carotenes such as beta-carotene, carotenoids, Vitamin $B_1$ (thiamin), Vitamin $B_2$ (riboflavin), Vitamin $B_3$ (niacin), Biotin, Vitamin $B_6$ (pyridoxine), Vitamin $B_{12}$ (cyanocobalamine), folic acid (folate), Vitamin C (ascorbic acid), Vitamin D, ergocalciferol, cholecalciferol, Vitamin E (tocopherol), Vitamin K, metabolites thereof, derivatives thereof known at the time of filing of this application (e.g., methylcobalamin, niacinamide, retinoids, tocotrienols, and the like), salts thereof (e.g., ascorbyl palmitate, tocopherol succinate, and the like), and combinations thereof.

Examples of minerals can include, but are in no way limited to, calcium, magnesium, iron, selenium, zinc, chromium, copper, manganese, cobalt, silver, vanadium, tin, silicon, nickel, boron, molybdenum, iodine, phosphorus, titanium, bismuth, aluminum, and the like, and any combination thereof.

The active agent, as well as any active or therapeutic agents present in the compositions according to the invention, can be present in their free base (i.e., pure or non-associated) form or in the form of a pharmaceutically acceptable salt. Depending on the nature of the active agent, suitable pharmaceutical salts may include, but are not limited to, hydrochloride, hydrobromide, hydroiodide, nitrate, sulfate, bisulfate, phosphate, acid phosphate, carbonate, bicarbonate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, pamoate (i.e., 1,1'-methylene-bis-(2-hydroxy-3-naphthoate)), or the like, or a combination thereof. Additionally or alternatively, the active agent may be present in the form of a sodium salt, potassium salt, ammonium salt, meglumine salt, TRIS salt, salt with a basic amino acid, or the like, or a combination thereof.

The invention also includes active agent compositions together with one or more non-toxic pharmaceutically acceptable carriers, adjuvants, or vehicles, collectively referred to as carriers, without intent to limit. The compositions and pharmaceutically acceptable carriers are formulated for transmucosal administration, preferably to the oral mucosa and more preferably to the buccal mucosa.

The compositions preferably comprise at least one active agent and are suitable for transmucosal administration, preferably to the oral mucosa and more preferably to the buccal mucosa. In illustrative embodiments of the invention, novel methods of transmucosal administration of at least one active agent and optionally additional therapeutic agents are described, and methods of using the same are taught.

The compositions of the various embodiments of the present invention can also include solubilizing agents, preferably solubilizing agents listed in the FDA Inactive Ingredients Guide (herein incorporated by reference in its entirety for all purposes). Examples of solubilizing agents include but are not limited to polyvinyl alcohol (PVA), polyoxyethylene sorbitan fatty acid esters such as Polysorbate 80 or Tween 80, and polyols such as glycerin.

The compositions of the various embodiments of the present invention can also include preservatives to inhibit or prevent microbial activity. Examples of suitable preservatives include but are not limited to Purite®, benzyl alcohol, and sodium benzoate. When ethanol is used in sufficient quantity as the polar solvent, the ethanol can also serve as a preservative.

In general, the rate of absorption of an active agent can increase depending on the mode of administration (e.g., transmucosal vs. conventional oral ingested or swallowed administration). In some disclosed methods of transmucosally administering compositions comprising active agents, efforts have been made to control the size and size range of particles of the pharmaceutical compositions of the invention. Active agent formulations suitable for transmucosal administration are preferably administered to the oral mucosa using, for example, a spray or mist.

Advantages of the transmucosal administration of active agent compositions of various embodiments of the invention, as compared to conventional oral or intravenous formulations include but are not limited to: (1) smaller dosage form size; (2) smaller doses of drug required to obtain the same pharmacological effect; (3) increased bioavailability; (4) substantially similar pharmacokinetic profiles of the compositions whether administered in the fed or fasted state; (5) improved pharmacokinetic profiles; (6) ease of administration for the administrator (professional or layperson); (7) the compositions can be used in conjunction with other active agents; (8) reduced stress or discomfort to the animal patient; (9) greater exposure of the delivered dosage vs. conventional oral ingested or swallowed administration; (10) ability to administer to an unconscious animal; and (11) ease of administration vs. oral gavage or balling gun, particularly in large animals.

Transmucosal administration of the active agent compositions of the invention preferably exhibits increased bioavailability, requires smaller doses, and exhibits shorter time to reach maximum plasma concentration after administration as compared to prior conventional active agent formulations (e.g., conventional oral administration). In one illustrative embodiment, greater bioavailability due to transmucosal administration of the active agent compositions of the invention can enable a smaller dosage size to achieve the same therapeutic or prophylactic effect. This is particularly significant for animal populations such as domestic animals that may require repeated treatment or treatment of an entire herd or population. In another illustrative embodiment of the invention, transmucosal administration of active agent compositions provides enhanced bioavailability such that the active agent dosage can be reduced, resulting in a potential decrease in the risk of toxicity associated with such active agents. It has been surprisingly found in the invention that methods of transmucosal administration of active agent compositions can permit therapeutic and prophylactic levels at desirably lower dosage than conventional methods of administration.

The invention also preferably provides methods of transmucosal administration of active agent compositions having a desirable pharmacokinetic profile when administered to animals. The desirable pharmacokinetic profile of the active agent compositions preferably includes, but is not limited to: (1) the $T_{max}$ of an active agent, when assayed in the plasma of an animal following transmucosal administration, is preferably less than the $T_{max}$ for a conventional form (i.e., a pill) of the same active agent, administered at the same dosage; (2) the $C_{max}$ of an active agent, when assayed in the plasma of an animal following transmucosal administration, is preferably greater than the $C_{max}$ for a conventional form (i.e., a pill) of the same active agent, administered at the same dosage; and/or (3) that the AUC of an active agent, when assayed in the plasma of an animal following transmucosal administration, is preferably greater than the AUC for a conventional form (i.e., a pill) of the same active agent, administered at the same dosage.

The desirable pharmacokinetic profile, as used herein, is the pharmacokinetic profile measured after the initial transmucosal administration of a dose of an active agent. The compositions can be formulated in the manner described below and using methods known to those of skill in the art.

A preferred active agent transmucosal composition of the invention may exhibit in comparative pharmacokinetic testing with a non-transmucosal formulation of the same active agent, administered at the same dosage, a $T_{max}$ not greater than about 90%, not greater than about 80%, not greater than about 70%, not greater than about 60%, not greater than about 50%, not greater than about 30%, not greater than about 25%, not greater than about 20%, not greater than about 15%, or not greater than about 10%, of the $T_{max}$ exhibited by the non-transmucosal formulation of the same active agent. The range of $T_{max}$ values of an active agent transmucosal composition of the invention may exhibit in comparative pharmacokinetic testing with a non-transmucosal formulation of the same active agent, administered at the same dosage can be 10%-90% of the $T_{max}$ exhibited by the non-transmucosal formulation of the same active agent, inclusive of all the subranges therebetween (e.g., 10%-80%, 20%-90%, 50%-70%, etc.).

A preferred active agent transmucosal composition of the invention may also exhibit in comparative pharmacokinetic testing with a non-transmucosal formulation of the same active agent, administered at the same dosage, a $C_{max}$ which is at least about 10%, at least about 20%, at least about 30%, at least about 40%, at least about 50%, at least about 60%, at least about 70%, at least about 80%, at least about 90%, at least about 100%, about 500%, or about 1000% greater than the $C_{max}$ exhibited by the non-transmucosal formulation of the same active agent. The range of $C_{max}$ values of an active agent transmucosal composition of the invention may exhibit in comparative pharmacokinetic testing with a non-transmucosal formulation of the same active agent, administered at the same dosage can be 10%-90% of the $C_{max}$ exhibited by the non-transmucosal formulation of the same active agent, inclusive of all the subranges therebetween (e.g., 10%-80%, 20%-90%, 50%-70%, etc.).

A preferred active agent transmucosal composition of the invention may also exhibit in comparative pharmacokinetic testing with a non-transmucosal formulation of the same active agent, administered at the same dosage, an AUC which is at least about 10%, at least about 20%, at least about 30%, at least about 40%, at least about 50%, at least about 60%, at least about 70%, at least about 80%, at least about 90%, at least about 100%, about 500%, or about 1000% greater than the AUC exhibited by the non-transmucosal formulation of the same active agent. The range of AUC values of an active agent transmucosal composition of the invention may also exhibit in comparative pharmacokinetic testing with a non-transmucosal formulation of the same active agent, administered at the same dosage can be 10% to about 1000% of the AUC exhibited by the non-transmucosal formulation of the same active agent, inclusive of all the subranges therebetween (e.g., 20% to about 1000%, 50% to about 500%, 500% to about 1000%, etc.).

Any dosage form of transmucosal composition giving the desired pharmacokinetic profile is suitable for administration to the oral mucosa according to the present methods. Exemplary dosage forms of transmucosal formulations giving such profiles are liquid dispersions, aerosols, pump sprays, or mists of an active agent composition. The transmucosal composition of the invention preferably is a liquid mist dosage form, although any pharmaceutically acceptable dosage form for transmucosal administration to the oral mucosa of an animal can be utilized.

The active agent compositions of the invention can also be transmucosally administered in combination with an additional therapeutic agent, for example, one or more other drugs, penetration enhancers, bioadhesive agents, flavoring agents, masking agents, or the like, as further described herein.

Transmucosal administration of non-steroidal anti-inflammatory agent compositions of the invention are useful in methods of treating or preventing pain, inflammation, and/or fever, as further described herein. Transmucosal administration of antihistamine agent compositions of the invention are useful in methods of treating or preventing allergic reactions or conditions as further described herein. Transmucosal administration of cardiovascular compositions of the invention are useful in methods of treating or preventing abnormal/irregular heartbeat, weakness, shortness of breath, reduced exercise tolerance, lethargy, syncope, hypoxia, pulmonary edema, ascites, high blood pressure, and/or loss of consciousness, or the like, as further described herein. Transmucosal administration of hormone compositions of the invention are useful in methods of treating or preventing decreased or non-existent production of the particular hormone, as further described herein. Transmucosal administration of immunosuppressive agent compositions of the invention are useful in methods of treating or preventing enhanced or overactive immune responses, as further described herein. Transmucosal administration of nutraceutical compositions of the invention are useful in methods of treating or preventing decreased or non-existent production or dietary intake of the particular nutraceutical, as further described herein. Transmucosal administration of sedative/tranquilizer/behavior modifying agent compositions of the invention are useful in methods of treating or preventing insomnia, stress, separation anxiety, and/or hyperactivity, or the like, as further described herein. Transmucosal administration of antibiotic compositions of the invention are useful in methods of treating or preventing bacterial infections, or the like, as further described herein. Transmucosal administration of anti-emetic compositions of the invention are useful in methods of treating or preventing nausea and vomiting, or the like, as further described herein.

D. Therapeutic/Prophylactic Administration and Compositions

Due to the potential increased bioavailability and potential lower dose or other advantage resulting from transmucosal administration of compositions of the invention, the compositions are advantageously useful in veterinary medicine. As described herein, the methods of transmucosal administration of compositions of the invention are useful for the treatment or prevention of various conditions, illnesses, or disorders as described herein.

The compositions, which comprise one or more active agents of the invention, are administered transmucosally, preferably to the oral mucosa, and more preferably to the buccal or gingival mucosa. The compositions of the invention can be administered by any convenient route, for example, by absorption through epithelial or mucocutaneous linings (e.g., oral mucosa or buccal mucosa) and may be administered together with an additional therapeutic agent. Various delivery systems are known that can be used to administer an active agent of the invention. Methods of administration include, but are not limited to, transmucosal administration, particularly to the oral mucosa, preferably to the buccal mucosa, for example, using a pump spray or aerosol spray. The preferred mode of administration can be left to the discretion of the practitioner, and may depend in part upon the specific type of the medical conditions of interest. In most instances, administration will result in the release of the active agents of the invention into the bloodstream.

The methods of transmucosal administration of a composition comprising active agents of the invention may be assayed in vitro and/or in vivo, for the desired therapeutic or prophylactic activity. For example, in vitro assays can be used to determine whether administration of a specific agent of the invention or a combination of active agents of the invention is preferred. The active agents of the invention may also be demonstrated to be effective and safe using laboratory animal model systems. Such in vitro and in vivo assays are known in the art.

The compositions will contain a therapeutically or prophylactically effective amount of an active agent of the invention, optionally more than one active agent of the invention (or salts, solvates, or derivatives thereof), preferably in purified form, together with a suitable amount of a pharmaceutically acceptable vehicle so as to provide the form for transmucosal administration to the animal.

The compositions to be used in the methods of the invention can take the form of solutions, suspensions, emulsions, aerosols, dry powders or particulates, sprays, mists, capsules, or any other form suitable for use in transmucosally administering a drug to the oral mucosa, preferably the buccal mucosa of an animal. In one embodiment, the pharmaceutically acceptable vehicle is a transmucosal oral spray (see, e.g., U.S. Pat. No. 6,676,931, which is incorporated herein by reference). Other examples of suitable pharmaceutical vehicles are described in "Remington's Pharmaceutical Sciences" by E. W. Martin, which is also incorporated herein by reference.

In an illustrative embodiment, the active agents of the invention are formulated in accordance with routine procedures as a pharmaceutical composition adapted for transmucosal administration to the oral mucosa of an animal. Typically, compositions of the invention for transmucosal administration are solutions in sterile isotonic aqueous alcohol buffer. Optionally, the compositions may also include a flavoring agent. Generally, the ingredients are supplied either separately or mixed together in unit dosage form, for example, as an aerosol spray or pump spray indicating the quantity of active agent. The optional flavoring agents include, for example, natural or synthetic animal flavoring or flavor enhancement agents, agents that improve the palatability or odor of the compositions to an animal, and preserving agents, to provide a pharmaceutically palatable preparation. For example, the flavorants that may be used include, but are not limited to, liver, chicken, beef, or bacon flavorants. In some instances, the compositions of the invention may be formulated to comprise species specific agents such as: liver, beef, chicken, cheese, or honey for dogs; fish, tuna, sardine or cod liver oil for cats; apple, apple/caramel, clover or honey for horses; eggnog, anise, alfalfa or maple for cattle; lemon-custard or banana cream for reptiles; chocolate or peanut butter for ferrets; carrot, celery or lettuce for rabbits; and tutti-frutti, pina-colada or tangerine for birds.

The compositions of the various embodiments of the present invention can also include sweeteners to improve the palatability of the compositions. Examples of suitable sweeteners include but are not limited to sucralose (commercially available as Splenda), sucrose, neotame, and acesulfamate K.

The amount of an active agent of the invention that will be effective in the treatment of a particular disorder, disease, or condition disclosed herein can often depend on the nature of the disorder, disease, or condition, and can be determined by standard clinical techniques. In addition, in vitro or in vivo assays may optionally be employed to help identify optimal dosage ranges. The precise dose to be employed in the compositions may also depend on the route of administration and the seriousness of the disease, disorder, or condition and on the animal being treated, and should be decided according to the judgment of the practitioner and each animal's particular circumstances.

The dosage amounts described herein refer to total amounts administered; that is, if more than one agent of the invention is administered, the preferred dosages correspond to the total amount of each agent administered. Oral compositions typically contain about 10% to about 95% active ingredient by weight.

i. Aerosol Sprays

In an illustrative embodiment, the invention encompasses transmucosal administration of a composition of the invention to the oral mucosa using an aerosol spray. The aerosol sprays comprise one or more active agents in the form of a suspension, emulsion, or solution and can be used for the transmucosal delivery of the active agents. One particular application comprises pharmaceutical suspensions for transmucosal administration of an active agent in particulate form.

A particular embodiment encompasses a metered dose aerosol spray conventionally consisting of a pressurized container which has a metering valve of fixed volume to measure individual doses of a suspension of medicament held in the container to be administered to the oral mucosa. For example, for convenience for veterinary use, an aerosol spray can contain a metered dose that will allow accurate application of a therapeutically or prophylactically effective amount of an active agent for each animal type, for instance, a dog, cat, or horse. Further the dosages can be metered for a specific size of an individual animal. For instance, metered doses may be prepared for large (greater than about 50-pound) or small (less than about 25-pound) dogs. In order to ensure the transmucosal administration of an accurate dose of active agent, it is essential that the suspension be consistently and homogeneously dispersed and that the valve performance is reproducible and effective throughout the life of the container. The suspension conventionally comprises active agent particles dispersed in a liquefied gas, which in use acts as a propellant. On depressing the valve stem of the metering valve, the propellant fraction of the metered dose rapidly vaporizes, so as to aerosolize the suspended particulate active agent, which is then administered to the oral mucosa.

To administer a transmucosal oral mist, the commissure of the animal's (e.g., dog's, cat's, or horse's) lips will be grasped and pulled away from the gums opening the buccal space. The mist is typically directed caudally and towards the gingival and/or buccal mucosal surfaces. The mist head will be depressed fully, ensuring no mist escapes from the mouth. If the dose is greater than about 300 to about 500 microliters, the dose may be split between both sides of the mouth.

Traditionally, chlorofluorocarbons such as CFC-11, CFC-12, and CFC-114 have been employed as propellants in metered dose inhalers. A particulate medicament intended for transmucosal administration may have a particle size with a median aerodynamic diameter from about 0.05 μm to about 11 μm. Particles between about 0.05 μm and about 11 μm can possess a high surface energy and can therefore be difficult to disperse initially in the propellant, and, once dispersed, can exhibit a tendency to aggregate undesirably and rapidly, leading eventually to irreversible aggregation of the particles. In the case of using a CFC as a propellant, this problem was overcome by the addition of a surfactant soluble in the CFC in order to coat the medicament particles and to prevent aggregation by steric hindrance. The presence of surfactant is also believed to be an aid to valve performance. In practice, medicament particles are homogenized in the liquid propellant with the inclusion of a propellant soluble surfactant, e.g., such as lecithin, oleic acid, or sorbitan trioleate. The resulting bulk suspension is then dispensed into individual metered dose inhalers and a high vapor pressure propellant added.

Alternative propellants, which share some similar physical properties to those of previously used CFC propellants and which have been suggested for use in metered dose inhalers, are hydrofluoroalkanes, notably HFA-134a and HFA-227. The propellant is typically non-Freon material, preferably a linear or branched ($C_3$-$C_8$) hydrocarbon. The propellant should be substantially non-aqueous and can produce a pressure in the aerosol container such that, under expected normal usage, a sufficient pressure to expel the solvent from the container is produced when the valve is activated, but not excessive pressure such as to damage the container or valve seals.

In a particular embodiment, the aerosol spray compositions of the invention, for transmucosal administration of a pharmacologically active agent soluble in a pharmacologically acceptable non-polar solvent comprise in weight % of total composition: pharmaceutically acceptable propellant from about 5 to about 80%, non-polar solvent from about 19 to about 85%, active agent from about 0.05 to about 50%, suitably additionally comprising, by weight of total composition, an optional flavoring or odor enhancement agent from about 0.01 to about 10% (when present). In one embodiment the composition comprises: (a) propellant from about 10 to about 70%, non-polar solvent from about 25 to about 89.9%, active agent from about 0.01 to about 40%, and an optional flavoring or odor enhancement agent or agents from about 0.01 to about 8% (when present); or (b) propellant from about 20 to about 70%, non-polar solvent from about 25 to about 74.75%, active agent from about 0.25 to about 35%, and an optional flavoring or odor enhancement agent or agents from about 0.02 to about 7.5% (when present).

Another particular embodiment of the invention comprises a polar aerosol spray composition for transmucosal administration of a pharmacologically active agent soluble in a pharmacologically acceptable polar solvent, which is also administrable in aerosol form driven by a propellant. In this case, the composition comprises in weight % of total composition: aqueous polar solvent from about 10 to about 99%, active agent from about 0.1 to about 25%, suitably additionally comprising, by weight of total composition, an optional flavoring or odor enhancement agent or agents from about 0.01 to about 10% (when present) and propellant from about 2 to about 10%.

In another embodiment, the composition comprises (in weight % of total composition): (1) aqueous polar solvent from about 20 to about 99%, active agent from about 0.01 to about 15%, an optional flavoring or odor enhancement agent or agents from about 0.1 to about 5% (when present), and propellant from about 2 to about 5%; or (2) aqueous polar solvent from about 25 to about 99%, active agent from about 0.2 to about 25%, an optional flavoring or odor enhancement agent or agents from about 0.02 to about 2.5% (when present), and propellant from about 2 to about 4%.

Another particular embodiment of the invention encompasses a sealed aerosol spray container containing a composition of the non polar or polar aerosol spray formulation, and a metered valve suitable for releasing from said container a predetermined amount of said composition.

The non-polar or polar solvents must dissolve the active agent and be miscible with the propellant, (i.e., solvent and propellant must form a single phase at a temperature between about 0 and about 40° C. and at a pressure range between about 1 and about 3 atm).

The polar and non-polar aerosol spray compositions of the invention are intended to be administered from a sealed, pressurized container. Unlike a pump spray, which allows the entry of air into the container after every activation, the aerosol container of the invention is sealed at the time of manufacture. The contents of the container are released by activation of a metered valve, which does not allow entry of atmospheric gasses with each activation. Such containers are commercially available.

ii. Pump Sprays

Another embodiment of the invention encompasses a pump spray container containing a composition for transmucosal administration of the pump spray formulation, and a metered valve suitable for releasing from said container a predetermined amount of said composition.

In a particular embodiment, the pump spray composition of the present invention, (i.e., propellant free composition), for transmucosal administration of an active agent, wherein said active agent is soluble in a pharmacologically acceptable non-polar solvent comprises in weight % of total composition: aqueous non-polar solvent from about 30 to about 99.69%, active agent from about 0.005 to about 55%, and suitably additionally, an optional flavoring agent or agents from about 0.1 to about 10% (when present).

Another particular embodiment encompasses a polar pump spray composition of the present invention, (i.e., propellant free composition), for transmucosal administration of a pharmacologically active agent soluble in a pharmacologically acceptable polar solvent comprises in weight % of total composition: aqueous polar solvent from about 30 to about 99.69%, active agent from about 0.001 to about 60%, suitably additionally comprising, by weight of total composition, an optional flavoring agent or agents from about 0.1 to about 10% (when present). Preferably the composition comprises: (a) an aqueous polar solvent from about 37 to about 98.8%, active agent from about 0.005 to about 55%, and an optional flavoring agent from about 0.5 to about 8% (when present); or (b) an aqueous polar solvent from about 60.9 to about 98.8%, active agent from about 0.01 to about 40%, and an optional flavoring agent from about 0.75 to about 7.5% (when present).

In another embodiment, the composition comprises: (a) an aqueous polar solvent from about 70 to about 99%, and active agent from about 0.01 to about 1.0%; or (b) an aqueous polar solvent from about 80 to about 99%, and an active agent from about 0.1 to about 0.5%. In yet another embodiment, the polar solvent of the composition comprises 7.5 to 20% ethanol, preferably 7.5 to 15% ethanol in water.

iii. Doses and Compositions

The dosage amounts described herein refer to total amounts administered; that is, if more than one agent of the invention is administered, the preferred dosages correspond to the total amount of each agent administered. Oral compositions typically contain about 10% to about 95% active ingredient by weight.

Anti-Inflammatory Agent

One embodiment of the invention encompasses methods of treatment or prophylaxis by transmucosal administration to the oral mucosa of an animal, in need thereof, of a therapeutically or prophylactically effective amount of a composition comprising a non-steroidal anti-inflammatory agent of the invention. A preferred non-steroidal anti-inflammatory agent is meloxicam or a pharmaceutically acceptable salt, solvate or ester thereof.

Suitable dosage ranges for transmucosal administration to the oral mucosa are generally from about 0.001 milligram to about 200 milligrams of a non-steroidal anti-inflammatory agent of the invention per kilogram body weight. In specific preferred embodiments of the invention, the oral dose of non-steroidal anti-inflammatory agent is from about 0.005 milligram to about 100 milligrams per kilogram body weight, more preferably from about 0.01 milligram to about 50 milligrams per kilogram body weight, more preferably from about 0.03 milligram to about 20 milligrams per kilogram body weight, and yet more preferably from about 0.05 milligram to about 5 milligrams per kilogram body weight. In a most preferred embodiment, the oral dose is about 0.1 milligrams of a non-steroidal anti-inflammatory agent of the invention per kilogram body weight.

The compositions according to the invention can be utilized in animals for treating arthritis, for treating acute inflammation, in post-surgical situations, in treating colic, or in any situation where pain relief is desired. In addition, non-steroidal anti-inflammatory agent compositions according to the invention, that are also known selective COX-2 inhibitors in humans (e.g., meloxicam), may be used to treat diseases, conditions, or disorders in animals where selective COX-2 inhibition would be desirable and/or therapeutically effective.

Antihistamine

Suitable dosage ranges for transmucosal administration to the oral mucosa are generally from about 0.001 milligram to about 200 milligrams of an antihistamine agent of the invention per kilogram body weight. In specific preferred embodiments of the invention, the oral dose of antihistamine agent is from about 0.01 milligram to about 70 milligrams per kilogram body weight, more preferably from about 0.1 milligram to about 50 milligrams per kilogram body weight, more preferably from about 0.5 milligram to about 20 milligrams per kilogram body weight, and yet more preferably from about 1 milligram to about 10 milligrams per kilogram body weight. In a most preferred embodiment, the oral dose is about 5 milligrams of an antihistamine agent of the invention per kilogram body weight.

In specific preferred embodiments of the invention, the oral dose of antihistamine agent is from about 0.01 milligram to about 70 milligrams per kilogram body weight, more preferably from about 0.1 milligram to about 50 milligrams per kilogram body weight, more preferably from about 0.5 milligram to about 20 milligrams per kilogram body weight, and yet more preferably from about 1 milligram to about 10 milligrams per kilogram body weight. In a most preferred embodiment, the oral dose is about 5 milligrams of an antihistamine agent of the invention per kilogram body weight.

Cardiovascular Agent

Suitable dosage ranges for transmucosal administration to the oral mucosa are generally from about 0.001 milligram to about 200 milligrams of a cardiovascular agent of the invention, for example a cardiac glycoside, per kilogram body weight. In specific preferred embodiments of the invention, the oral dose of cardiovascular agent is from about 0.005 milligram to about 175 milligrams per kilogram body weight, more preferably from about 0.01 milligram to about 150 milligrams per kilogram body weight, more preferably from about 0.02 milligram to about 100 milligrams per kilogram body weight, for example from about 0.05 milligram to about 50 milligrams per kilogram body weight. In a preferred embodiment, the oral dose is from about 0.1 milligrams to about 25 milligrams of a cardiovascular agent of the invention per kilogram body weight.

In specific preferred embodiments of the invention, the oral dose of cardiovascular agent is from about 0.005 milligram to about 175 milligrams per kilogram body weight, more preferably from about 0.01 milligram to about 150 milligrams per kilogram body weight, more preferably from about 0.02 milligram to about 100 milligrams per kilogram body weight, for example from about 0.05 milligram to about 50 milligrams per kilogram body weight. In a preferred embodiment, the oral dose is from about 0.1 milligrams to about 25 milligrams of a cardiovascular agent of the invention per kilogram body weight.

Hormone

Suitable dosage ranges for transmucosal administration to the oral mucosa are generally from about 0.001 milligram to about 200 milligrams of a hormone of the invention per kilogram body weight. In specific preferred embodiments of the invention, the oral dose of hormone is from about 0.002 milligram to about 100 milligrams per kilogram body weight, more preferably from about 0.003 milligram to about 50 milligrams per kilogram body weight, more preferably from about 0.004 milligram to about 20 milligrams per kilogram body weight, and yet more preferably from about 0.005 milligram to about 5 milligrams per kilogram body weight. In a most preferred embodiment, the oral dose is from about 0.01 milligrams to about 0.5 milligram of a hormone of the invention per kilogram body weight.

In specific preferred embodiments of the invention, the oral dose of hormone is from about 0.002 milligram to about 100 milligrams per kilogram body weight, more preferably from about 0.003 milligram to about 50 milligrams per kilogram body weight, more preferably from about 0.004 milligram to about 20 milligrams per kilogram body weight, and yet more preferably from about 0.005 milligram to about 5 milligrams per kilogram body weight. In a most preferred embodiment, the oral dose is from about 0.01 milligrams to about 0.5 milligram of a hormone of the invention per kilogram body weight.

Immunosuppressive Agent

Suitable dosage ranges for transmucosal administration to the oral mucosa are generally from about 0.001 milligram to about 200 milligrams of an immunosuppressive agent of the invention per kilogram body weight. In specific preferred embodiments of the invention, the oral dose of immunosuppressive agent is from about 0.005 milligram to about 100 milligrams per kilogram body weight, more preferably from about 0.01 milligram to about 50 milligrams per kilogram body weight, more preferably from about 0.03 milligram to about 20 milligrams per kilogram body weight, and yet more preferably from about 0.05 milligram to about 5 milligrams per kilogram body weight. In a most preferred embodiment, the oral dose is from about 0.1 milligrams to about 1 milligram of an immunosuppressive agent of the invention per kilogram body weight.

In specific preferred embodiments of the invention, the oral dose of immunosuppressive agent is from about 0.005 milligram to about 100 milligrams per kilogram body weight, more preferably from about 0.01 milligram to about 50 milligrams per kilogram body weight, more preferably from about 0.03 milligram to about 20 milligrams per kilogram body weight, and yet more preferably from about 0.05 milligram to about 5 milligrams per kilogram body weight. In a most preferred embodiment, the oral dose is from about 0.1 milligrams to about 1 milligram of an immunosuppressive agent of the invention per kilogram body weight.

Nutraceutical, Vitamin, and/or Mineral

Suitable dosage ranges for transmucosal administration to the oral mucosa are generally from about 0.001 milligram to about 200 milligrams of a nutraceutical of the invention per kilogram body weight. In specific preferred embodiments of the invention, the oral dose of nutraceutical is from about 0.005 milligram to about 150 milligrams per kilogram body weight, more preferably from about 0.01 milligram to about 125 milligrams per kilogram body weight, more preferably from about 0.02 milligram to about 100 milligrams per kilogram body weight, and yet more preferably from about 0.05 milligram to about 75 milligrams per kilogram body weight. In some embodiments, the oral dose is from about 0.1 milligrams to about 50 milligrams of a nutraceutical of the invention per kilogram body weight.

In specific preferred embodiments of the invention, the oral dose of nutraceutical is from about 0.005 milligram to about 150 milligrams per kilogram body weight, more preferably from about 0.01 milligram to about 125 milligrams per kilogram body weight, more preferably from about 0.02 milligram to about 100 milligrams per kilogram body weight, and yet more preferably from about 0.05 milligram to about 75 milligrams per kilogram body weight. In some embodiments, the oral dose is from about 0.1 milligrams to about 50 milligrams of a nutraceutical of the invention per kilogram body weight.

Sedative/Tranquilizer/Behavior Modifying Agent

Suitable dosage ranges for transmucosal administration to the oral mucosa are generally from about 0.001 milligram to about 200 milligrams of a sleeping aid agent of the invention per kilogram body weight. In specific preferred embodiments of the invention, the oral dose of sleeping aid agent is from about 0.005 milligram to about 150 milligrams per kilogram body weight, more preferably from about 0.01 milligram to about 100 milligrams per kilogram body weight, more preferably from about 0.05 milligram to about 50 milligrams per kilogram body weight, for example from about 0.1 milligram to about 25 milligrams per kilogram body weight. In a most preferred embodiment, the oral dose is from about 0.2 milligrams to about 10 milligrams of a sleeping aid agent of the invention per kilogram body weight.

In specific preferred embodiments of the invention, the oral dose of sedative/tranquilizer/behavior modifying agent is from about 0.005 milligram to about 150 milligrams per kilogram body weight, more preferably from about 0.01 milligram to about 100 milligrams per kilogram body weight, more preferably from about 0.05 milligram to about 50 milligrams per kilogram body weight, for example from about 0.1 milligram to about 25 milligrams per kilogram body weight. In a most preferred embodiment, the oral dose is from about 0.2 milligrams to about 10 milligrams of a sedative/tranquilizer/behavior modifying agent of the invention per kilogram body weight.

Antiparasitic Agent

Antiparasitic agents of the invention include any agent capable of therapeutically or prophylactically treating the presence of an ecto or endo parasite in animal. Preferred antiparasitic agents include, but are not limited to, endoparasiticidal agents, ectoparaciticidal agent, and endectoparaciticidal agent. In a particular embodiment, the antiparasitic agent is an avermectin, milbemycin, phenylpyrazole, nodulisporic acid, clorsulon, closantel, paraherquamide, quinacrine, chloroquine, vidarabine, nitenpyram, ivermectin, milbemycine oxime, lufenuron, salimectin, moxidectin, or dorimectin. In a more particular embodiment, the antiparasitic agent is nitenpyram, ivermectin, milbemycine oxime, lufenuron, salimectin, moxidectin, or dorimectin.

The antiparasitic agent is present in an amount of from about 0.001 to about 80 percent by weight of the total composition. In another illustrative embodiment, the pharmaceutically acceptable carrier in an amount from about 20 to about 99.999 percent by weight of the total composition. In another illustrative embodiment, the composition comprises a flavoring agent in an amount from about 0.1 to about 10 percent by weight of the total composition. In another illustrative embodiment, the pharmaceutically acceptable carrier is present in an amount from about 30 to about 95 percent by weight of the total composition, the antiparasitic agent is present in an amount from about 0.005 to about 55 percent by weight of the total composition, and the flavoring agent is present in an amount from about 0.5 to about 8 percent by weight of the total composition.

In a particular embodiment, the invention encompasses a composition for transmucosal administration comprising an antiparasitic agent in an amount of from about 0.1 to about 25 percent by weight of the total composition; a polar or nonpolar solvent in an amount from about 10 to about 97 percent by weight of the total composition; and a flavoring agent in an amount from about 0.05 to about 10 percent by weight of the total composition.

Transmucosal oral mists have activity on endoparasites (internal parasites), ectoparasites (external parasites) and in some cases both internal and external parasites (endectoparasiticides). In the case of ectoparasite (external) parasite control, the formulated transmucosal mists control adult fleas on pets and break the flea life-cycle by inhibiting insect development. Specifically, lufenuron inhibits flea egg development and nitenpyram kills adult fleas. The transmucosal delivery enables a more rapid on-set of action than tablets and results in faster flea kill for ectoparasitical agents and endectoparasiticidal agents. In the case of endoparasite (internal) control, the formulated transmucosal mists controls various parasites. In the case of milbemycine oxime, the transmucosal oral mist controls heartworm disease caused by *dirofilaria immitis*, control of adult hookworm (ancylostoma caninum) and the removal and control of adult roundworms (*toxacara canis, toxascaris leonina*, and whipworms (*trichuris vulpis*) in canine and in feline, specifically, control of heartworm disease (*dirofilaria immitis*), removal of adult roundworms (*toxacara cati*) and adult hooworm (*ancylostome tubaeforme*). Capstar delivered by transmucosal oral mist in the canine controls adult fleas. Lufenuron administered by transmucosal oral mist prevents flea eggs and larvae from developing. Selamectin administered by transmucosal oral mist in the canine kills adult fleas (*ctenocephalides felis*), heartworm disease (*dirofialria immitis*), treatment and controls ear mite infestations (*otodectes cyanotis*) and other important ectoparasites. In the case of ivermectin and moxidectin administered by transmucosal oral mist in the canine controls heartworm disease and internal parasites. Avermectins including ivemectin, moxidectin, doramectin and abamectin administered by transmucosal oral mist to equine, bovine and ovine subjects controls economically important parasites both internal and external, which affect the health and performance of the animal.

In one illustrative embodiment, the compositions of the invention for transmucosal administration of an antiparasitic compound soluble in a pharmacologically acceptable nonpolar solvent can comprise in weight % of total composition: pharmaceutically acceptable propellant about 5-80%, nonpolar solvent about 19-85%, antiparasitic compound about 0.05-50%, suitably optionally additionally comprising, by weight of total composition a flavoring agent about 0.01-10%. Preferably the composition comprises: propellant about 10-70%, non-polar solvent about 25-89.9%, active compound about 0.01-40%, flavoring agent about 1-8%; most suitably propellant about 20-70%, non-polar solvent about 25-74.75%, active compound about 0.25-35%, flavoring agent about 2-7.5%.

The compositions of the various embodiments of the present invention for transmucosal administration of an antiparasitic compound soluble in a pharmacologically acceptable polar solvent are also administrable in aerosol form driven by a propellant. In this case, the composition comprises in weight % of total composition: aqueous polar solvent about 10-97%, active compound about 0.1-25%, suitably additionally comprising, by weight of total composition a flavoring agent about 0.05-10% and propellant: about 2-10%. Preferably the composition comprises: polar solvent about 20-97%, active compound about 0.1-15%, flavoring agent about 0.1-5% and propellant about 2-5%; most suitably polar solvent about 2597 active compound about 0.2-25%, flavoring agent about 0.1-2.5% and propellant about 2-4%.

The compositions of the various embodiments of the present invention may be administered using a propellant free pump for transmucosal administration of a antiparasitic compound wherein said active compound is soluble in a pharmacologically acceptable non-polar solvent comprises in weight % of total composition: non-polar solvent about 30-99.99%, active compound about 0.005-55%, and suitably additionally, flavoring agent about 0.1-10%.

The transmucosal compositions of the various embodiments of the invention can also be administered with a pump, (e.g., the propellant free composition). For transmucosal administration of a pharmacologically antiparasitic compound soluble in a pharmacologically acceptable polar solvent comprises in weight % of total composition: aqueous polar solvent about 30-99.69%, active compound about 0.001-60%, suitably additionally comprising, by weight of total composition a flavoring agent about 0.1-10%. Preferably the composition comprises: polar solvent about 37-98.58%, active compound about 0.005-55%, flavoring agent about 0.5-8%; most suitably polar solvent about 60.9-97.06%, active compound about 0.01-40%, flavoring agent about 0.75-7.5%.

In one embodiment, administration of a transmucosal composition can be provided in a single application to the animal. That is, the intended dose is applied by, for example, applying a single spray comprising the intended volume and concentration of active agent to the oral mucosa of the animal, thereby providing the proper amount of active agent suitable for treating the animal. In another embodiment, larger animals requiring higher doses of active agent can be treated by repeated applications (i.e., multiple sprays each having a defined spray volume of a composition having a defined concentration of active agent). The repeated application to the oral mucosa of an animal may be carried out within a short period of time (i.e., each additional spray being carried out immediately after the preceding spray), or each application may be separated in time (i.e., minutes or hours) from the preceding spray, depending on the intended release profile of the active agent into the animal.

E. Combination Therapy

In certain embodiments of the present invention, the active agents of the invention can be used in combination therapy with at least one additional therapeutic agent. The active agent of the invention and the additional therapeutic agent can act additively or, more preferably, synergistically. In a preferred embodiment, a composition comprising an active agent of the invention is administered concurrently with the administration of another therapeutic agent, which can be part of the same composition as the active agent of the invention or a different composition. In another embodiment, a composition comprising a active agent of the invention is administered prior or subsequent to administration of an additional therapeutic agent. In addition, the additional therapeutic agent can be a active agent of the invention. Thus, a combination therapy according to the present invention can include combinations of two or more (e.g., two, three, four or more) active agents. For example, the combination therapy can include two or more antihistamines, and antihistamine and an anti-emetic agent, etc.

In another embodiment, the compositions of the invention encompasses administration of an active agent of the invention with a second therapeutic agent. Non-limiting examples of the second therapeutic agent include an anti-muscle spasm agent, anti-spasmodic, bone resorption inhibitor, smooth muscle contractile agent, calcium absorption enhancer, muscle relaxant, or a mixture thereof.

In another embodiment, the second therapeutic agent is an agent for treating urinary incontinence. Suitable agents for treating urinary incontinence for transmucosal administration include, but are not limited to, darifenacin, vamicamide, detrol, ditropan, imipramine, and mixtures thereof.

In another embodiment, the second therapeutic agent is an anti-diarrheal agent. Suitable anti-diarrheal agents for transmucosal administration include, but are not limited to, ondansetron, palnosetron, tropisetron, attapulgite, atropine, bismuth, diphenoxylate, loperamide, and mixtures thereof.

In another embodiment, the second therapeutic agent is an agent for treating nausea and/or vomiting. Suitable agents for treating nausea and/or vomiting for transmucosal administration include, but are not limited to, alosetron, dolasetron, granisetron, meclizine, metoclopramide, ondansetron, palnosetron, prochloperazine, promethazine, trimethobenzamiode, tropisetron, and mixtures thereof.

In another embodiment, the second therapeutic agent is an opioid. Suitable opioids for transmucosal administration include, but are not limited to, alfentanil, butorphanol, codeine, dezocine, fentanyl, hydrocodone, hydromorphone, levorphanol, meperidine, methadone, morphine, nalbuphine, oxycodone, oxymorphone, propoxyphene, pentazocine, sufentanil, tramadol, and mixtures thereof.

In another embodiment, the second therapeutic agent is an anti-bacterial agent. Suitable anti-bacterial agents for transmucosal administration include, but are not limited to, aminoglycoside, azole, cephalosporin, chlorhexidine, GAR-936, metronidazole, pazufloaxacin, penem, penicillin, rifapentene, sulfabenzamide, sulfacetamide, sulfathiazole, teicolplanin, telithromycin, enrofloxacin and mixtures thereof.

In another embodiment, the second therapeutic agent is an agent for treating a fungal infection. Suitable agents for treating fungal infections for transmucosal administration include, but are not limited to, voriconazole, griseofulvin, and mixtures thereof.

In another embodiment, the second therapeutic agent is a sedative. Suitable sedatives for transmucosal administration include, but are not limited to, dexmedetomidine, eszopiclone, indiplon, zolpidem, and zaleplon.

In another embodiment, the active agent is an antihistamine, immunosuppressive, anti-emetic, antibiotic, or antiparasitic agent administered in combination with a steroid. Non-limiting examples of such combinations include an antihistamine such as clemastine or diphenhydramine administered in combination with a steroid such as prednisone; an immunosuppressive such as cyclosporine in combination with a steroid such as prednisone; an anti-emetic such as ondansetron in combination with a steroid such as prednisone; an antibiotic such as enrofloxacin in combination with a steroid such as prednisone; and an antiparasitic agent such as nitenpyram, ivermectin or milbemycin in combination with a steroid such as prednisone. Steroids other than prednisone are also contemplated. Furthermore, the term "combination" can include physical combinations of the active agent or agents with the second therapeutic agent (e.g., steroid) in one dosage form, as well administration of the active agent or agents and the second therapeutic agent in separate dosage forms (e.g., administration of the active agent via TMOM™, followed or preceded by administration of the second therapeutic agent in any dosage form). Alternatively, the active agent or agents and second therapeutic agent may be administered essentially simultaneously.

i. Bioadhesive Agents

Optionally, in some embodiments the compositions of the invention can comprise a bioadhesive agent in addition to the active agent. The bioadhesive agents of various embodiments of the invention allow adherence of an active agent to a biological substrate, preferably the oral mucosa, more preferably the buccal mucosa, in order to maintain continual contact of the non-steroidal anti-inflammatory agent with the site of delivery. This process has been termed mucoadhesion when the substrate is mucosal tissue (see, e.g., Chang et al., J. Pharm. Sci. (1985) 74, 4, pp 399-405, which is incorporated by reference in its entirety for all purposes).

In one embodiment, the bioadhesive agents of the invention comprise at least one surface stabilizer (e.g., a cationic surface stabilizer), which is described in more detail below. The bioadhesive agents of various embodiments of the invention afford bioadhesion or additional bioadhesion of the transmucosal compositions to biological surfaces, such as the oral mucosa or buccal mucosa. The term bioadhesion includes any attractive interaction between two biological surfaces or between a biological and a synthetic surface. In the case of bioadhesive agents, the term bioadhesion is used to describe the adhesion between the transmucosal compositions of the invention and a biological substrate (i.e., the oral mucosa or buccal mucosa) (see, e.g., U.S. Pat. No. 6,428,814 for "Bioadhesive Nanoparticulate Compositions Having Cationic Surface Stabilizers," which is incorporated by reference in its entirety for all purposes).

Mechanisms that may be responsible for the bioadhesion phenomena include, but are not limited to, mechanical or physical interactions and chemical interactions. The first of these, mechanical or physical mechanisms, involves the physical interlocking or interpenetration between a bioadhesive agent and the receptor tissue, resulting from wetting of the bioadhesive surface, swelling of the bioadhesive polymer, penetration of the bioadhesive agent into a crevice of the tissue surface, or interpenetration of bioadhesive composition chains with those of the oral mucosa or other such related tissues. The second possible mechanism of bioadhesion incorporates forces such as ionic attraction, dipolar forces, van der Waals interactions, and hydrogen bonds. It is this second, or chemical, form of bioadhesion that is believed to be primarily responsible for the bioadhesive properties of the transmucosal compositions of the invention. However, physical and mechanical interactions may also play a role in the bioadhesion of such compositions.

The transmucosal compositions of various embodiments of the invention, which comprise additionally a bioadhesive agent, are useful in any situation in which it is desirable to apply the compositions to a biological surface. The compositions can coat the targeted surface in a continuous and uniform film, which is typically invisible to the naked human eye, but which allows penetration of the active agent.

Examples of bioadhesive agents include, but are not limited to, 23-lauryl ether, aprotinin, one, benzalkonium chloride, cetylpyridinium chloride, cetyltrimethylammonium bromide, cyclodextrin, dextran sulfate, lauric acid, lauric acid/propylene glycol, lysophosphatidylcholine, menthol, methoxysalicylate, methyloleate, oleic acid, phosphatidylcholine, polyoxyethylene, polysorbate 80, sodium salts of EDTA, glycocholate, glycodeoxycholate, lauryl sulfate, salicylate, taurocholate, and taurodeoxycholate, sulfoxides, or various alkyl glycosides.

ii. Permeation Enhancers

Optionally, the compositions of various embodiments of the invention can comprise a permeation enhancer to increase the passage of active agents through the oral mucosa. Permeation enhancers or penetration enhancers or similar terms are used to describe materials that enhance permeation of a therapeutically or prophylactically effective amount of active agent through the oral mucosa. Studies have suggested the feasibility of buccal delivery of even a rather large molecular weight pharmaceutical using a permeation enhancer (Aungst and Rogers, Int. J. Pharm. (1989) 53, pp. 227-235, which is incorporated herein by reference). The flux of active agent across the oral mucosa can be increased by changing either the resistance (i.e., the diffusion coefficient) or the driving force (i.e., the gradient for diffusion). Flux may be enhanced by the use of so-called permeation enhancers.

Preferred permeation enhancers for use in the transmucosal delivery systems of various embodiments of the invention include, but are not limited to, cell envelope disordering agents, solvents, steroidal detergents, bile salts, chelators, surfactants, non-surfactants, fatty acids, and mixtures thereof, with bile salt enhancers being more preferred.

Cell envelope disordering agents are known in the art as being useful in topical pharmaceutical preparations and function also in drug delivery through the skin or mucosa. These agents are thought to assist in dermal penetration by disordering the lipid structure of the stratum corneum cell-envelopes. A list of such agents is described in European Patent Application No. 43,738, published Jun. 13, 1982, which is incorporated herein by reference. It is believed that any cell envelope disordering agent can be used in various embodiments of the compositions and methods of this invention.

Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one, and other n-substituted-alkyl-azacycloalkyl-2-ones (atones); and the like.

Other permeation enhancers capable for use in various embodiments of the compositions and methods of the invention include DMSO or aqueous solutions of DMSO, such as taught in U.S. Pat. No. 3,551,554 to Herschler, U.S. Pat. No. 3,711,602 to Herschler, and U.S. Pat. No. 3,711,606 to Herschler, and atones (e.g., the n-substituted-alkyl-azacycloalkyl-2-ones) such as noted in U.S. Pat. No. 4,557,943 to Cooper.

Permeation enhancers for use in combination with the various embodiments of the compositions and methods of the invention also include, but are not limited to, POLYSORBATE-80, sorbitol, and phosphatidylcholine.

F. Kits

Various embodiments of the invention also provide for pharmaceutical packs or kits comprising one or more containers filled with one or more agents or compositions of the invention suitable for at least one transmucosal administration to the oral mucosa, for example, as single aerosol spray onto the oral mucosa of an animal. The containers and kits may contain more than one actuator for multiple administrations, adjustable actuators to allow dose adjustment or actuators of different shape and size to modulate particle spray or mist size or to enable administration to certain types and sizes of animals. Optionally associated with such container(s) can be a notice in the form prescribed by a governmental agency regulating the manufacture, use, or sale of pharmaceuticals or biological products, which notice reflects approval or approvability by the agency of manufacture, use, or sale for animal administration. In a certain embodiment, the kit contains more than one non-steroidal anti-inflammatory agent of the invention. In another embodiment, the kit comprises a non-steroidal anti-inflammatory agent of the invention and an additional therapeutic agent, including, but not limited to, a bioadhesion promoter, a permeation enhancer, a flavoring or flavor masking agent, or a combination thereof.

The invention is further defined by reference to the following examples, which are intended to be illustrative and not limiting.

G. Examples

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

Non-Steroidal Anti-Inflammatory Agents

Compositions according to the invention were made in accordance with the teachings of one or more of U.S. Pat. Nos. 5,869,082, 5,955,098, 6,110,486, and 6,676,931, each of which is herein incorporated by reference in its entirety for all purposes, which compositions were made to contain meloxicam (0.5-1.0%), ethanol, polyethylene glycol 400, povidone, sodium chloride and water.

Example 1

Meloxicam Formulations

An example of a composition according to the invention is shown below in Table 1:

TABLE 1

Illustrative Meloxicam Composition

| Ingredients | Amount (mg/g) |
|---|---|
| Meloxicam, BP | 4.67 |
| Boric Acid, NF | 0.77 |
| Potassium Chloride, USP | 0.93 |
| Polyvinyl alcohol, USP | 5.00 |
| Ethyl alcohol, dehydrated, USP | 150.00 |
| Sodium hydroxide, NF/FCC | 1.08 |
| Purified water, USP | 837.57 |

The formulation of Table 1 has a pH of approximately 8.4, and may be prepared by the following method:

Preparation of 0.93% Meloxicam Stock Solution

In a 250 mL media bottle, meloxicam, BP (0.93 g) in 94.00 g of purified water, USP and 4.95 g of 1 M sodium hydroxide solution. After the meloxicam completely dissolves, the pH should be approximately 11.5. if no pH adjustment is needed, additional purified water is added to adjust the total solution weight to 100 g. If the pH is not within the range of 11.5±0.2, then 1 M sodium hydroxide is added to adjust the pH to a value within this range, and additional purified water is added to provide a total solution weight of 100 g.

Preparation of Alkaline Borate Buffer

Boric acid, NF (12.37 g) and 14.91 g of potassium chloride, USP are added to a 1000 mL volumetric flask with 750 mL of purified water. The solution is mixed well, and diluted to 1000 mL. The resulting solution (50 mL) is mixed with 8.6 mL of 0.2 M sodium hydroxide in a 200 mL volumetric flask, and diluted with additional purified water to provide 200 mL of alkaline borate buffer solution.

Preparation of the Formulation of Table 1

The meloxicam stock solution (prepared as described above) is mixed with 10 g of 5% polyvinyl alcohol (aqueous solution) and mixed thoroughly. Then 20 g of the alkaline borate buffer solution (prepared as described above) is added and mixed well. Finally, 15 g of ethyl alcohol, dehydrated, as added and the solution is mixed. The pH is then tested and adjusted, as necessary, with 0.2 M HCl to a pH of 8.5±0.2. Then, additional alkaline borate buffer is added to provide a 0.47% (w/w) solution of meloxicam.

Meloxicam Solubility

Meloxicam is poorly soluble, and its solubility is pH dependent. The solubility of meloxicam in various solutions is shown below in Table 2, below.

TABLE 2

Meloxicam Solubility in Various Solvents

| Solvent | Meloxicam Solubility (w/v) |
|---|---|
| 100% Water | <1% |
| 100% Ethanol | <1% |
| 100% Propylene glycol | <1% |
| 100% PEG-400 | <1% |
| 50:50 Water:Ethanol | <1% |
| 50:50 Water:PEG-400 | <1% |
| 50:50 EtOH:PEG-400 | <1% |
| 50:50 Water:Propylene glycol | <1% |
| 50:50 Ethanol:Propylene glycol | <1% |
| 5% Povidone in water | <1% |

However, upon addition of very small amounts of 1 M NaOH solution, the meloxicam completely dissolved.

The solubility of meloxicam in various other solvent systems was evaluated. Sufficient meloxicam was added to a mixture of 80% water/15% EtOH/5% Poloxamer 188 to obtain a final concentration of 1% meloxicam. The meloxicam did not dissolve completely, and the resulting mixture had a pH of approximately 5.8. NaOH solution (1 M) was added to the mixture to provide a pH of 10. The meloxicam was observed to dissolve. The solution was then acidified to a pH of 7 with 0.2 M HCl, whereupon the meloxicam was observed to precipitate. Additional 1 M NaOH was added, adjusting the pH to 8, and the meloxicam redissolved and remained in solution.

Sufficient meloxicam was added to 100% water or 85:15 water:ethanol to provide a 1% meloxicam solution. Then, in each case, 1 M NaOH was added to ensure the complete dissolution of the meloxicam. Each solution was then titrated with HCl (aq). For the 100% water solution, meloxicam precipitation was observed when the pH dropped to a value of 7.2. After adjusting the pH to 10.1 the meloxicam redissolved. The pH was then reduced to a value of approximately 7.8, and no further precipitation was observed. Similarly, for the 85:15 water:ethanol solvent system, a precipitate formed when the initial apparent pH of 12 was reduced to 7.7 (by addition of HCl).

A 1% solution of meloxicam was prepared in a 95:5 water:propylene glycol solvent system. Concentrated NaOH solution (10 M) was added to aid in the dissolution of the meloxicam. However, the meloxicam did not dissolve because the concentration of the NaOH solution was too high. It was determined that solution having a pH value of less than 8 caused meloxicam precipitation. In order to ensure that the meloxicam remained in solution, the pH needs to be greater than about 8.0. However for safety and animal (e.g., canine) palatability, the pH should be less than about 9.0.

Storage Stability

Storage stability is an important consideration when formulating compositions intended to be administered by a spray-type device. For example, precipitation or decomposition of the active agent of the invention could result in delivery of less than the intended dose and/or cause plugging of the spray device. Accordingly, the compositions of the present invention were evaluated for stability at 5° C. Meloxicam (0.5% w/w) was dissolved in each of the solvent systems shown below in Table 3.

TABLE 3

Storage Stability of Various Meloxicam Solutions

| Matrix (w/w) | % Meloxicam | Filtered |
|---|---|---|
| 100% Water | 0.5 | No |
| 100% Water | 0.5 | Yes |
| 100% Water | 0.75 | No |
| 100% Water | 0.75 | Yes |
| 95:5 Water:Propylene glycol | 0.5 | No |
| 95:5 Water:Propylene glycol | 0.5 | Yes |
| 95:5 Water:Propylene glycol | 0.75 | No |
| 95:5 Water:Propylene glycol | 0.75 | Yes |
| 95:5 Water:EtOH | 0.5 | No |
| 95:5 Water:EtOH | 0.5 | Yes |
| 95:5 Water:EtOH | 0.75 | No |
| 95:5 Water:EtOH | 0.75 | Yes |
| Metacam ® | 0.5 | No |

Each solution was split into two aliquots, one of which was filtered, the other remaining unfiltered. After 24 hours, each of the solutions of Table 3 was clear and yellow, with no precipitate. After 7 days, only the following solutions remained precipitate-free: 0.5% meloxicam in 95:5 Water:EtOH, 0.5% meloxicam in 95:5 Water:Propylene glycol, and 0.75% meloxicam in 95:5 Water:Propylene glycol, all filtered. After 16 and 19 days, only the following remained precipitate-free: 0.5% meloxicam in 95:5 Water:EtOH, filtered and Metacam® (i.e., injectable meloxicam solution available from Boehringer-Ingelheim; each mL contains 5.0 mg meloxicam, 15% alcohol, 10% glycofural (tetraglycol), 5% Poloxamer 188, 0.6% NaCl, 0.5% glycine, 0.3% meglumine, balance water). After 27 days, only Metacam® was precipitate-free.

Stability of Meloxicam with Various Solubilizing Agents

Storage of meloxicam with either PVA, Polysorbate 80, or glycerin indicated that the physical stability of the meloxicam solution was greater with PVA than Polysorbate 80 or glycerin.

Spray Characteristics

Aqueous meloxicam solutions further comprising PVA as a solubilizing agent were found to provide relatively poor spray characteristics by "naked eye" observations of the spray pattern. Ethanol was added to these aqueous/PVA/meloxicam solutions at two levels: 7.5% and 15%. The results of spray characteristics studies are shown in Tables 4 and 5. The term "<10 µm" refers to the percentage of particles having a diameter of less than 10 µm. The terms "Dv(10)", "Dv(50)", and "Dv(90)" refer to the particle size below which the indicated percentage of the cumulative population occurs. Thus, "Dv (10)" indicates the particle size of which 10% of the cumulative population of particles is less than or equal to. The term "ovality" is the ratio $D_{max}/D_{min}$ where $D_{max}$ is the largest chord in mm which can be drawn within the spray pattern that crosses the COMw (i.e., center of mass of the spray pattern) in base units, and $D_{min}$ is the smallest chord that can be drawn within the spray pattern that crosses the COMw in base units. The closer the ovality is to 1.0, the more symmetrical the shape of the spray pattern. More symmetrical spray patterns are desired. The 0.5% PVA formulation has an ovality of 1.26, and the 0.25% PVA formulation has an ovality of 1.51. accordingly, the spray pattern of the 0.50% PVA formulation is preferred.

Increasing levels of ethanol improved the rheological characteristics of the composition by reducing the solution viscosity. In addition, higher levels of ethanol serve as an antimicrobial preservative. The formulation containing 15% ethanol provided a suitable spray "plume".

TABLE 4

Spray Characterization Study of 0.5% Meloxicam with 0.5% PVA and 15% EtOH

| Sample ID | <10 µm | Dv (10) | Dv (50) | Dv (90) | Span | Spray Angle | Ovality |
|---|---|---|---|---|---|---|---|
| 11 | 1.59% | 23.09 | 45.53 | 102.73 | 1.75 | 27.9 | 1.343 |
| 12 | 1.59% | 22.96 | 46.50 | 106.95 | 1.81 | 39.0 | 1.154 |
| 21 | 1.64% | 23.18 | 49.14 | 108.73 | 1.74 | 42.5 | 1.211 |
| 22 | 1.69% | 22.86 | 48.16 | 108.63 | 1.78 | 29.9 | 1.205 |
| 31 | 1.52% | 23.45 | 47.92 | 104.45 | 1.69 | 31.2 | 1.186 |
| 32 | 1.57% | 23.02 | 48.02 | 103.92 | 1.68 | 40.5 | 1.468 |
| Average | 1.60% | 23.09 | 47.55 | 105.90 | 1.74 | 35.17 | 1.26 |
| Std. Dev. | 0.06% | 0.21 | 1.30 | 2.55 | 0.05 | 6.22 | 0.12 |
| RSD | 3.7 | 0.9 | 2.7 | 2.4 | 2.9 | 17.7 | 9.5 |

TABLE 5

Spray Characterization Study of 0.5% Meloxicam with 0.25% PVA and 15% EtOH

| Sample ID | <10 µm | Dv (10) | Dv (50) | Dv (90) | Span | Spray Angle | Ovality |
|---|---|---|---|---|---|---|---|
| 11 | 2.62% | 18.7 | 39.08 | 100.01 | 2.08 | 29.1 | 1.298 |
| 12 | 2.46% | 19.38 | 39.41 | 96.70 | 1.96 | 29.6 | 1.426 |
| 21 | 2.36% | 19.36 | 40.27 | 102.34 | 2.06 | 37.9 | 1.336 |
| 22 | 2.33% | 19.58 | 39.98 | 96.13 | 1.91 | 44.0 | 1.818 |
| 31 | 2.34% | 19.62 | 41.67 | 99.86 | 1.93 | 29.2 | 1.593 |
| 32 | 2.41% | 19.22 | 40.80 | 98.49 | 1.94 | 31.2 | 1.611 |
| Average | 2.42% | 19.31 | 40.20 | 98.92 | 1.98 | 33.50 | 1.51 |
| Std. Dev. | 0.11% | 0.33 | 0.94 | 2.31 | 0.07 | 6.13 | 0.20 |
| RSD | 4.5 | 1.7 | 2.3 | 2.3 | 3.6 | 18.3 | 13.0 |

Stability of Meloxicam Formulations Containing Glycofural

Glycofural is used as a penetration enhancer for topical and intranasal formulations, and is a component of the commercial injectable Metacam® formulation. However, as shown in Tables 4-6, below, meloxicam was less stable in formulations containing glycofurol than in formulations containing ethanol.

TABLE 6

Stability of 0.5% Meloxicam with Glycofurol

| Stability Condition* | Spray Weight | Spray Content | SC/SW Ratio | % Label Claim | Impurity B & C | Other Impurity |
|---|---|---|---|---|---|---|
| Initial | N/A | Bulk 0.484%; RSD: 0.2% | N/A | 96.80% | N/D | Unknown 0.7% |
| 25/60/2 wk; n = 3 | 98.4 mg; RSD: 1.5% | 0.461 mg; RSD: 1.1% | 0.00468; RSD: 0.4% | 92.10% | <0.10% | N/D |
| 25/60/4 wk; n = 3 | 100.2 mg; RSD: 2.5% | 0.475 mg; RSD: 2.3% | 0.00474; RSD: 0.5% | 95.00% | Imp. B: 0.18% | N/D |
| 25/60/8 wk; n = 3 | 91.6 mg; RSD: 9.4% | 0.472 mg; RSD: 9.0% | 0.00466; RSD: 0.5% | 85.40% | Imp. B: 0.14% | N/D |
| 25/60/12 wk; n = 3 | 99.8 mg; RSD: 2.5% | 0.467 mg; RSD: 1.3% | 0.00468; RSD: 1.0% | 93.50% | Imp. B: 0.20% | N/D |
| 25/60/4 mo; n = 3 | 100.7 mg; RSD: 0.4% | 0.473 mg; RSD: 1.1% | 0.00469; RSD: 0.9% | 94.50% | Imp. B: 0.27% | N/D |
| 25/60/4 mo, cycle**; n = 3 | 90.5 mg; RSD: 15.1% | 0.418 mg; RSD: 14.9% | 0.00462; RSD: 0.3% | 83.60% | Imp. B: 0.25% | N/D |
| 40/75/2 wk; n = 3 | 96.1 mg; RSD: 2.5% | 0.450 mg; RSD: 2.4% | 0.00468; RSD: 0.3% | 89.90% | Imp. B: 0.10% | N/D |
| 40/75/4 wk; n = 3 | 86.0 mg; RSD: 12.8% | 0.411 mg; RSD: 13.0% | 0.00478; RSD: 0.3% | 82.10% | Imp. B: 0.29% | N/D |
| 40/75/8 wk; n = 3 | 84.9 mg; RSD: 10.1% | 0.396 mg; RSD: 9.8% | 0.00466; RSD: 0.4% | 79.20% | Imp. B: 0.33% | N/D |
| 40/75/12 wk; n = 3 | 86.0 mg; RSD: 9.5% | 0.402 mg; RSD: 9.4% | 0.00467; RSD: 0.4% | 80.40% | Imp. B: 0.49% | N/D |
| 40/75/4 mo; n = 3 | 85.4 mg; RSD: 8.0% | 0.411 mg; RSD: 8.1% | 0.00481; RSD: 2.0% | 82.20% | Imp. B: 0.67% | N/D |

*Accelerated stability conditions: ° C./% Relative Humidity/test interval
**samples cycled from 5° C./16 hr to 40° C./8 hr
N/D means not detected

TABLE 7

Stability of 0.5% Meloxicam with 0.5% PVA and 7.5% EtOH

| Stability Condition* | Spray Weight | Spray Content | SC/SW Ratio | % Label Claim | Impurity B & C | Other Impurity |
|---|---|---|---|---|---|---|
| Initial | N/A | Bulk 0.475%; RSD: 0.4% | N/A | 95.00% | N/D | Unknown 0.5% |
| 25/60/2 wk; n = 3 | 98.4 mg; RSD: 0.5% | 0.467 mg; RSD: 0.7% | 0.00475; RSD: 0.3% | 93.40% | <0.10% | N/D |
| 25/60/4 wk; n = 3 | 98.6 mg; RSD: 1.5% | 0.481 mg; RSD: 2.0% | 0.00488; RSD: 0.5% | 96.20% | <0.10% | N/D |
| 25/60/8 wk; n = 3 | 90.3 mg; RSD: 11.5% | 0.436 mg; RSD: 11.9% | 0.00483; RSD: 0.5% | 87.20% | <0.10% | N/D |
| 25/60/12 wk; n = 3 | 90.5 mg; RSD: 11.3% | 0.430 mg; RSD: 11.5% | 0.00475; RSD: 0.4% | 85.90% | <0.10% | N/D |
| 25/60/4 mo; n = 3 | 96.7 mg; RSD: 2.4% | 0.463 mg; RSD: 3.6% | 0.00479; RSD: 1.8% | 92.70% | <0.10% | N/D |
| 25/60/4 mo, cycle**; n = 3 | 98.7 mg; RSD: 5.4% | 0.466 mg; RSD: 5.0% | 0.00472; RSD: 0.4% | 93.10% | <0.10% | N/D |
| 40/75/2 wk; n = 3 | 99.1 mg; RSD: 0.6% | 0.476 mg; RSD: 0.3% | 0.00480; RSD: 0.4% | 95.30% | <0.10% | N/D |

TABLE 7-continued

Stability of 0.5% Meloxicam with 0.5% PVA and 7.5% EtOH

| Stability Condition* | Spray Weight | Spray Content | SC/SW Ratio | % Label Claim | Impurity B & C | Other Impurity |
|---|---|---|---|---|---|---|
| 40/75/4 wk; n = 3 | 92.8 mg; RSD: 11.9% | 0.456 mg; RSD: 12.0% | 0.00491; RSD: 0.9% | 91.20% | <0.10% | N/D |
| 40/75/8 wk; n = 3 | 96.6 mg; RSD: 2.7% | 0.462 mg; RSD: 2.3% | 0.00478; RSD: 0.9% | 92.50% | <0.10% | N/D |
| 40/75/12 wk; n = 3 | 97.3 mg; RSD: 1.2% | 0.464 mg; RSD: 2.0% | 0.00477; RSD: 1.1% | 92.80% | Imp. B: 0.18% | N/D |
| 40/75/4 mo; n = 3 | 98.1 mg; RSD: 1.7% | 0.482 mg; RSD: 1.6% | 0.00491; RSD: 0.6% | 96.40% | Imp. B: 0.54% | N/D |

*Accelerated stability conditions: ° C./% Relative Humidity/test interval
**samples cycled from 5° C./16 hr to 40° C./8 hr
N/D means not detected

TABLE 8

Stability of 0.5% Meloxicam with 0.5% PVA and 15% EtOH

| Stability Condition* | Spray Weight | Spray Content | SC/SW Ratio | % Label Claim | Impurity B & C | Other Impurity |
|---|---|---|---|---|---|---|
| Initial | N/A | Bulk 0.470%; RSD: 0.4% | N/A | 94.00% | N/D | Unknown 0.5% |
| 25/60/2 wk; n = 3 | 98.5 mg; RSD: 0.5% | 0.474 mg; RSD: 1.5% | 0.00481; RSD: 0.2% | 94.70% | <0.10% | N/D |
| 25/60/4 wk; n = 3 | 98.5 mg; RSD: 1.2% | 0.485 mg; RSD: 1.5% | 0.00492; RSD: 0.3% | 97.00% | <0.10% | N/D |
| 25/60/8 wk; n = 3 | 90.7 mg; RSD: 8.4% | 0.454 mg; RSD: 7.7% | 0.00485; RSD: 0.7% | 90.90% | Imp. B: 0.14% | N/D |
| 25/60/12 wk; n = 3 | 98.5 mg; RSD: 1.9% | 0.481 mg; RSD: 1.1% | 0.00488; RSD: 0.8% | 96.20% | <0.10% | N/D |
| 25/60/4 mo; n = 3 | 98.8 mg; RSD: 1.2% | 0.493 mg; RSD: 2.6% | 0.00499; RSD: 3.8% | 98.50% | <0.10% | N/D |
| 25/60/4 mo; cycle**; n = 3 | 98.1 mg; RSD: 4.6% | 0.467 mg; RSD: 1.9% | 0.00476; RSD: 1.0% | 93.40% | <0.10% | N/D |
| 40/75/2 wk; n = 3 | 95.2 mg; RSD: 4.6% | 0.459 mg; RSD: 4.4% | 0.00482; RSD: 0.2% | 91.80% | <0.10% | N/D |
| 40/75/4 wk; n = 3 | 98.5 mg; RSD: 1.1% | 0.490 mg; RSD: 1.2% | 0.00497; RSD: 0.2% | 97.90% | <0.10% | N/D |
| 40/75/8 wk; n = 3 | 96.6 mg; RSD: 2.7% | 0.468 mg; RSD: 3.3% | 0.00484; RSD: 1.4% | 93.70% | <0.10% | N/D |
| 40/75/12 wk; n = 3 | 97.4 mg; RSD: 3.0% | 0.469 mg; RSD: 3.2% | 0.00482; RSD: 0.9% | 93.80% | Imp. B: 0.12% | N/D |
| 40/75/4 mo; n = 3 | 100.5 mg; RSD: 0.6% | 0.504 mg; RSD: 2.9% | 0.00501; RSD: 2.9% | 100.80% | Imp. B: 0.35% | N/D |

*Accelerated stability conditions: ° C./% Relative Humidity/test interval
**samples cycled from 5° C./16 hr to 40° C./8 hr
N/D means not detected For the formulation with glycofurol, the initial meloxicam concentration was 96.8% of the label claim, and dropped to 82.2% at the 4 month 40° C./75% R.H. time point. In addition, an impurity "B" was identified. The concentration of impurity "B" started at 0.1% at 2 weeks, and increased to 0.7% at 4 months. The formulation containing glycofurol showed a lack of chemical stability with time, especially under accelerated stability conditions.

For the 7.5% ethanol formulation, the initial meloxicam concentration was 95.0% and was 96.4% after 4 months at 40° C./75% R.H. Under the 40° C./75% R.H. conditions, the level of impurity "B" was less than 0.1% through 8 weeks of testing. Observable levels of impurity "B" appeared at 12 weeks (0.2%) and rose to 0.4% at 4 months. This level of impurity "B" formation was less than that observed for the formulation containing glycofurol.

For the 15% ethanol formulation, the initial meloxicam concentration was 94.0% and increased to 100.8% after 4 months at 40° C./75% R.H. The increase in meloxicam concentration may be due to evaporation of some of the ethanol. Under the 40° C./75% R.H. conditions, the level of impurity "B" was less than 0.1% through 8 weeks of testing. Observable levels of impurity "B" appeared at 12 weeks (0.1%) and rose to 0.4% at 4 months. This level of impurity "B" formation was less than that observed for the formulation containing glycofurol, and the formulation containing 7.5% ethanol.

Compositions of the present invention, as described above were formed into a spray that was administered to dogs via the buccal mucosa, between the lips and teeth of each animal at a target dose of about 0.2 mg/kg (approximately 0.1 mg/lb) body weight.

One of skill in the veterinary arts will recognize that the target dose can vary depending upon the nature and severity of the condition being treated or prevented, the species of the animal being treated, the size of the animal being treated, etc.

In addition, various treatment protocols may be used. For example, the animal can be treated once, or repeated at intervals during a single day, or at intervals over an extended time depending on the nature of the condition treated, the size and condition of the animal treated, etc. For example acute conditions may be treated for a brief period with one or more administration of the compositions according to the invention, whereas chromic conditions may require repeated (e.g., daily) administrations of the compositions over an extended time.

Example 2

Canine Meloxicam Absorption Study

A six dog, two-way crossover experiment comparing conventional oral administration of meloxicam (i.e., Metacam® oral suspension) with transmucosal oral administration (i.e., commercially available Metacam® injectable solution applied via transmucosal oral spray) of meloxicam was performed. The target dose was 0.2 mg/kg of meloxicam. The average oral suspension dose was 0.20 mg/kg (range 0.19-0.21 mg/kg), and the average dose using transmucosal oral administration was 0.20 mg/kg (range 0.19-0.21 mg/kg). Blood samples were obtained at 0, 5, 30 minutes and 1, 2, 4, 8, 12, 24, 48, and 72 hours post dose.

FIG. 1 shows that, following administration of the meloxicam using TMOM™, the absorption time, peak plasma concentration, and total absorption are comparable or better relative to the delivery profile obtained with the oral suspension. Thus, TMOM™ provides a simpler administration method which delivers meloxicam as effectively as conventional oral dosage forms.

FIG. 2 shows pharmacokinetic parameters for administration of the oral suspension and administration using TMOM™. The AUC represents the area under the curve or the total amount of drug exposure to the animal following administration by the two different dosage forms. The $C_{max}$ represents the maximum plasma concentration of meloxicam measured in ng/ml when administered by the dosage forms. The $T_{max}$ denotes the time it takes to reach maximum plasma concentration of meloxicam following administration of both dosage forms. The t½ is the calculated elimination half-life (the time it takes for plasma concentrations to decrease by 50%) of the active agent (in this case, meloxicam) when administered by both dosage forms. Absorption half-life is the amount of time it takes for half of what is left at the site of absorption to be absorbed.

FIG. 3 shows that meloxicam administered via TMOM™ appears to be bioequivalent to meloxicam administered via an oral suspension.

Example 3

Canine Anesthetized Meloxicam Absorption Study

Figure 4:
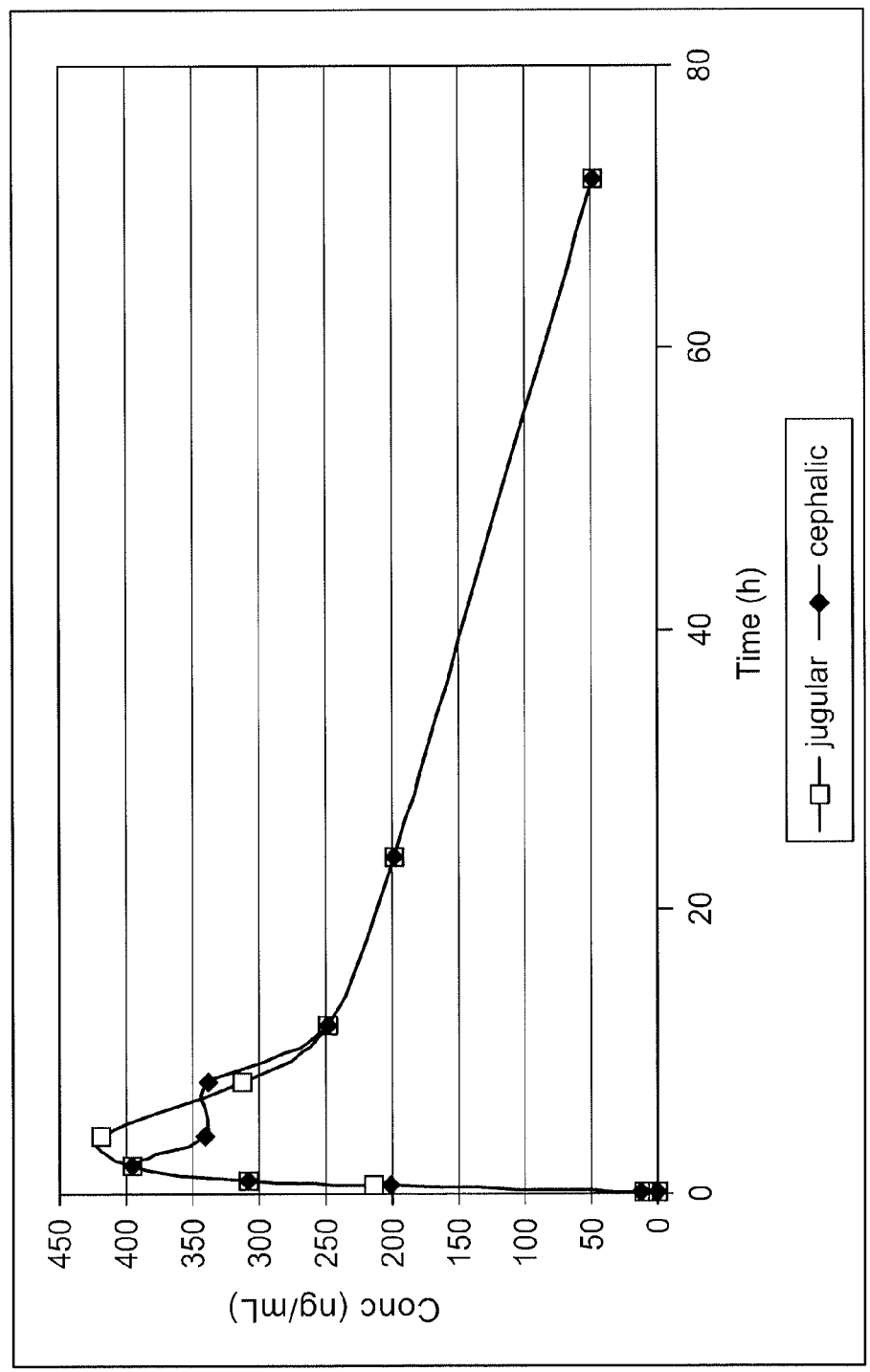
FIG. 4 shows the mean cephalic and jugular blood plasma levels of meloxicam in anesthetized dogs, administered via TMOM™.
Figure 5:
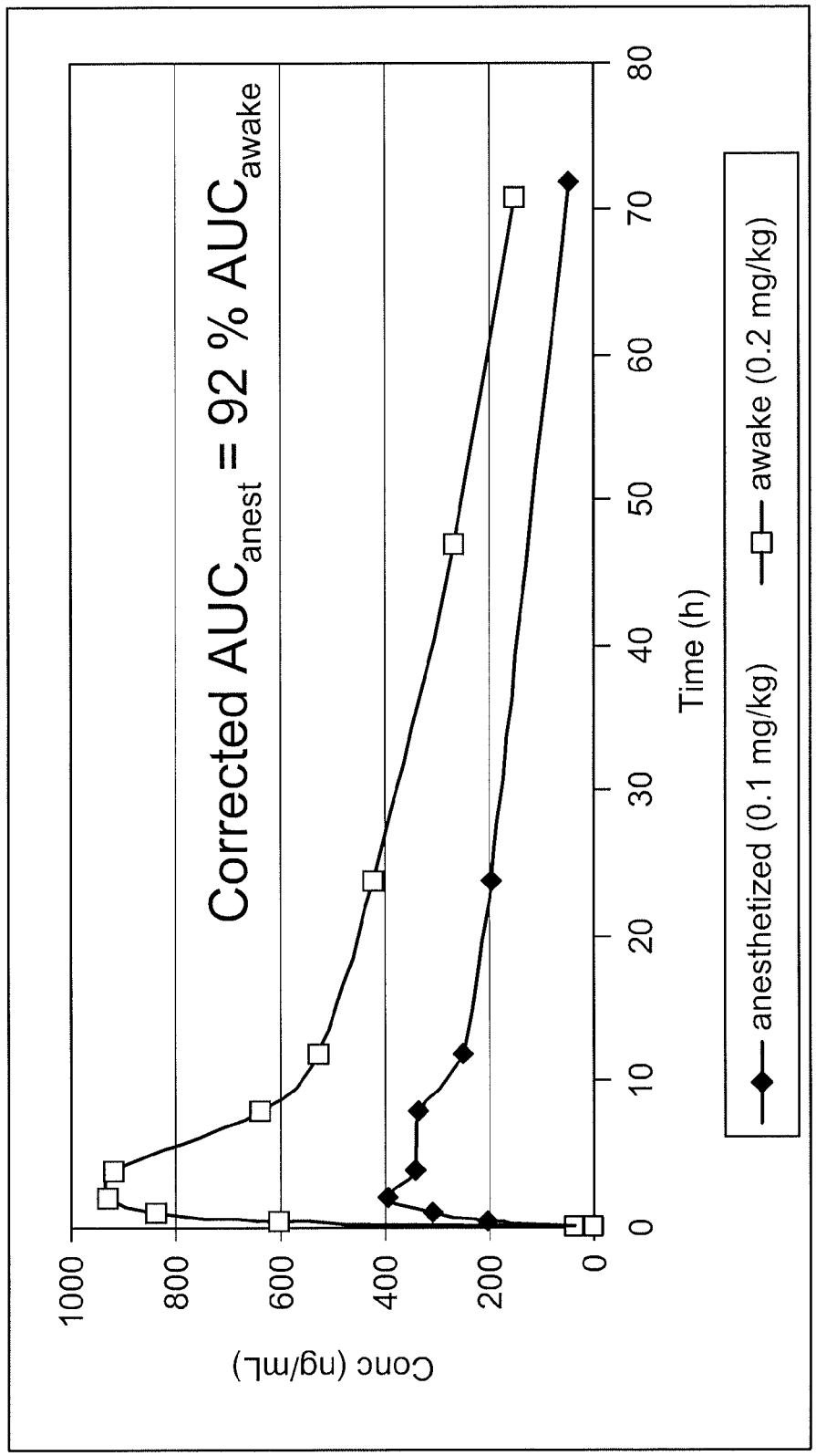
FIG. 5 shows blood plasma concentrations of meloxicam for two different meloxicam TMOM™ formulations in anesthetized and awake dogs.

A canine anesthetized absorption study was also carried out. The subjects were anesthetized dogs using minimal pre-anesthetics (isoflurane via an endotracheal tube). The possibility of run off into and absorption by the gastrointestinal tract was prevented by obstructing the esophagus with a Foley catheter. The meloxicam was administered using a transmucosal oral mist, and after 30 minutes, the dogs' mouths were washed to remove any residual oral mist formulation. Blood samples were taken 0, 5, 30 min, and 1, 2, 4, 8, 12, 24, and 72 hours post-dose. Jugular and cephalic vein samples were obtained 5, 30 min and 4, 8 hours post-dose. The target dosage was 0.1 mg/kg (4.66 mg/mL meloxicam in 15% ethanol, 0.5% polyvinyl alcohol, pH adjusted to 8.5, 200 µL (0.09 mg), dose range 0.08-0.15 mg/kg). The results are shown in FIGS. 4 and 5.

Transmucosal delivery of meloxicam was clearly confirmed. FIG. 4 shows that absorption of meloxicam was transmucosal as gastrointestinal absorption was impossible. This result was confirmed by the higher jugular plasma (i.e., drainage pathway of oral mucosa) levels of meloxicam as compared to cephalic (systemic) levels at 30 min and 4 h. In addition, the results show that transmucosal absorption can occur under anesthesia.

Furthermore, up to approximately 90% of the dose in an awake animal was delivered transmucosally. FIG. 5 compares the plasma concentrations of meloxicam in anesthetized canines and awake animals (from the previous study shown in FIG. 1 TMOM™ administration at 0.2 mg/kg-cephalic). After correction for the higher TMOM™ dose administered to the awake animal, the AUC for anesthetized animals is comparable (~92%) to the AUC for awake animals.

Example 4

Canine Carprofen Study

A six dog, three-way crossover experiment comparing conventional oral administration of carprofen (Rimadyl® caplets, 25 mg; average dose 1.06 mg/lb (0.93-1.14 mg/lb)), transmucosal oral administration of carprofen (Rimadyl® injectable solution, 50 mg/mL; average dose 1.08 mg/lb (0.96-1.14 mg/lb)), and subcutaneous injection of carprofen (Rimadyl® injectable solution, 50 mg/mL; average dose 1.08 mg/lb (0.96-1.16 mg/lb)) was performed. Blood samples were obtained at 0, 5, 30 minutes and 1, 2, 4, 8, 12, and 24 hours post dose. The results are shown in FIGS. 6 and 7.

Figure 6:
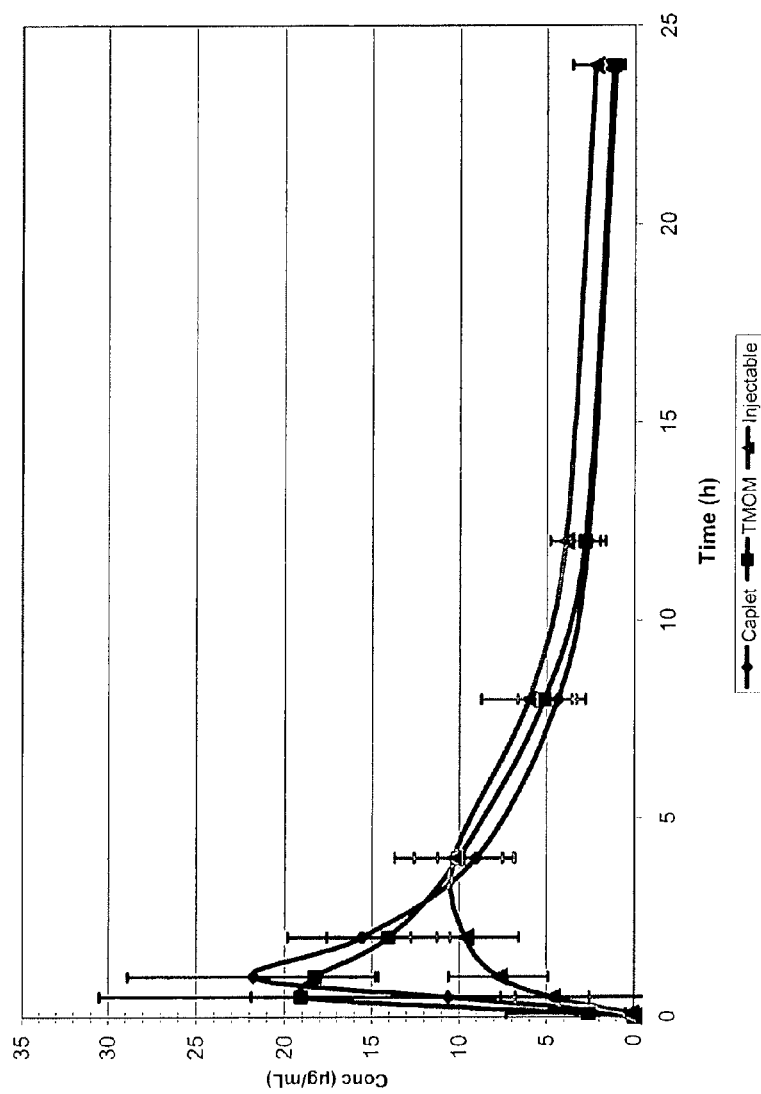
FIG. 6 shows a comparison of blood plasma levels of carprofen in dogs, administered via caplet, TMOM™, or injected.

Transmucosal oral administration was more similar to caplet administration than to subcutaneous injection (FIG. 6). The subcutaneous injection administration resulted in slower absorption and greater time to peak concentrations ($T_{max}$) than either caplet or TMOM™ administration. FIG. 7 shows that the AUC values of the three administration methods were all similar, and the $C_{max}$ of the subcutaneous injection was approximately half that of either the caplet or transmucosal oral administration. Transmucosal oral administration resulted in slightly faster absorption of carprofen than the caplet—there was no lag time and a shorter $T_{max}$. The $C_{max}$ and AUC values for the caplet and transmucosal oral administration of carprofen were very similar.

Example 5

Canine Anesthetized Carprofen Absorption Study

A canine anesthetized absorption study was also carried out. The subjects were anesthetized dogs using minimal pre-anesthetics (isoflurane via an endotracheal tube). The possibility of run off into and absorption by the gastrointestinal tract was prevented by obstructing the esophagus with a Foley catheter. The carprofen was administered using a transmucosal oral mist. Blood samples were taken 0, 5, 15, 30 min, and 1, 2, 4, 8, 12, and 24 hours post-dose. Jugular and cephalic vein samples were obtained 5, 15 and 30 and 1 and 2 hours post-dose. The target dosage was 2.2 mg/kg (50 mg/mL Rimadyl® injectable solution, 300 µL (15 mg), target dose range 1.9-2.5 mg/kg). The results are shown in FIGS. 8 and 9.

Figure 8:
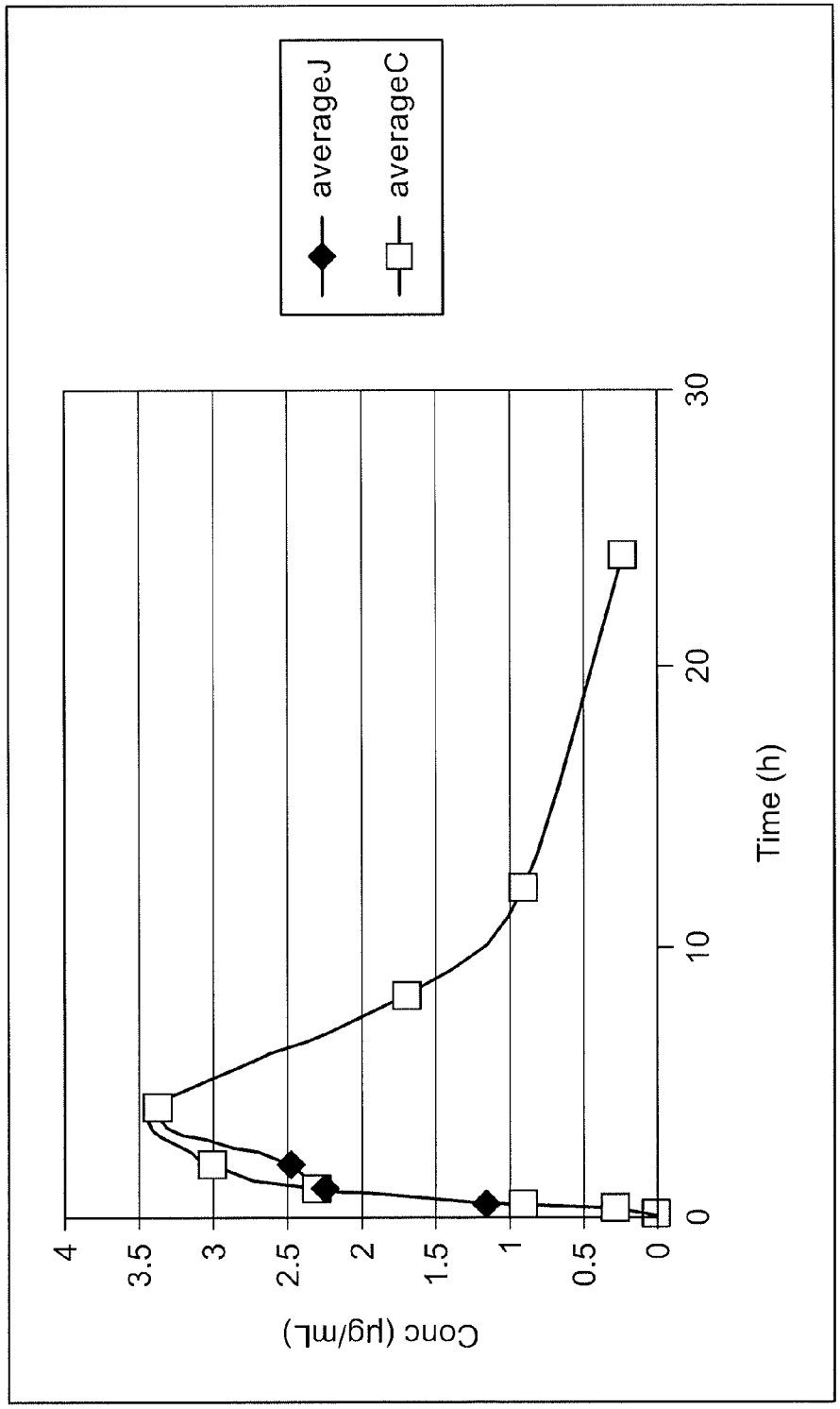
FIG. 8 shows mean cephalic and jugular blood plasma levels of carprofen in anesthetized dogs, administered via TMOM™.
Figure 9:
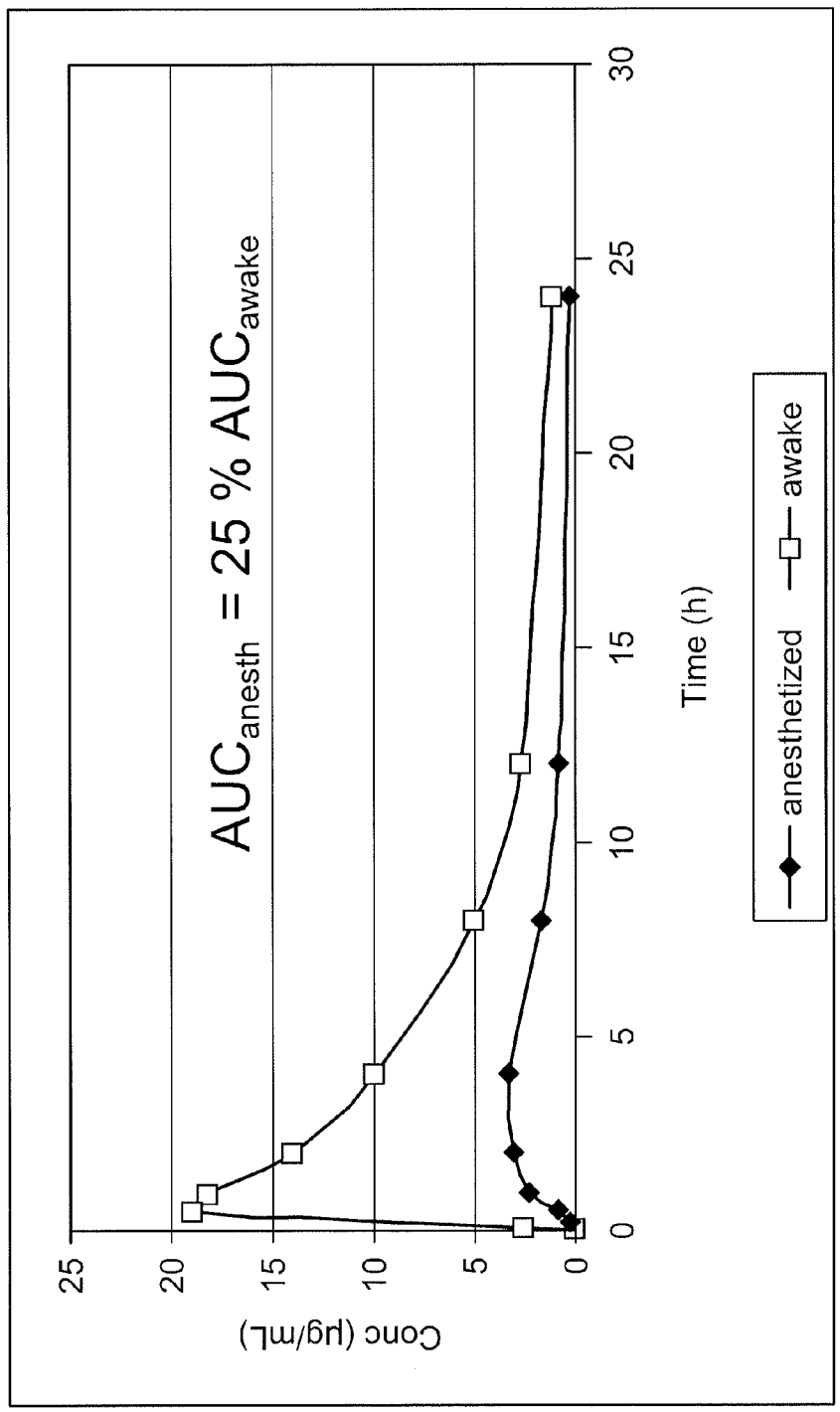
FIG. 9 shows blood plasma levels of carprofen administered via TMOM™ in anesthetized and awake dogs.

FIG. 8 confirms transmucosal delivery of carprofen as gastrointestinal absorption was impossible which was confirmed by higher plasma jugular levels of carprofen as compared to cephalic levels at 30 min. FIG. 9 shows blood plasma levels of carprofen in anesthetized and awake (from FIG. 6—cephalic) dogs. The AUC for anesthetized animals was approximately 25% of that for awake animals.

Antihistamine Agents

A composition according to the invention was made in accordance with the teachings of one or more of U.S. Pat. Nos. 5,869,082, 5,955,098, 6,110,486, and 6,676,931. This composition was formed into a spray that was administered to dogs, horses, and cats, via the buccal mucosa, between the lips and teeth of each animal, at a target dose of about 0.1 mg/kg or about 1 mg/kg body weight.

Example 6

A six animal (in each species: canine, feline, equine) two-way crossover experiment was carried out using clemastine tablets (Tavist®) and a clemastine transmucosal oral administration composition (25 mg/mL clemastine fumarate, vehicle: 75% ethanol, 25% water). The target dose for canine subjects was 1 mg/kg (both transmucosal oral administration and tablets). The average tablet dose was 0.96 mg/kg (0.95-0.97 mg/kg) and the average transmucosal oral administration dose was 0.97 mg/kg (0.91-1.06 mg/kg) administered in a spray volume of 400-650 µL using 4-7 pumps of the spray device. The target dose for feline subjects was also 1 mg/kg for both transmucosal oral administration and tablets. The average tablet dose of 1.07 mg/kg (0.89-1.22 mg/kg) and the average transmucosal oral administration dose was 0.95 mg/kg (0.83-1.14 mg/kg) administered in a spray volume of 100-200 µL using 1-2 pumps of the spray device. The target dose for equine subjects was 0.1 mg/kg for both transmucosal oral administration and tablets. The average tablet dose (via stomach tube) was 0.1 mg/kg (0.10-0.11 mg/kg) and the average transmucosal oral administration dose was 0.1 mg/kg (0.09-0.11 mg/kg) administered in a spray volume of 1.4-1.7 mL using 14-17 pumps of the spray device.

Blood samples were taken 5, 15, 30 min, 1, 2, 4, 7, 12, 24 hours post dose. Variable (none to moderate, mild to severe) salivation was observed in the canine and feline subjects, respectively.

Figure 10:
FIG. 10 shows the mean plasma concentrations of clemastine fumarate when administered using two different dosage forms (regular swallow tablets and TMOM™) at the same dosage (1 mg/kg) and both administered by the oral route to cats.

FIGS. 10 and 11 show faster clemastine uptake in feline subjects using transmucosal oral administration (shorter $T_{max}$) compared to conventional oral administration. Lower AUC values for feline subjects appear to be an artifact of salivation observed for these subjects.

Figure 12:
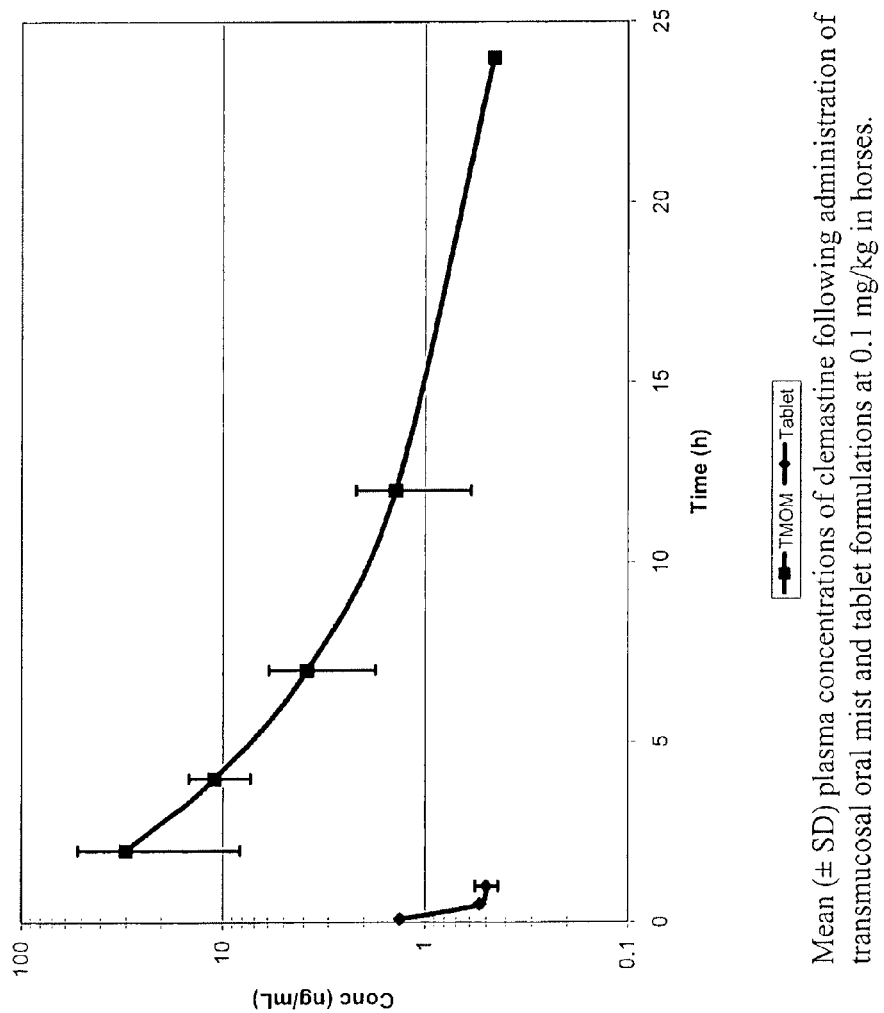
FIG. 12 shows the mean plasma concentrations of clemastine fumarate when administered using two different dosage forms (regular swallow tablets and TMOM™) at the same dosage (0.1 mg/kg) and both administered by the oral route to horses. The tablets were broken and administered via nasogastric tube as a gavage and the TMOM™ was administered to the buccal oral mucosa. The plasma concentration of clemastine fumarate is shown on a logarithmic scale. Following dosing with the tablets it was only possible to measure clemastine fumarate at three timepoints where the plasma concentrations achieved detectable levels so the curve is only depicted for a short period of time.

FIGS. 12 and 13 show significantly better clemastine bioavailability in equine subjects with transmucosal oral administration and more rapid drug uptake (shorter $T_{max}$). It was difficult to compare the PK parameters of the conventional oral administration approach (i.e., oral gavage) and transmucosal oral administration due to the extremely poor bioavailability in equine subjects of clemastine in tablet form. However, the $t_{1/2}$ with transmucosal oral administration is similar to that reported in the literature (2.8 hrs with transmucosal oral administration vs. 2.9 hrs with oral gavage; Törneke et al., J. Vet. Pharmacol. Therap. 26, pages 151-157, 2003).

Figure 14:
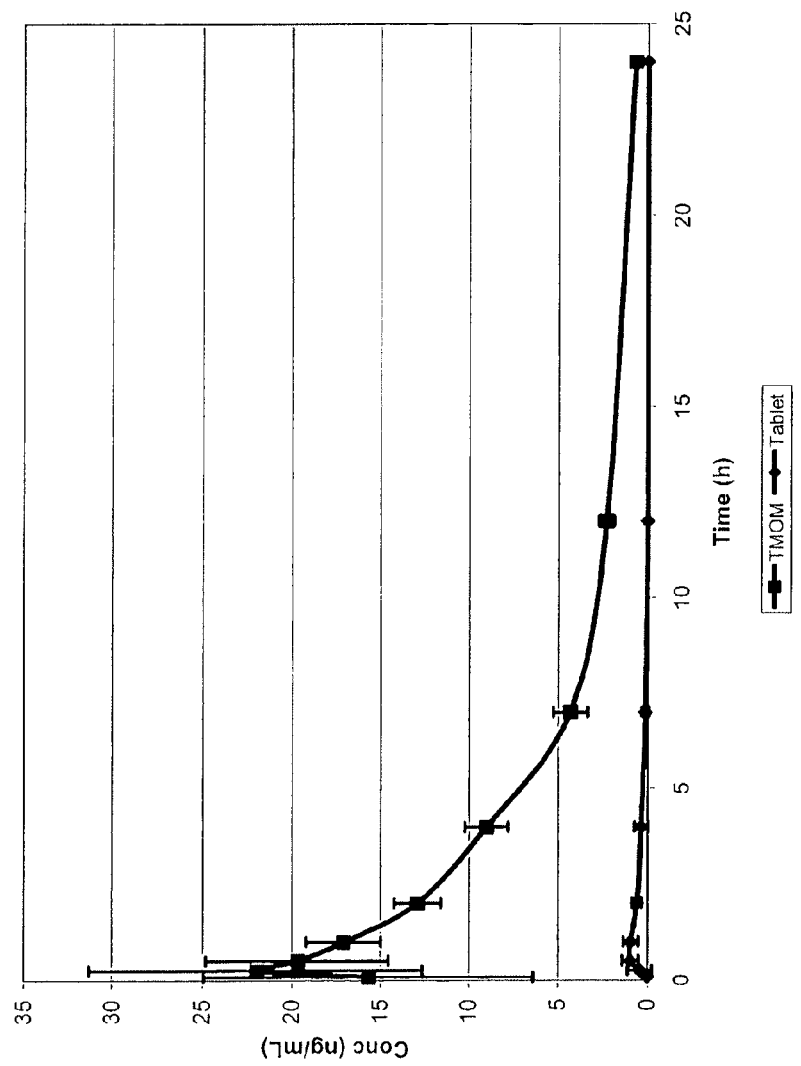
FIG. 14 shows mean plasma concentrations of clemastine fumarate in canines following administration of TMOM™ and tablet formulations at ~1.0 mg/kg.

FIGS. 14 and 15 show significantly better clemastine relative bioavailability (AUC) in canine subjects with a much higher peak ($C_{max}$) achieved with transmucosal oral administration compared to conventional oral (i.e., tablet) administration.

The transmucosal oral spray preparation of the clemastine composition exhibited unexpectedly high plasma drug concentrations in dogs (see FIGS. 14 and 15) and horses (see FIGS. 12 and 13), as compared to administration of a similar dose (on a mg/kg basis) via oral tablet form to each type of animal. In cats, (see FIGS. 10 and 11) clemastine was well absorbed, although the metabolism of the drug in that species is different from the other species, and consequently there was less difference in plasma concentrations between the transmucosal oral spray preparation and oral tablets.

In dogs, for example, as can be seen from FIG. 15, the total delivery of available clemastine to the bloodstream, as represented by AUC, and the maximum clemastine concentration, as represented by $C_{max}$, in the blood are both about an order of magnitude greater for the TMOM™ administration route than for the oral tablet administration route. Further, the maximum release of the antihistamine into the bloodstream of dogs happens quicker by about 10 minutes, as shown by $T_{max}$ values, for the TMOM™ administration route than for the oral tablet administration route.

Thus, TMOM™ administration appears to provide substantially higher plasma levels of clemastine in animals, particularly in canines and equines, compared to conventional oral dosage forms (e.g., tablets), and provides a significantly more convenient and safer alternative to intravenous administration.

Example 7

Canine Anesthetized Absorption Study

A canine anesthetized absorption study was also carried out. The subjects were anesthetized dogs using minimal pre-anesthetics (isoflurane via an endotracheal tube. The possibility of run off into and absorption by the gastrointestinal tract was prevented by obstructing the esophagus with a Foley catheter. The clemastine was administered using TMOM™. Blood samples were taken 0, 5, 15, 30 min, and 1, 2, 4, 8, 12 and 24 hours post-dose. Jugular and cephalic vein samples were obtained 5, 15 and 30 and 1 and 2 hours post-dose. The target dosage was 0.33 mg/kg (16.67 mg/mL clemastine in 75% ethanol, 25% water, 200 µL (3.3 mg), dose range 0.30-0.55 mg/kg).

Figure 16:
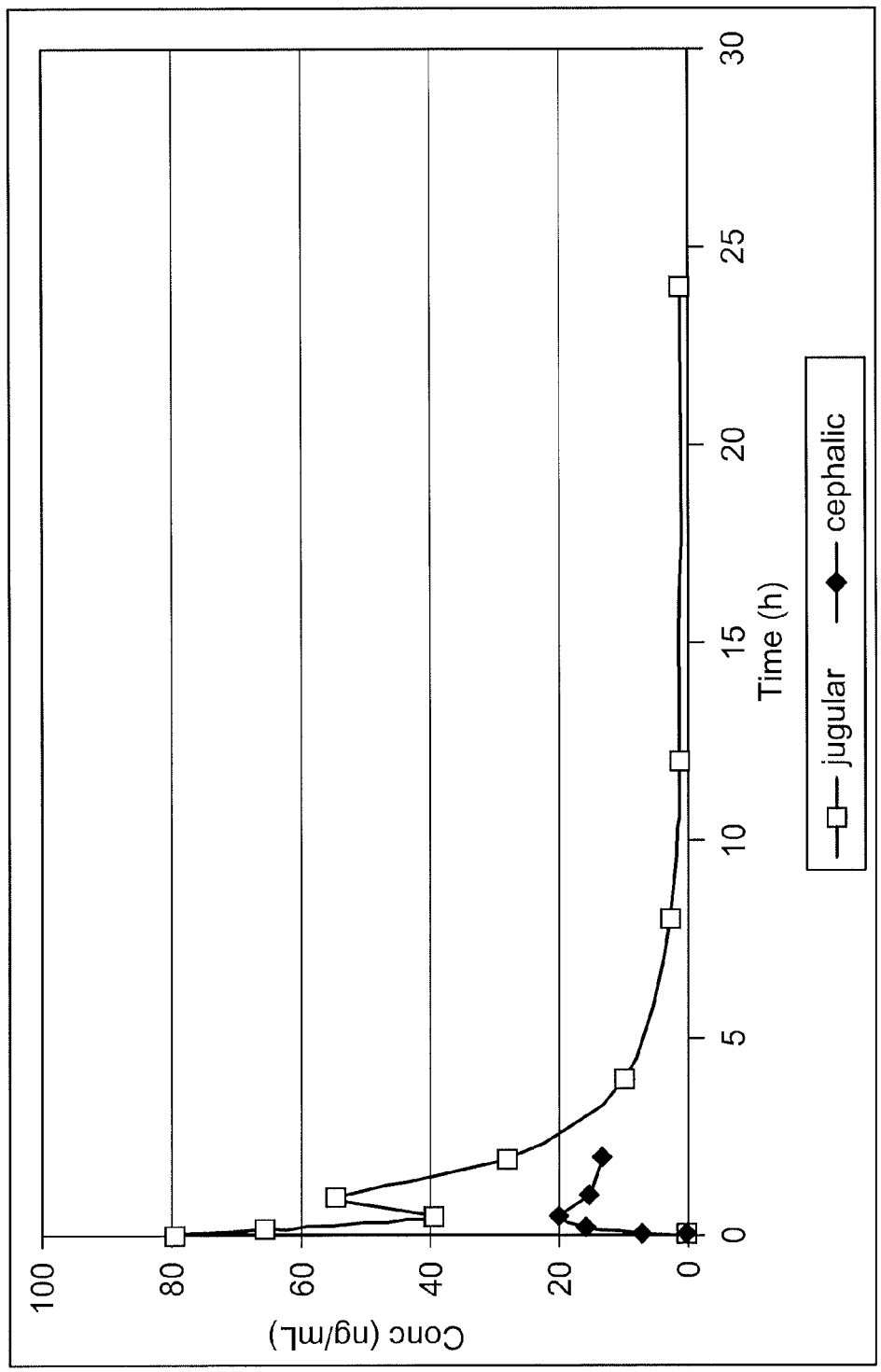
FIG. 16 shows cephalic and jugular blood plasma levels of clemastine fumarate in anesthetized dogs, administered via TMOM™.
Figure 17:
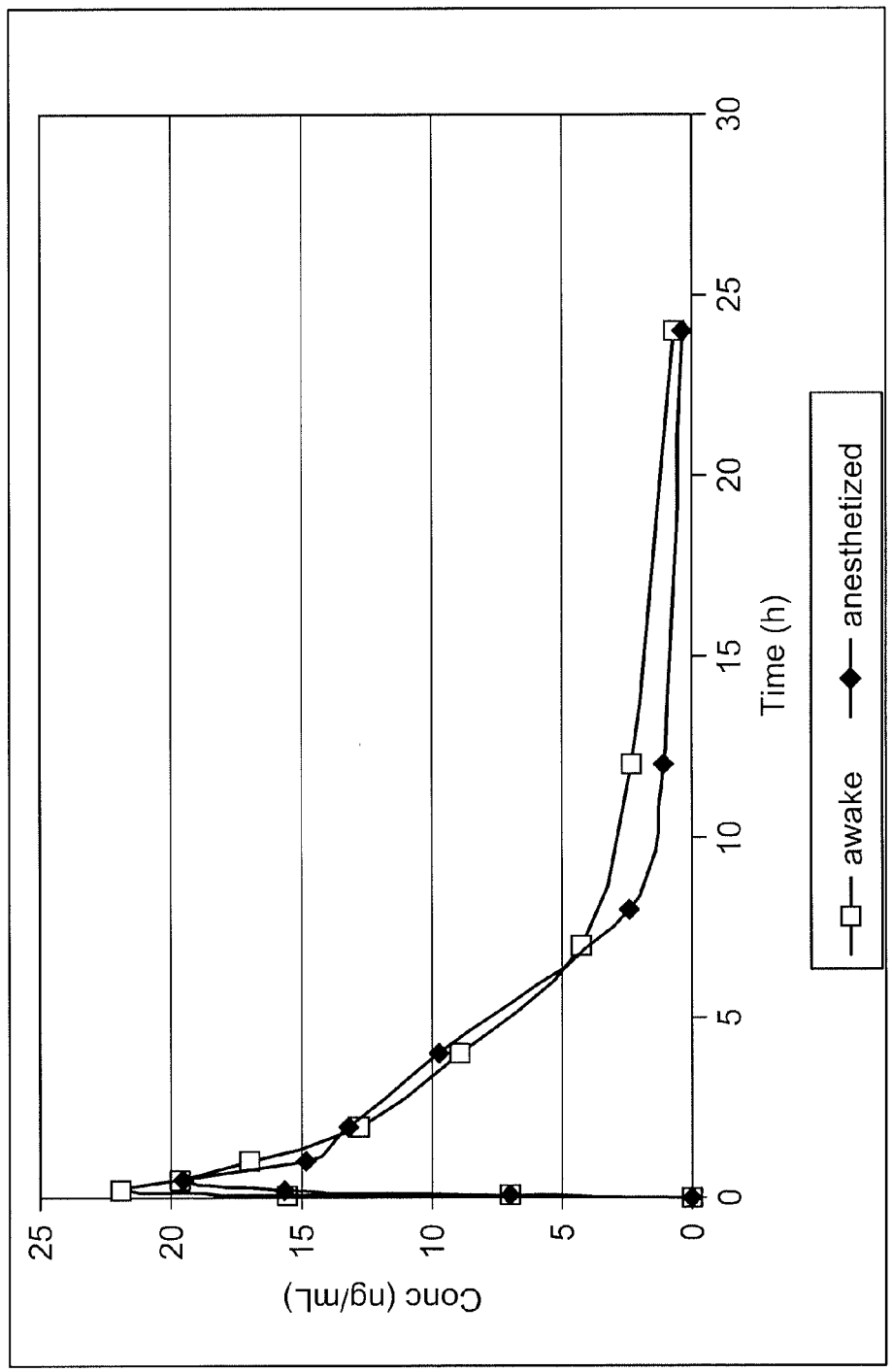
FIG. 17 shows blood plasma levels of clemastine fumarate administered via TMOM™ to awake and anesthetized dogs.

FIGS. 16 and 17 show that clemastine was readily absorbed by anesthetized canine subjects via the transmucosal route. The similarity in exposure with varying doses (i.e., awake is 1.0 mg/kg and anesthetized is 0.46 mg/kg) indicated that saturation (e.g., absorption, hepatic metabolism) may have occurred, possibly due to anesthetic effects.

Example 8

Transmucosal Oral Administration to Atopic Canine Subjects

Figure 18:
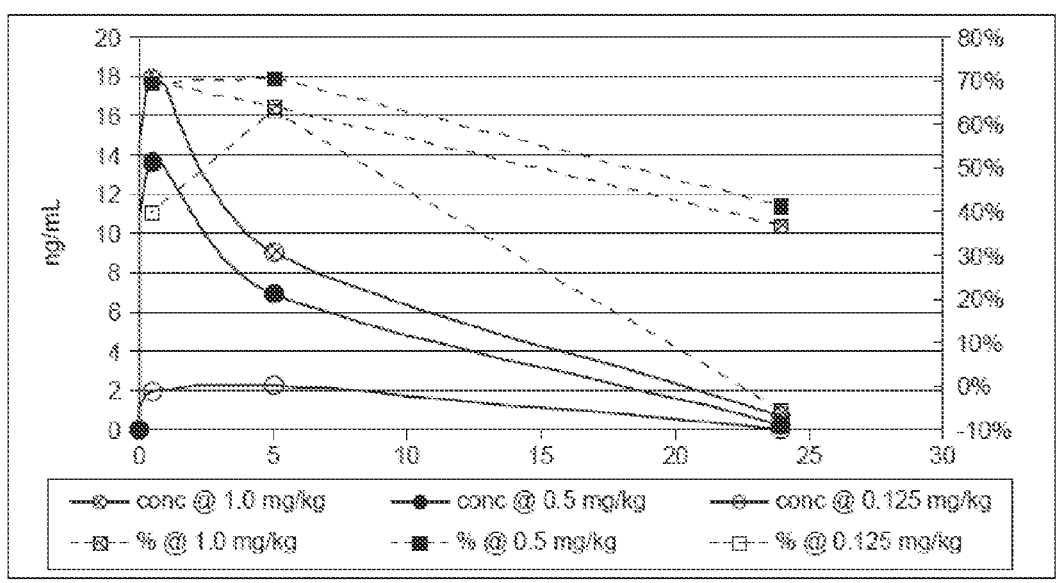
FIG. 18 shows a plot of PK/PD percent inhibition vs. IgE-IDT for atopic dogs, clemastine fumarate administered via TMOM™. Specifically.

The efficacy of clemastine administered by transmucosal oral administration was evaluated on a colony of spontaneous food allergic atopic canine subjects (Maltesexbeagle dogs). FIG. 18 shows the efficacy of clemastine delivered at several dosages (0.125, 0.5 and 1.0 mg/kg) via TMOM™ (16.67, 4.17 mg/mL clemastine fumarate, 75% ethanol and 25% water) against a cutaneous wheal and flare reaction caused by the release of histamine from mast cells. Transmucosal oral administration of clemastine provided approximately 40-70% inhibition of this reaction for up to 24 hours.

Example 9

Diphenhydramine Canine Study

Figure 19:
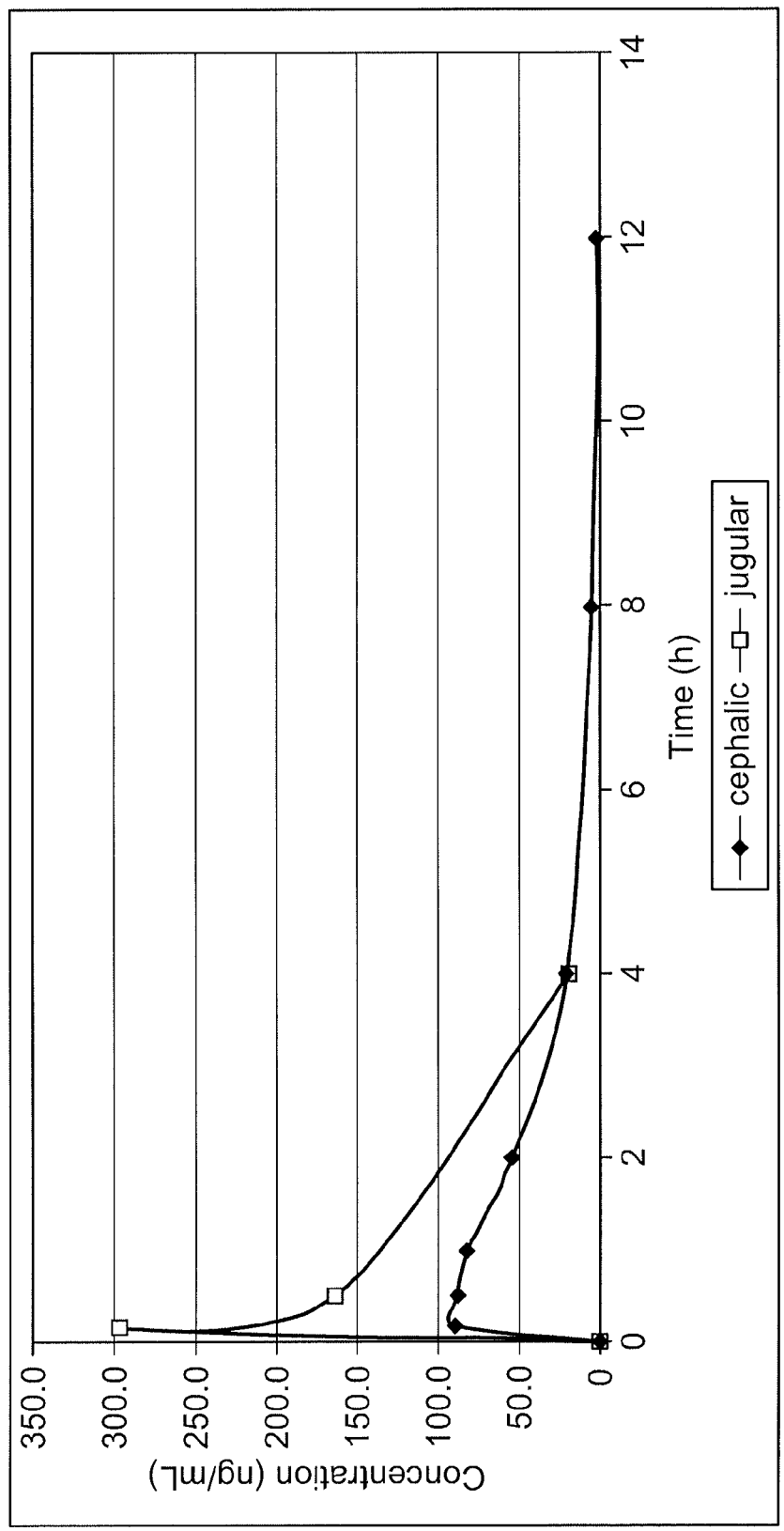
FIG. 19 compares cephalic and jugular blood plasma levels of diphenhydramine hydrochloride in dogs, administered via TMOM™.

A three dog study was carried out to evaluate TMOM™ administration of diphenhydramine, using a commercially-available injectable formulation (Benadryl, sterile, pyrogen-free solution containing 50 mg diphenhydramine hydrochloride/mL; dose-target 3 mg/kg; average dose 2.7 mg/kg (2.5-2.9 mg/kg); 400 µL volume). Blood samples were taken 10, 30 min, and 1, 2, 4, 8, and 12 hours post-dose, and the 10, 30 min and 4 h samples were taken from jugular and cephalic venipuncture. The results are shown in FIGS. 19 and 20. Significant concentrations of diphenhydramine were obtained, and the jugular/cephalic differential confirms diphenhydramine delivery via the transmucosal route.

Cardiovascular Agents

Compositions according to the invention are made in accordance with the teachings of one or more of U.S. Pat. Nos. 5,869,082, 5,955,098, 6,110,486, and 6,676,931, such that the compositions contains: from about 0.1 milligrams to about 25 milligrams of digoxin per kilogram of body weight, and at least one carrier. Such compositions can be therapeutically and/or prophylactically effective for treating abnormal/irregular heartbeat, weakness, shortness of breath, reduced exercise tolerance, lethargy, syncope, hypoxia, pulmonary edema, ascites, and/or loss of consciousness, or the like, in animals, e.g., dogs and cats. In most cases, the total administered dose of digoxin per animal is from about 4 milligrams to about 25 milligrams per kilogram of body weight per day.

Hormones

Compositions according to the invention are made in accordance with the teachings of one or more of U.S. Pat. Nos. 5,869,082, 5,955,098, 6,110,486, and 6,676,931, such that the compositions would contain: from about 0.01 milligrams to about 0.5 milligrams of levothyroxine sodium per kilogram of body weight, and at least one carrier, such that the composition is therapeutically and/or prophylactically effective for treating decreased or non-existent production of thyroid hormones such as thyroxine in animals.

The mean recommended dose rate of levothyroxine is about 0.2 mg/kg body weight, given once or twice per day for dogs, and from about 0.05 mg to about 0.2 mg per day for cats. The veterinarian typically adjusts the frequency of administration to the sufficiency of the blood levels of levothyroxine ($T_4$) after 4-12 weeks. As reduced or absent production of thyroid hormones is generally irreversible, treatment typically continues for the rest of the animal's life.

This composition is formed into a spray that is administered to dogs via the buccal mucosa, between the lips and teeth of each animal at an appropriate target dose.

In another example, compositions according to the invention are made in accordance with the teachings of one or more of U.S. Pat. Nos. 5,869,082, 5,955,098, 6,110,486, and 6,676,931, such that the compositions would contain: insulin (from naturally-derived porcine sources, from sources involving recombinant DNA techniques, or a combination thereof) and at least one carrier, such that the composition is therapeutically and/or prophylactically effective for treating decreased or non-existent production of insulin in animals.

This composition is formed into a spray that is administered to dogs via the buccal mucosa, between the lips and teeth of each animal at an appropriate target dose.

Immunosuppressive Agents

Compositions according to the invention are made in accordance with the teachings of one or more of U.S. Pat. Nos. 5,869,082, 5,955,098, 6,110,486, and 6,676,931, such that the compositions would contain: from about 0.1 milligrams to about 1 milligram of cyclosporine A per kilogram of body weight, and at least one carrier, such that the composition is therapeutically and/or prophylactically effective for treating enhanced or overactive immune response in animals.

The mean recommended dose rate of cyclosporine is about 5 mg/kg body weight per day given according to the following scheme. For atopic dermatitis, as an example, the compositions of the invention will initially be given daily until a satisfactory clinical improvement is seen. This will generally be the case after 4 to 8 weeks. Once the clinical signs of atopic dermatitis are satisfactorily controlled, the compositions of the invention can be given approximately every second day. If the signs are then controlled with this dosing, the compositions of the invention can be then given approximately every 3 to 4 days. The veterinary surgeon will adjust the frequency of administration to the response. Treatment may be stopped when the clinical signs are controlled. Upon recurrence of clinical signs, treatment should be resumed at daily dosing, and in certain cases repeated treatment courses may be required This composition is formed into a spray that is administered to dogs via the buccal mucosa, between the lips and teeth of each animal at an appropriate target dose. The methods and compositions may be used to systemically modulate the immune system, for instance during organ transplant such as a kidney transplant and/or may be used to treat atopic dermatitis, immune-mediated hemolytic anemia, discoid lupus erythematosus, keratoconjunctivitis sicca in animals such as a dog. The methods and compositions may also be used to treat German shepherd pannus.

Nutraceuticals, Vitamins, and/or Minerals

Compositions according to the invention are made in accordance with the teachings of one or more of U.S. Pat. Nos. 5,869,082, 5,955,098, 6,110,486, and 6,676,931, such that the compositions would contain: lysine or a pharmaceutically acceptable salt thereof; and at least one carrier, such that the composition is therapeutically and/or prophylactically effective for treating decreased or non-existent production or dietary intake of lysine in animals.

This composition is formed into a spray that is administered to dogs, horses, and/or cats via the buccal mucosa, between the lips and teeth of each animal at an appropriate target dose.

Sedative/Tranquilizer/Behavior Modifying Agents

Compositions according to the invention were made in accordance with the teachings of one or more of U.S. Pat. Nos. 5,869,082, 5,955,098, 6,110,486, and 6,676,931, such that the compositions contained: from about 0.05 milligrams to about 0.6 milligrams of zolpidem tartrate per kilogram of body weight, and at least one carrier. Such compositions can be therapeutically and/or prophylactically effective for treating insomnia, stress, separation anxiety, and/or hyperactivity, or the like, in animals, e.g., dogs and cats.

Example 10

Zolpidem

A six animal (canine and feline) two-way crossover experiment was carried out in which the subjects were administered a zolpidem tablet or a transmucosal oral mist of a 2.5% zolpidem tartrate solution.

Canine subjects were administered tablets (average dose 0.55 mg/kg (0.40-0.63 mg/kg)) or a transmucosal oral mist (average dose 0.55 mg/kg (0.42-0.62 mg/kg)). The transmucosal oral mist administration used a spray volume of 200-250 μL in 2-3 pumps of the spray dispenser. By comparison, the average human dose is 0.08-0.17 mg/kg Feline subjects were administered tablets (average dose 0.74 mg/kg) or a transmucosal oral mist (average dose 0.72 mg/kg). The transmucosal oral mist used a spray volume of 100 μL in 1 pump of the spray dispenser.

For both subjects, blood samples were taken 5, 15, 30 min, and 1, 2, 4 and 8 hours post-dose.

Figure 21:
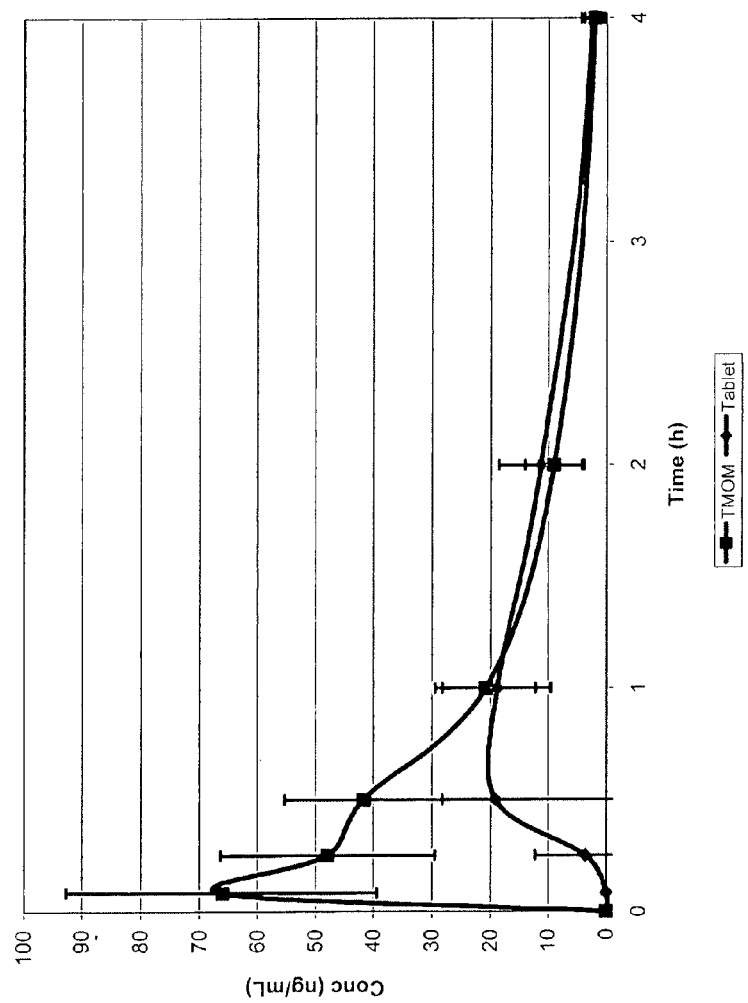
FIG. 21 shows the mean plasma concentrations of zolpidem tartrate when administered using two different dosage forms (TMOM™ and tablet) at the same dosage (~0.5 mg/kg) to dogs.
Figure 22:
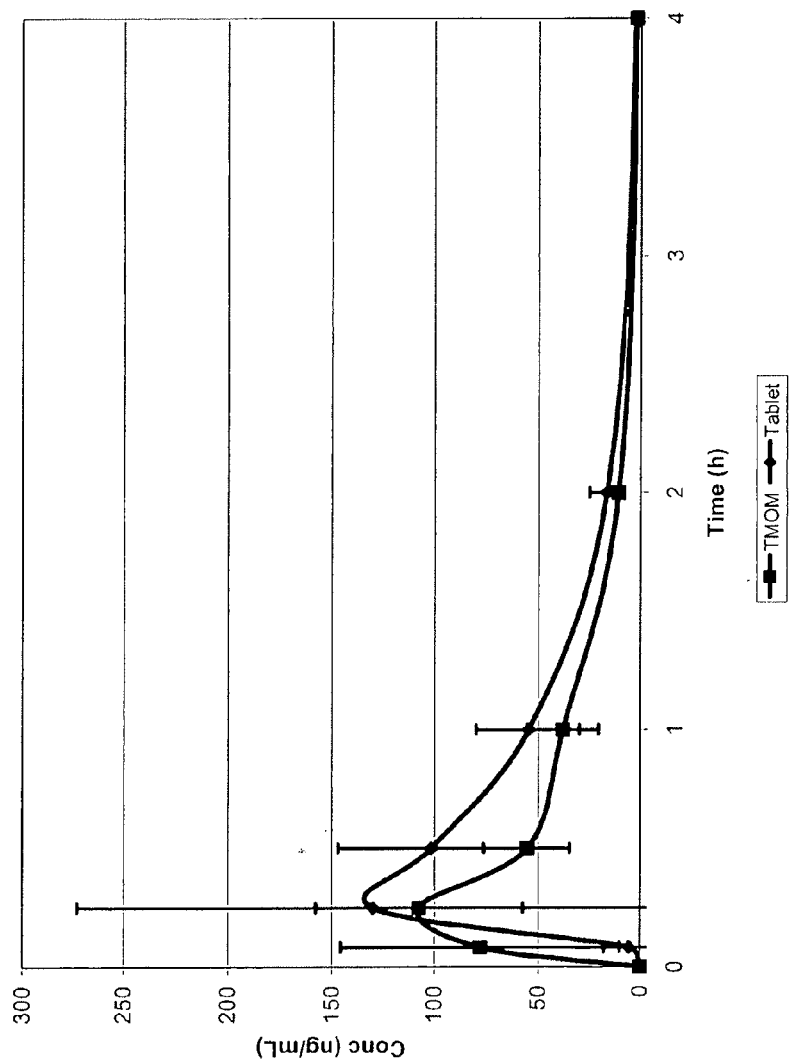
FIG. 22 shows the mean plasma concentrations of zolpidem tartrate when administered using two different dosage forms (TMOM™ and tablet) at the same dosage (~0.5 mg/kg) and both administered by the oral route to cats.

FIGS. 21 and 22 show the mean plasma concentrations over time of treatment of dogs and cats, respectively, with the sleeping aid agent compositions described above, in comparison to similar doses of orally administered tablet formulations. FIGS. 23 and 24 show comparisons of the pharmacokinetic parameters measured and/or calculated from that testing in dogs and cats, respectively. The secondary peak in FIG. 21 reflects oral-gastrointestinal absorption. However, even when some oral-gastrointestinal absorption occurs, transmucosal administration generally provides a more rapid rise in plasma levels compared to conventional oral administration methods. The data of FIG. 21 show that, following administration of the zolpidem tartrate using the TMOM™, the absorption time and absorption half-life are significantly lower (shorter), and the peak plasma concentration is higher, compared to the delivery profile seen with the tablet. The data of FIG. 22 show that, following administration of the zolpidem tartrate using TMOM™, the absorption time, peak plasma concentration, and total absorption are comparable (within experimental error) when compared to the delivery profile seen with the tablet.

FIG. 23 shows that transmucosal oral administration to canine subjects provides faster drug uptake (e.g., shorter $T_{max}$, greater $C_{max}$, and shorter absorption half-life) compared to conventional oral administration with a tablet. In addition, transmucosal oral administration provides good absorption of the zolpidem (e.g., greater AUC) compared to conventional oral methods.

FIGS. 23 and 24 show rapid drug uptake in dogs and cats using transmucosal oral administration, with good pharmacokinetic/pharmacodynamic agreement. However, salivation of the feline subjects can lead to reduced absorption (lower AUC) using transmucosal oral administration. Also, the AUC and $C_{max}$ values obtained by jugular sampling may be higher than values obtained by cephalic sampling (FIG. 24, only).

One of the canine subjects vomited 12 minutes after TMOM™ administration of zolpidem. Plasma levels of zolpidem in this animal remained consistent with the plasma levels of zolpidem observed for the remaining dogs in the study which had not vomited. This indicates that substantially all of the zolpidem dose was absorbed within 12 minutes of dosing. Furthermore, this demonstrates an advantage of transmucosal administration in animals over conventional oral dosage forms (i.e., tablets or oral suspension). Vomiting of the subject animal immediately after administration of a conventional oral dosage form would be expected to result in under-dosing of the animal (because the tablet or oral suspension would be eliminated from the animal's digestive tract before significant absorption of the active agent takes place). In contrast, the dose of active agent provided to the animal's blood stream by transmucosal administration appears relatively unaffected by vomiting. Thus, transmucosal administration provides a distinct advantage in veterinary medicine, where patients can resist or object to conventional oral dosage forms.

Example 11

Propofol

A six dog, two-way crossover experiment was carried out with a target dose of 6.0 mg/kg propofol administered by IV, and 30.0 mg/kg of propofol using transmucosal oral administration. The average IV dose (Propoflo™, 10 mg/mL) was 5.9 mg/kg (5.7-6.2 mg/kg), and the average transmucosal oral administration dose (propofol, 950 mg/mL) was 31.3 mg/kg (28.6-34.2 mg/kg; 350-550 μL using 4-6 pumps of the spray device). Blood samples were obtained at 0, 2, 5, 15, 30 minutes and 1, 2, 4 and 6 hours post dose.

Figure 25:
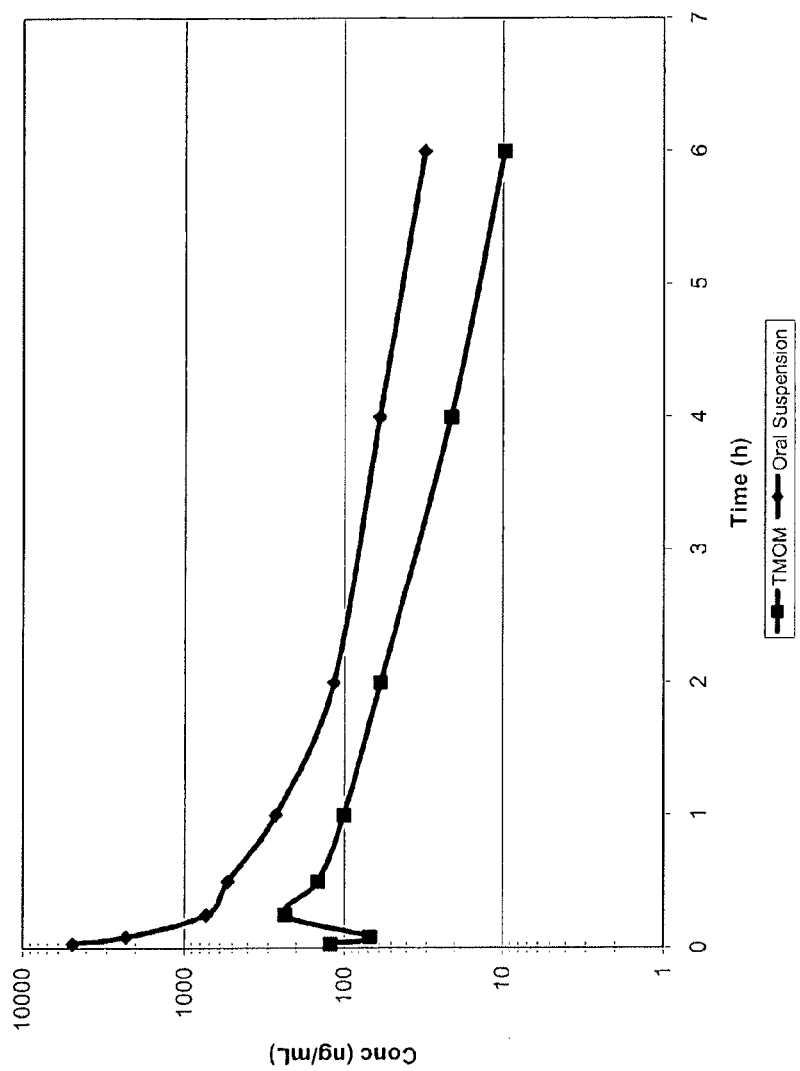
FIG. 25 shows mean plasma concentrations of propofol following intravenous administration at ~6.0 mg/kg and administration via TMOM™ at ~30.0 mg/kg.

Mean plasma concentrations of propofol are shown in FIG. 25, and pharmacokinetic parameters are provided in FIG. 26. Propofol uptake using transmucosal oral administration was rapid, although different from IV administration. Greater than 90% of the propofol administered transmucosally was absorbed by 2 hours. However, rapid distribution of the propofol provided a somewhat lower $C_{max}$ value compared to IV administration.

Antiparasitic Agents

Illustrative antiparasitic agent formulations are shown below

Nitenpyram

| Ingredient | Amount | Illustrative amount | Illustrative amount |
| --- | --- | --- | --- |
| nitenpyram | 0.1-25% | 0.5-15% | 0.6-10% |
| Ethanol | 40-99% | 60-97% | 70-97% |
| Water | 0.01-5% | 0.1-4% | 0.2-2% |
| Flavors | 0.05-10% | 0.1-5% | 0.1-2.5% |
| Propellant | 0-20% | 0-5% | 0-4% |

Ivermectin

| Ingredient | Amount | Illustrative amount | Illustrative amount |
| --- | --- | --- | --- |
| Ivermectin | 0.01-10% | 0.1-5% | 0.2-3% |
| Ethanol | 10-90% | 20-75% | 25-50% |
| Propylene glycol | 1-90% | 5-80% | 10-75% |
| Water | 0.01-5% | 0.14% | 0.2-2% |
| Flavors | 0.05-10% | 0.1-5% | 0.1-2.5% |
| Propellant | 0-10% | 0-5% | 0-4% |

Biological Data

Concentration of the active ingredient in the formulation will vary to accomplish the desired dose levels across a wide weight-range of target animal patients. For example, a 120 pound dog administered 1 to 3 sprays of the transmucosal oral mist will be greater than the concentration necessary to treat a 12 pound dog with 1 to 3 sprays. The number of sprays per application will vary for the same reason.

The active ingredient can vary depending upon the spectrum of parasite targeted in any one product. With thousands of parasites infect target animal species, the active ingredient(s) may vary to accomplish the desired medical outcome.

The oral mucosal surface area treated may vary and include any surface in the oral cavity, including buccal, gingival, lingal, or sublingual surfaces.

Example 12

Milbemycin Canine Study

A twelve dog random parallel design was carried out to compare conventional oral administration (i.e., tablets) of Milbemycin with transmucosal oral administration. The tablets used were Interceptor® Flavor Tab®, 5.75 mg and 11.5 mg, providing an average dose of 0.78 mg/kg (0.50-0.99 mg/kg). The formulation for transmucosal oral administration (14.3 mg/mL milbemycin (4.9%), 31.9% DMSO, 14.7% ethanol, 4.9% benzyl alcohol, 2.45% Tween-20, 2.45 mg/mL BAC, 2.45 mg/mL liver extract, 1.96% cod liver oil ester, 17.2% propylene glycol and 22.1% water) provided an average dose (based on post-dose analysis) of 0.28 mg/kg (0.24-0.34 mg/kg; 200-300 μL spray volume using 2-3 pumps of the spray device). Blood samples were obtained at 0, 5, 15, 30 minutes and 1, 2, 4 and 8 hours post dose.

Figure 27:
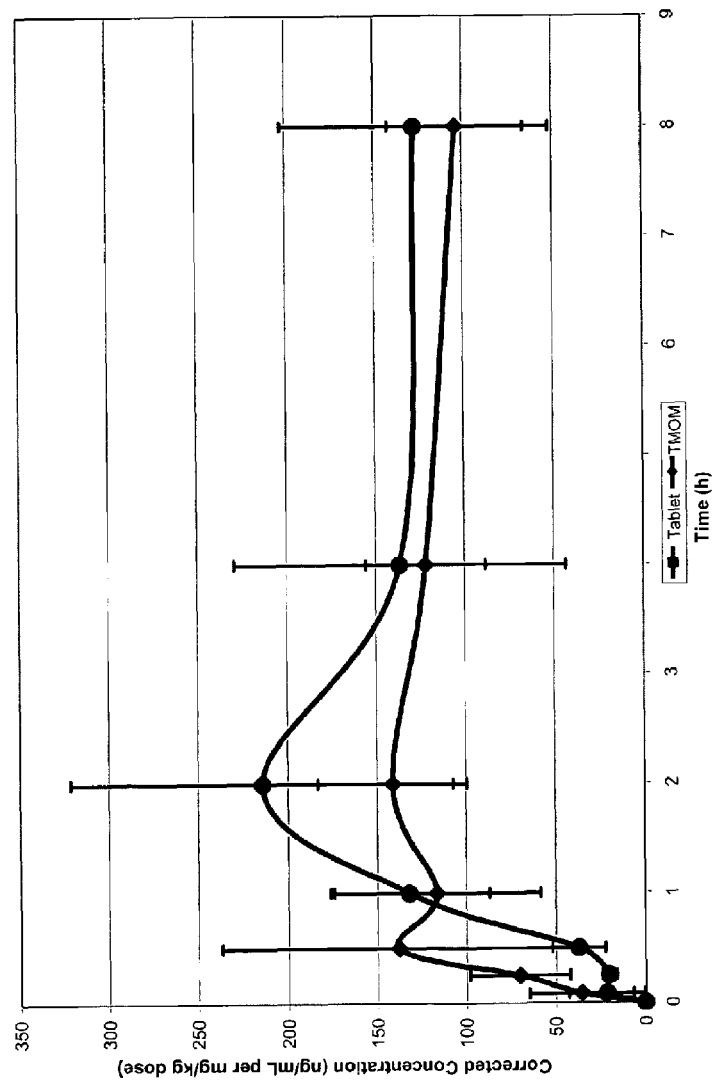
FIG. 27 shows mean blood plasma levels of milbemycin in dogs, administered via TMOM™ and oral chewable tablet. Specifically.

The results of this study are shown in FIGS. 27 and 28. Milbemycin uptake by transmucosal oral administration was very good. The bioavailability by transmucosal oral administration and using the conventional tablet was similar, but the transmucosal administration showed less variable plasma concentrations.

Antibiotics

Example 13

Enrofloxacin Feline Study

Figure 29:
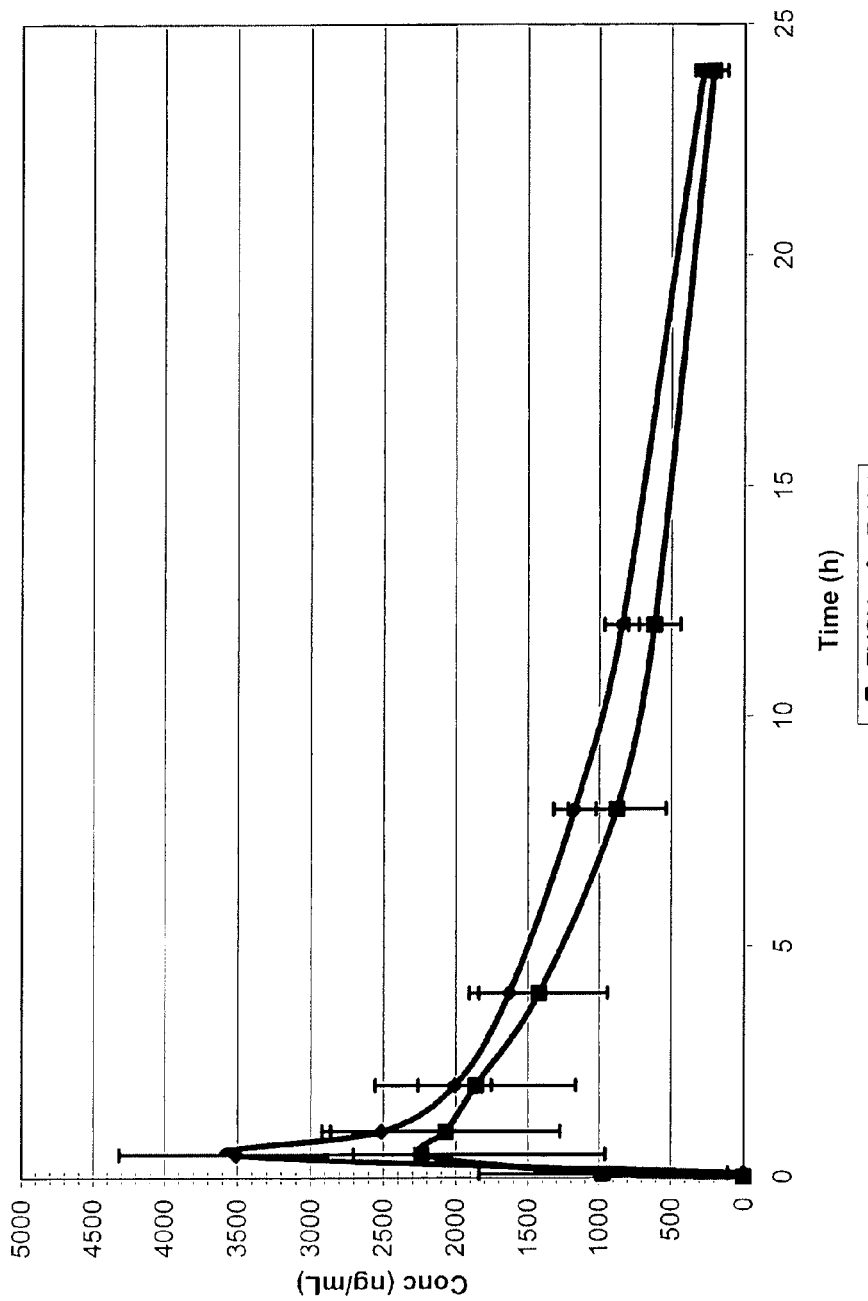
FIG. 29 shows mean plasma concentrations curves for enrofloxacin in felines, administered via tablets and TMOM™.

A six cat, two-way crossover study was carried out to compare conventional oral administration (i.e., tablets, Baytril®) with transmucosal oral administration (Baytril® 100; 100 mg of enrofloxacin, L-arginine base 200 mg, n-butyl alcohol 30 mg, benzyl alcohol (as a preservative) 20 mg, and water for injection, q.s.). The target was 5 mg/kg enrofloxacin. The average tablet dose was 4.7 mg/kg and the average TMOM™ dose was 4.9 mg/kg (250-300 μL). Blood samples were obtained at 5, 30 minutes and 1, 2, 4, 8, 12 and 24 hours post dose. The results are shown in FIGS. 29-31, which show that transmucosal administration provides enrofloxacin profiles similar to those provided by conventional administration, with essentially no difference in AUC, $C_{max}$, $T_{max}$ or $t_{1/2}$ values. In addition, no lag time was observed in enrofloxacin uptake with TMOM™, and significant 5 minute plasma concentrations were achieved. Consistently and significantly higher jugular plasma concentrations as compared to cephalic concentrations measured at the 5 min time point confirm the transmucosal route of delivery for enrofloxacin.

Example 14

Acceptability Studies

The acceptability of transmucosal oral administration and various transmucosal oral administration formulations was evaluated on animal subjects. The results are shown in FIGS. 32-44. Overall, transmucosal oral administration appears to be readily tolerated by most subjects (see FIG. 44).

Figure 32:
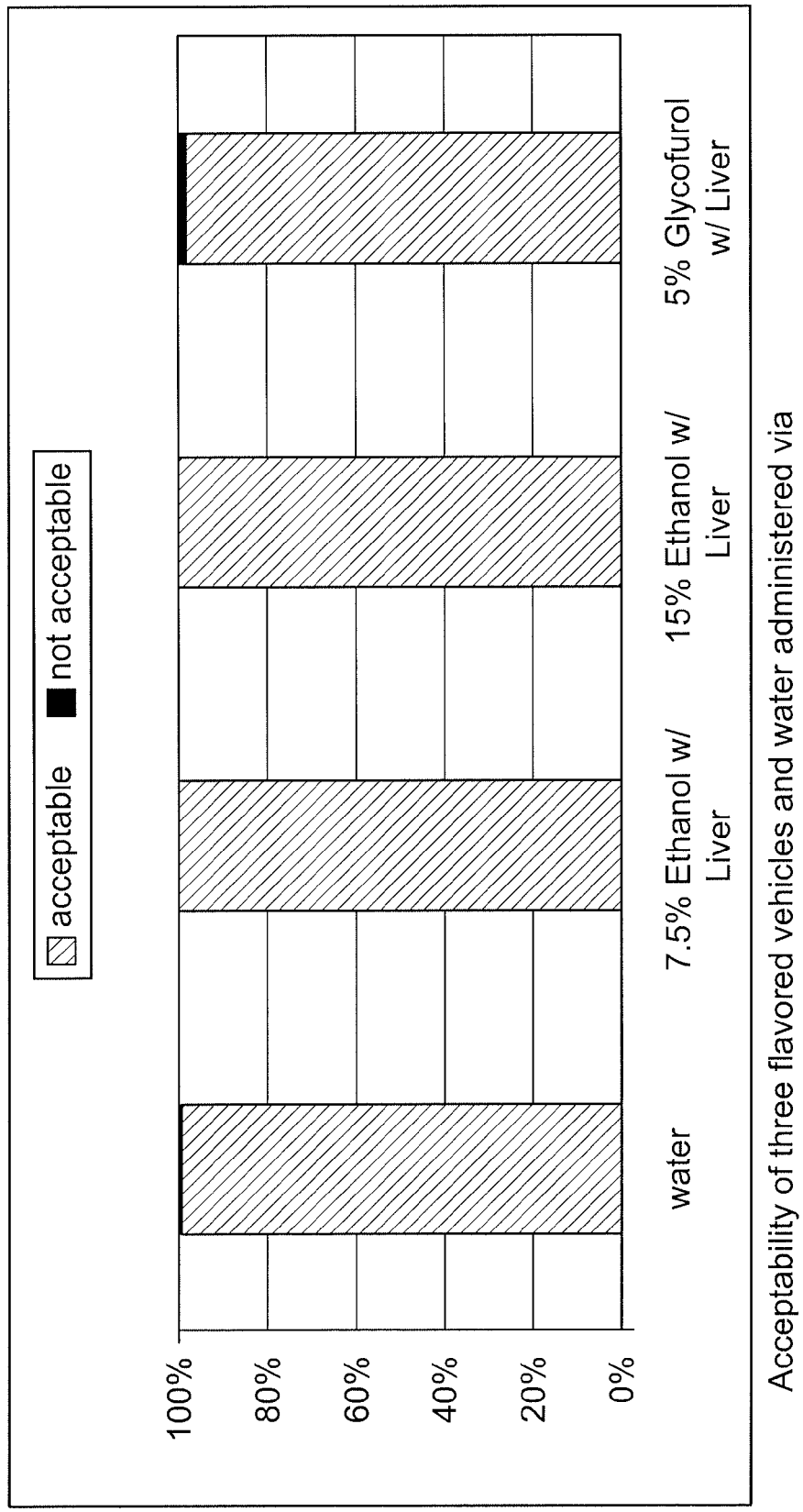
FIG. 32 is a chart of canine acceptance of TMOM™ administration of various vehicles.
Figure 33:
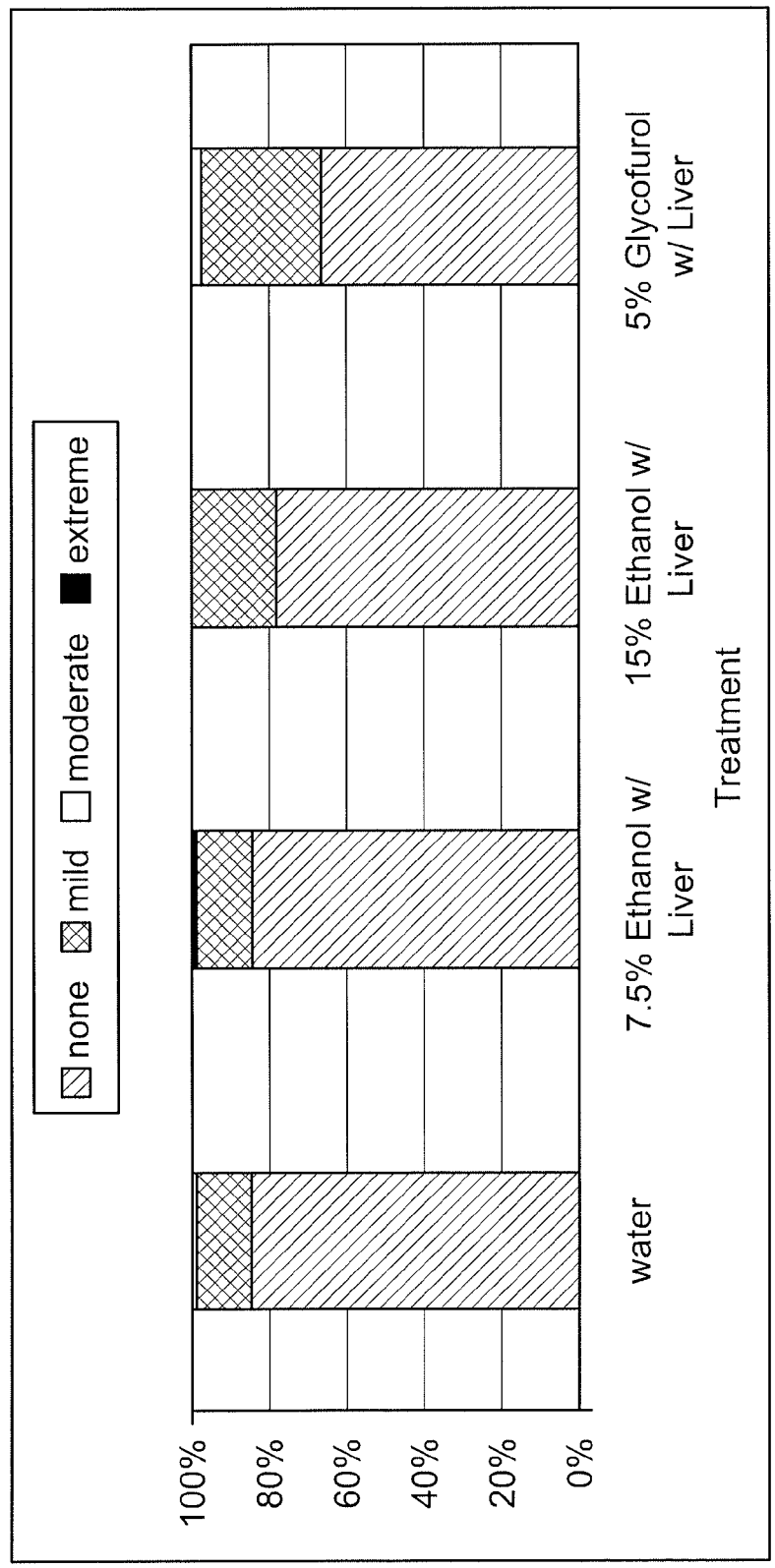
FIG. 33 is a chart of the severity of reactions of canines to TMOM™ administration of various vehicles.

FIGS. 32 and 33 show the acceptance and severity of reaction by canine subjects of various vehicles, administered by TMOM™. All of the vehicles tested were acceptable to most subjects, although formulations containing glycofurol were found to be slightly less acceptable.

Figure 34:
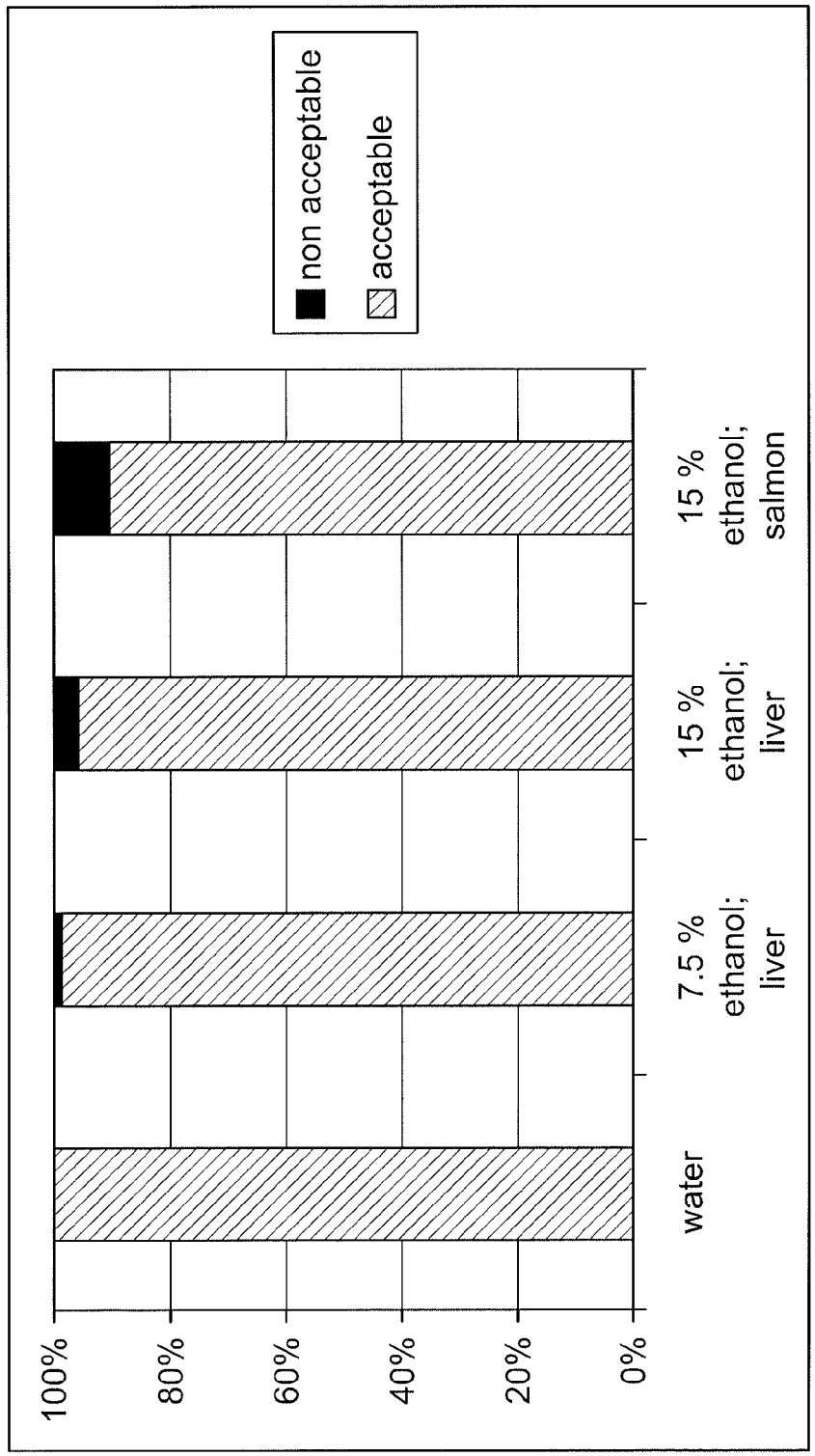
FIG. 34 is a chart of feline acceptance of TMOM™ administration of various vehicles.
Figure 35:
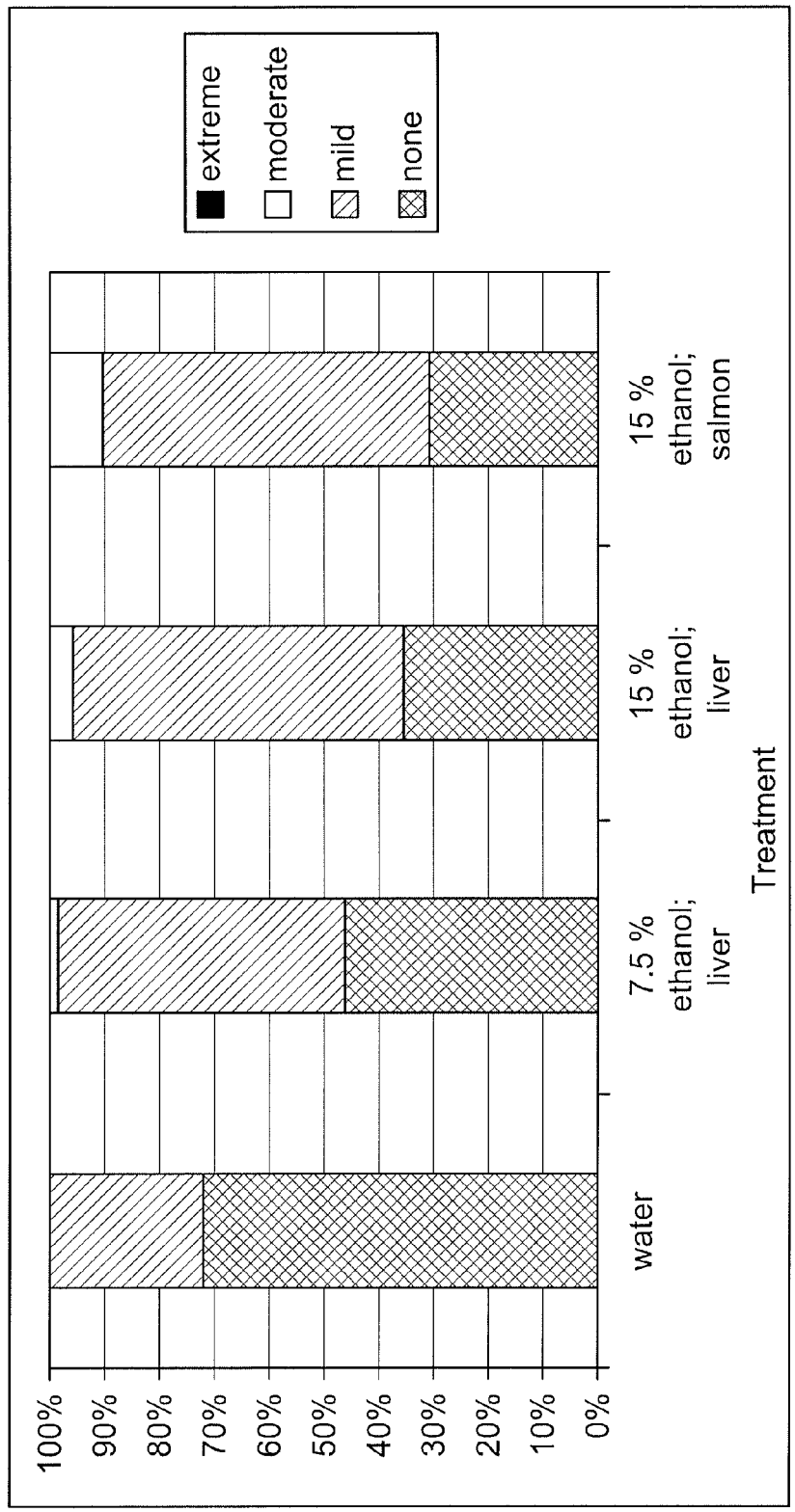
FIG. 35 is a chart of the severity of reactions of felines to TMOM™ administration of various vehicles.
Figure 36:
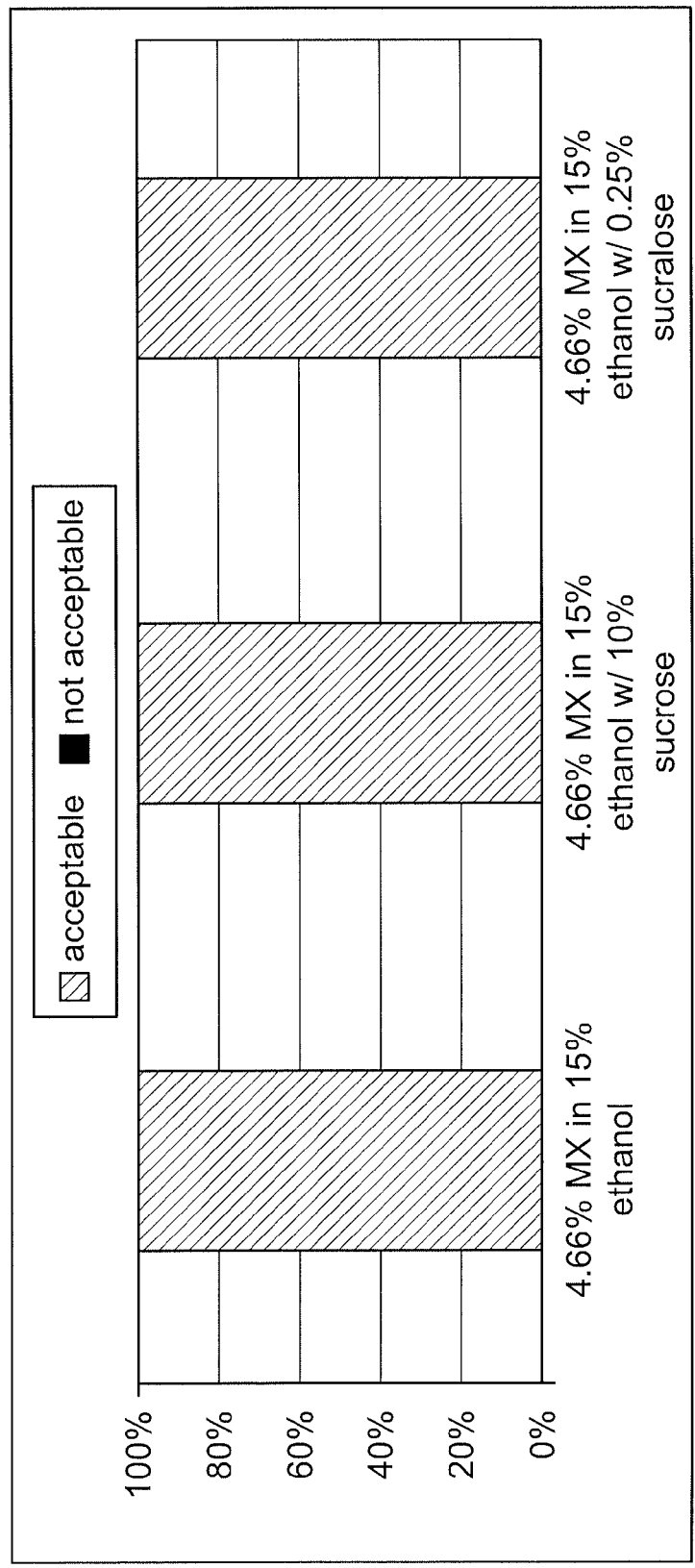
FIG. 36 is a chart of canine acceptance of TMOM™ administration of various meloxicam formulations.
Figure 37:
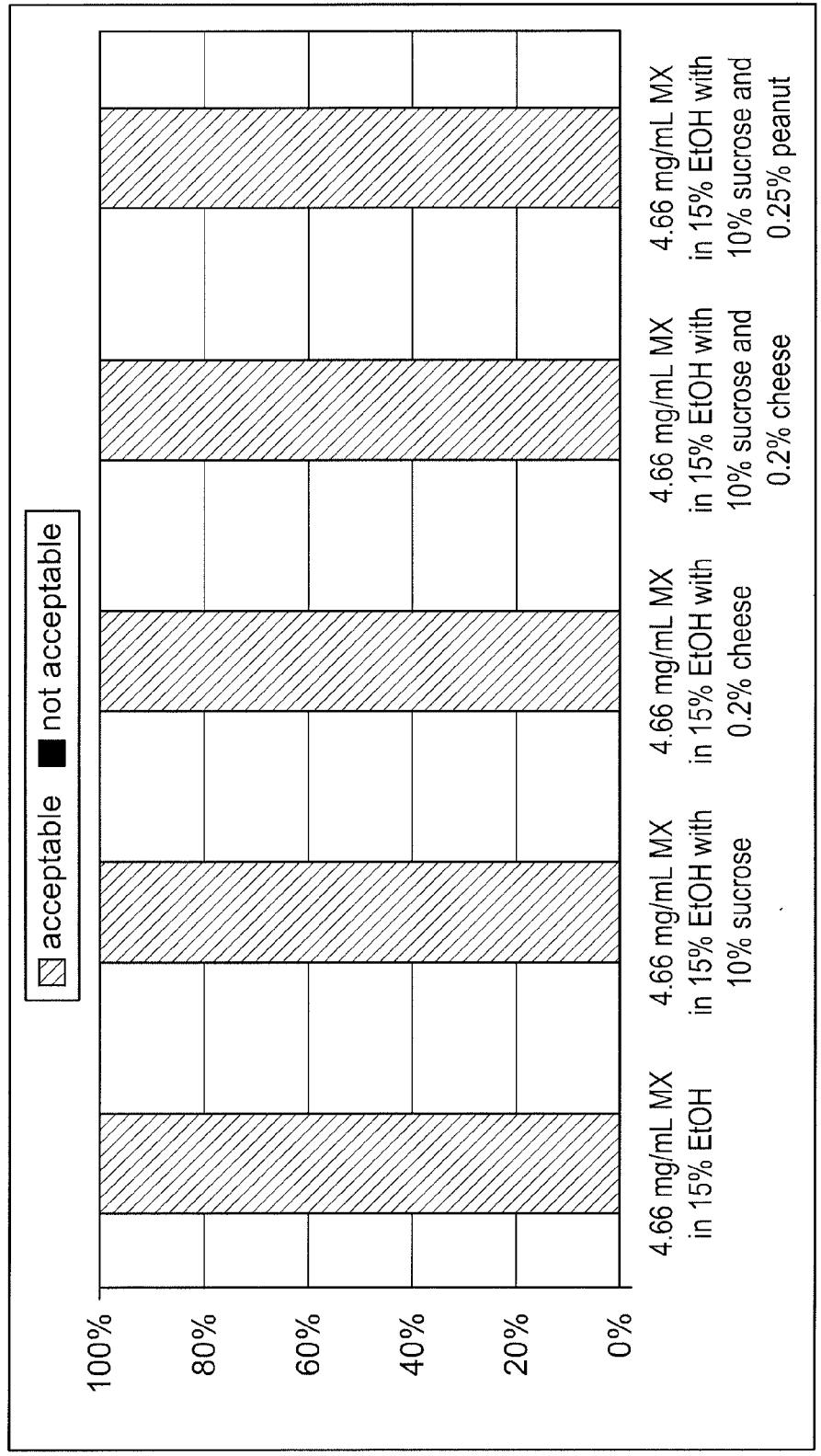
FIG. 37 is a chart of canine acceptance of TMOM™ administration of various meloxicam formulations.
Figure 38:
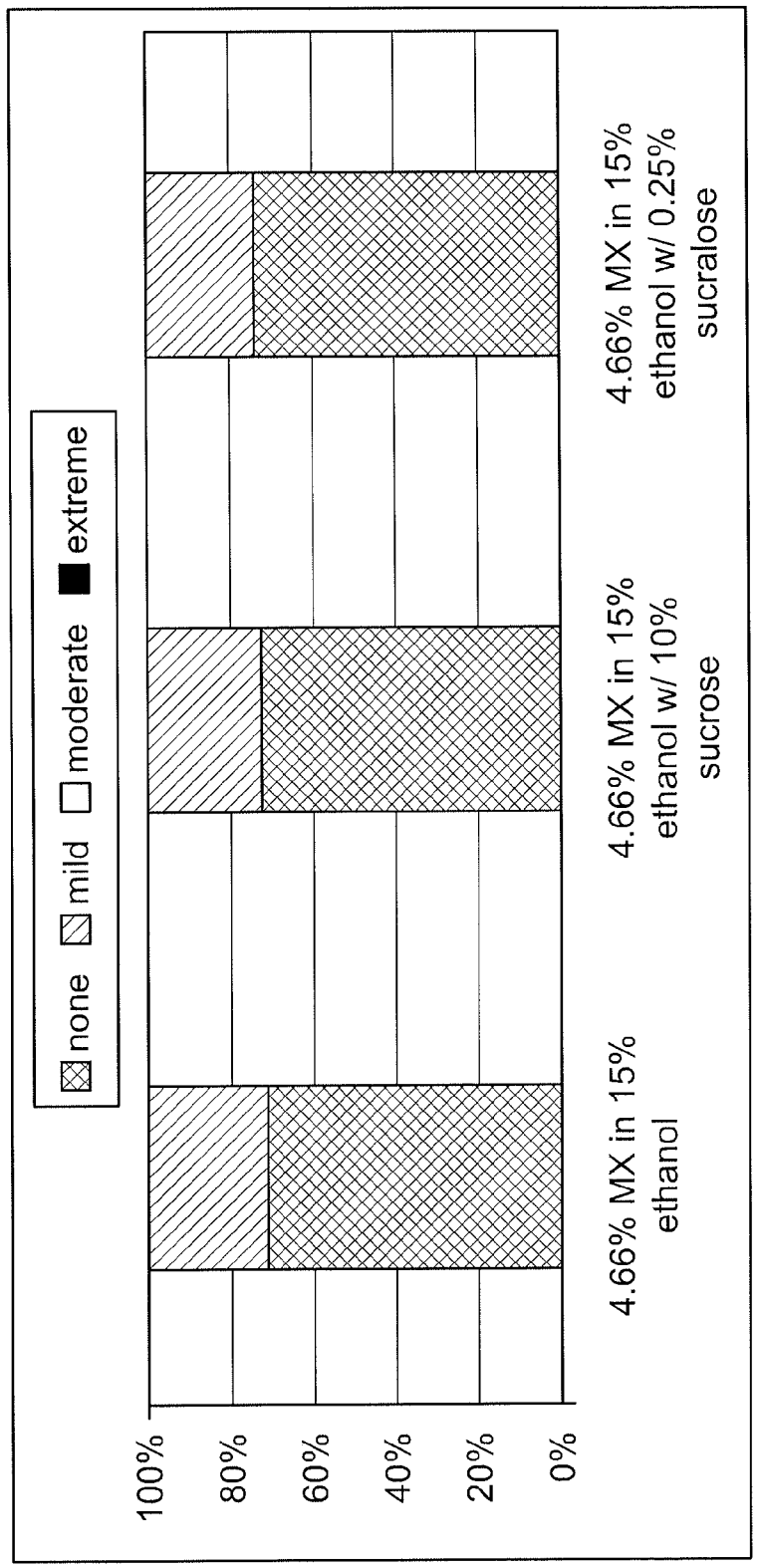
FIG. 38 is a chart of the severity of reaction of canines to TMOM™ administration of various meloxicam formulations.
Figure 39:
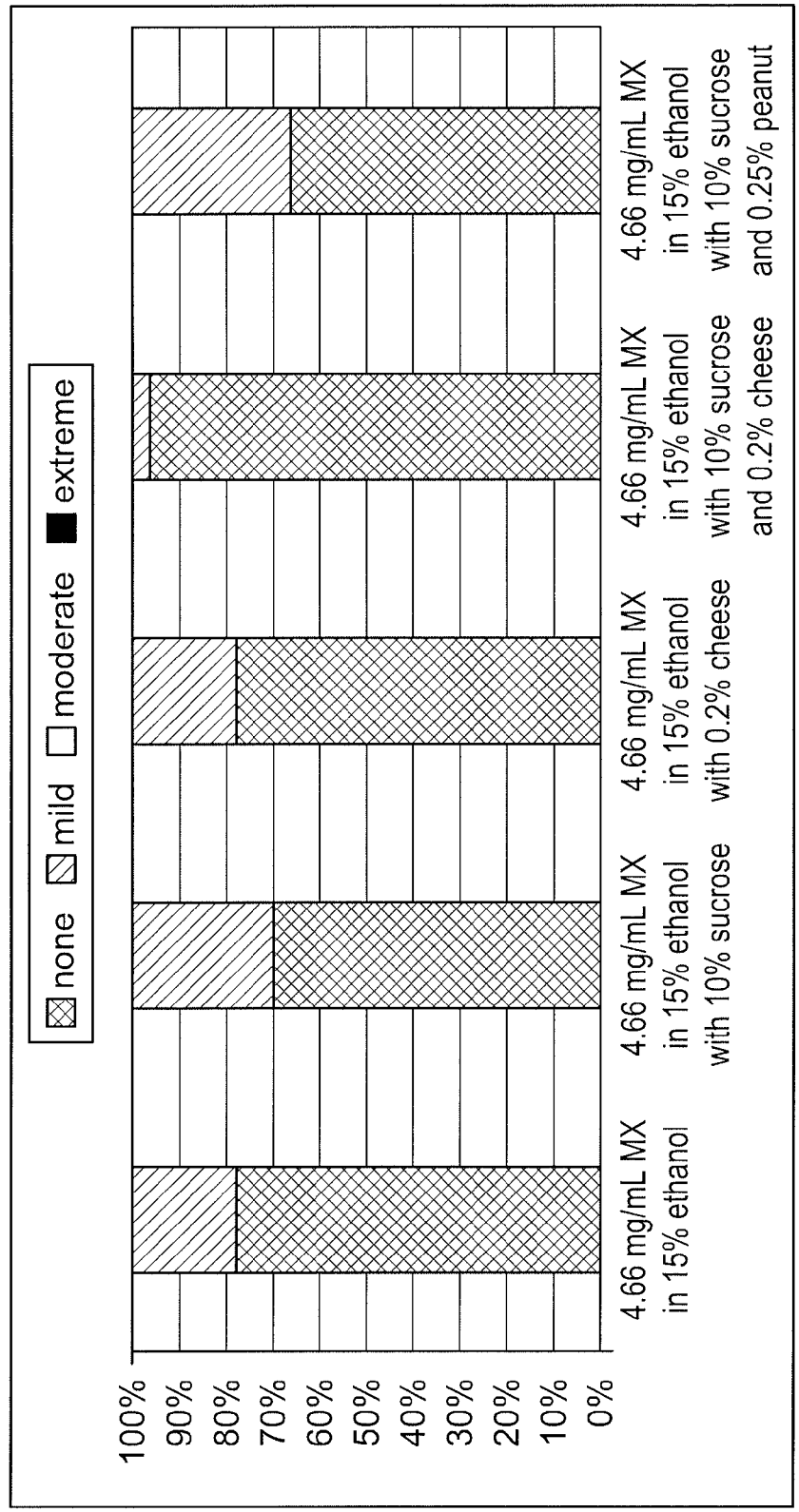
FIG. 39 is a chart of the severity of reaction of canines to TMOM™ administration of various meloxicam formulations.
Figure 40:
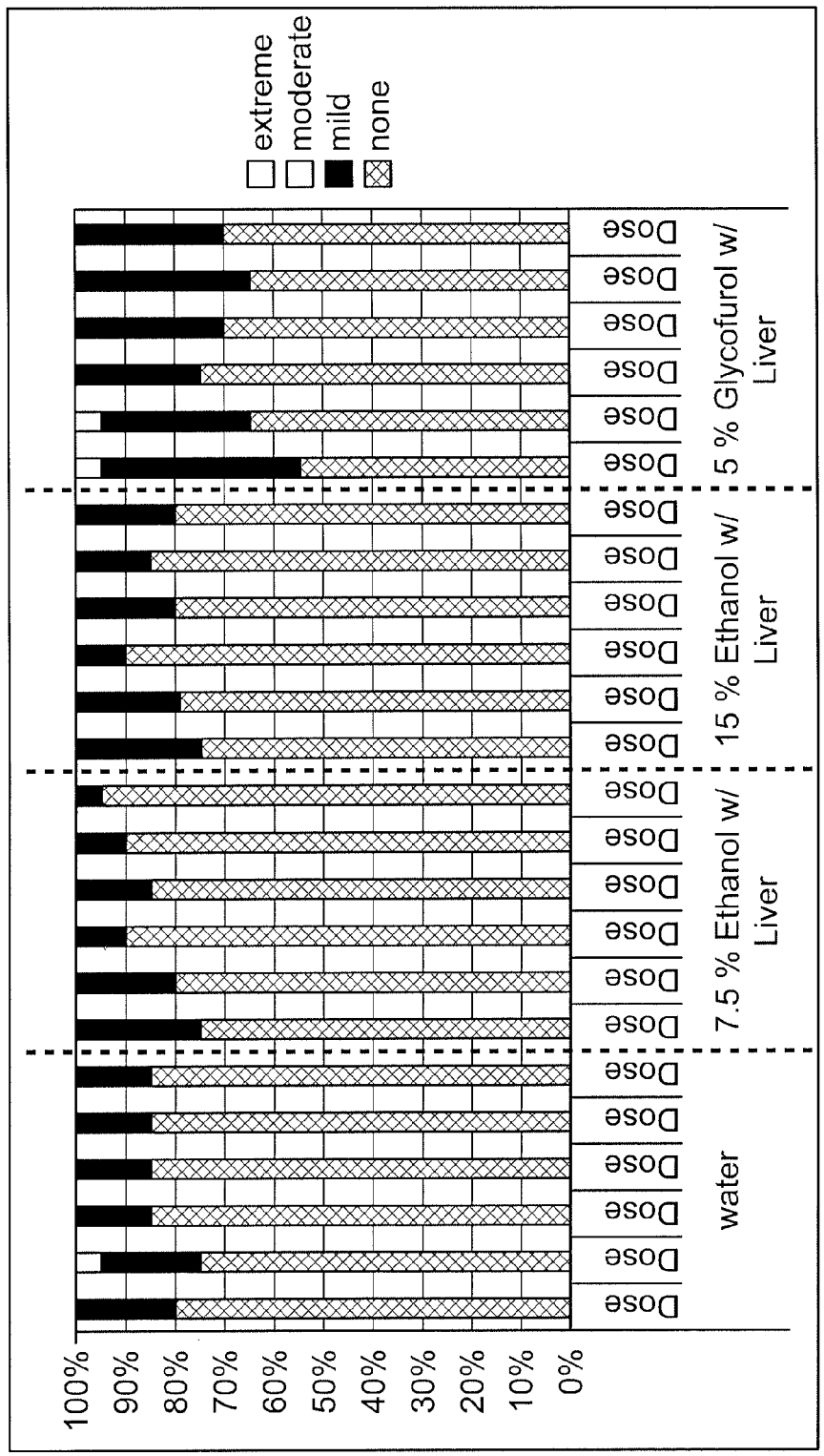
FIG. 40 is a chart of the severity of reaction of felines to TMOM™ administration of various vehicles, by number of doses and formulation.
Figure 41:
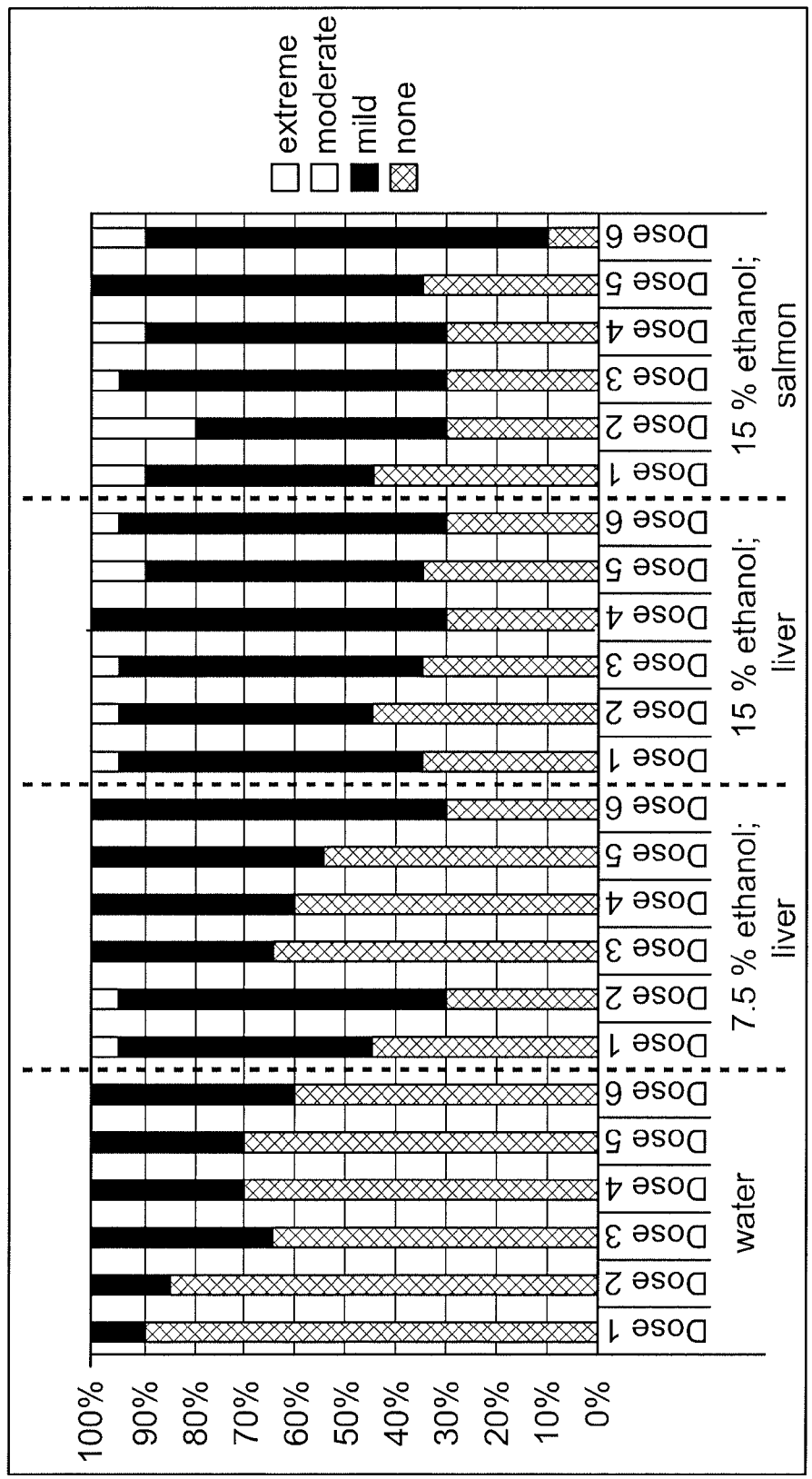
FIG. 41 is a chart of the severity of reaction of felines to TMOM™ administration of various vehicles, by number of doses and formulation.
Figure 42:
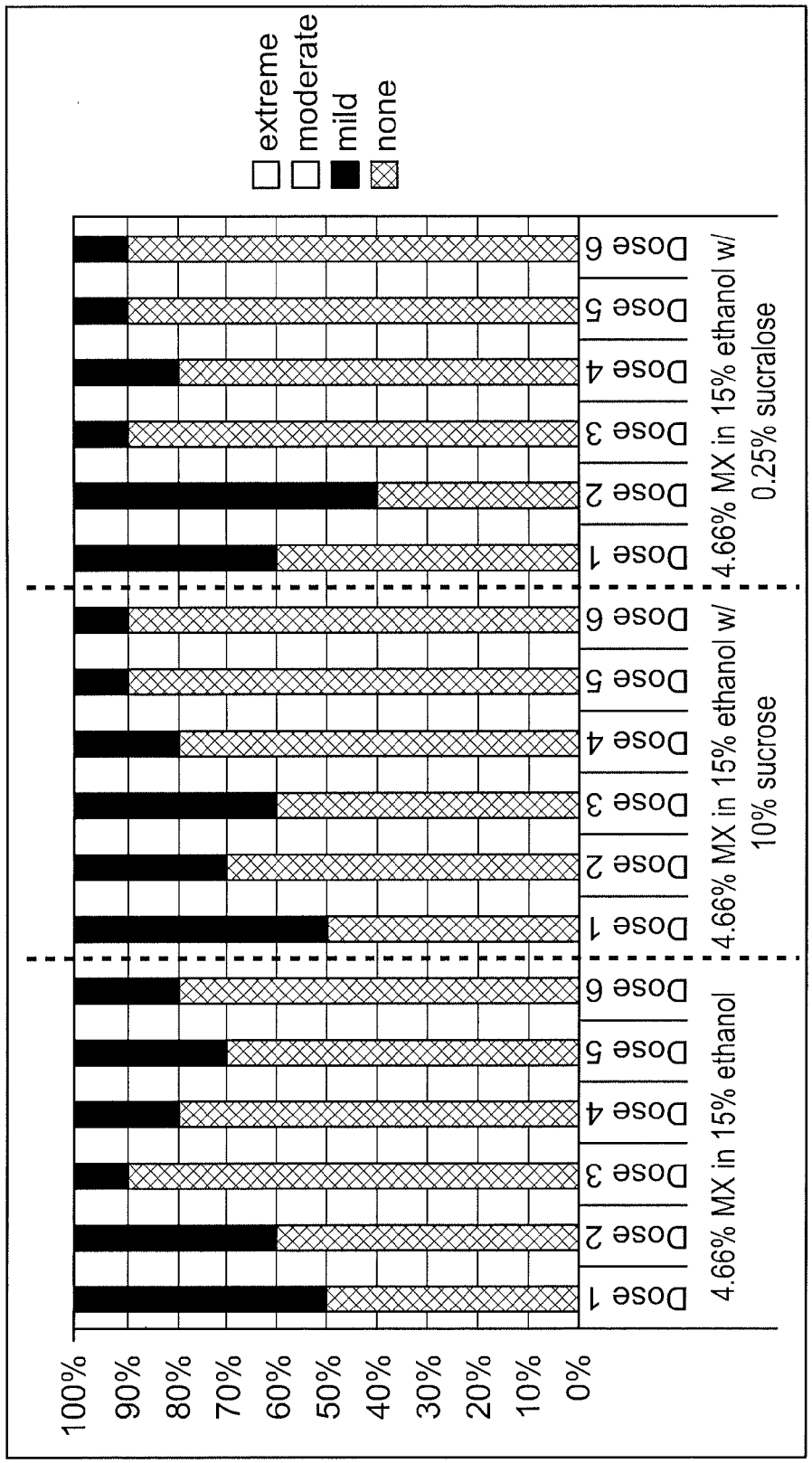
FIG. 42 is a chart of the severity of reaction of canines to TMOM™ administration of various meloxicam formulations, by number of doses and formulation.
Figure 43:
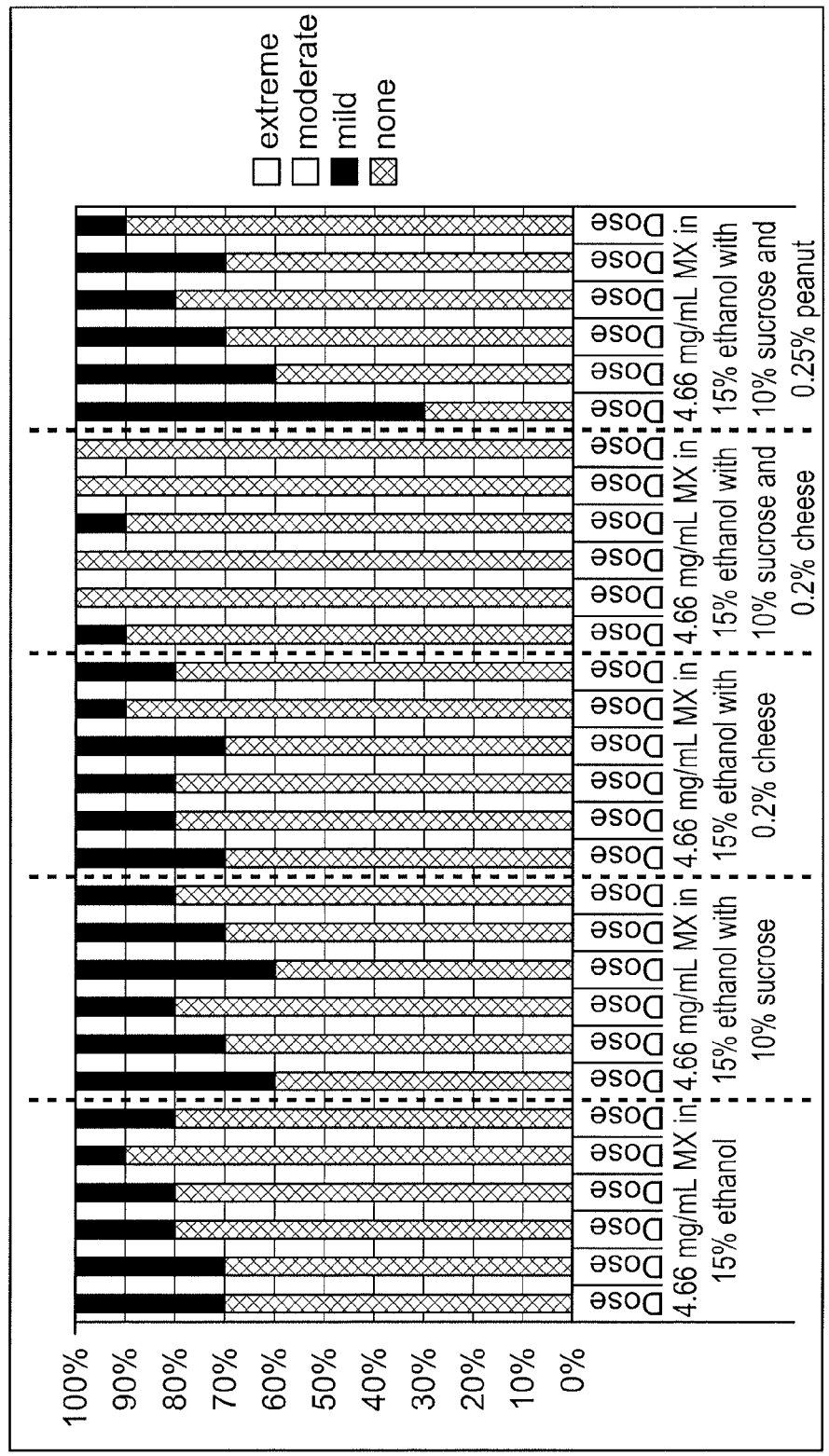
FIG. 43 is a chart of the severity of reaction of canines to TMOM™ administration of various meloxicam formulations, by number of doses and formulation.

FIGS. 34 and 35 show the acceptance and severity of reaction by feline subjects of various vehicles, administered by TMOM™. The formulation containing salmon flavoring was found to be somewhat less acceptable than other formulations containing other flavoring agents, or no flavoring agent.

FIGS. 36-39 show that various meloxicam formulations were readily accepted by canine subjects.

FIGS. 40-43 show the acceptance and severity of reaction of canine and feline subjects to various vehicles and over a number of doses to TMOM™ administration.

FIG. 44 shows the percent successful dose administrations using TMOM™ administration on canine and feline subjects. TMOM™ administration was nearly 99% successful, and more than 99% of the administrations required no assistance. Thus, transmucosal administration is a simple and highly effective method for administering active agents to animals.

Example 15

Multiple Doses by TMOM™ Administration

Figure 45:
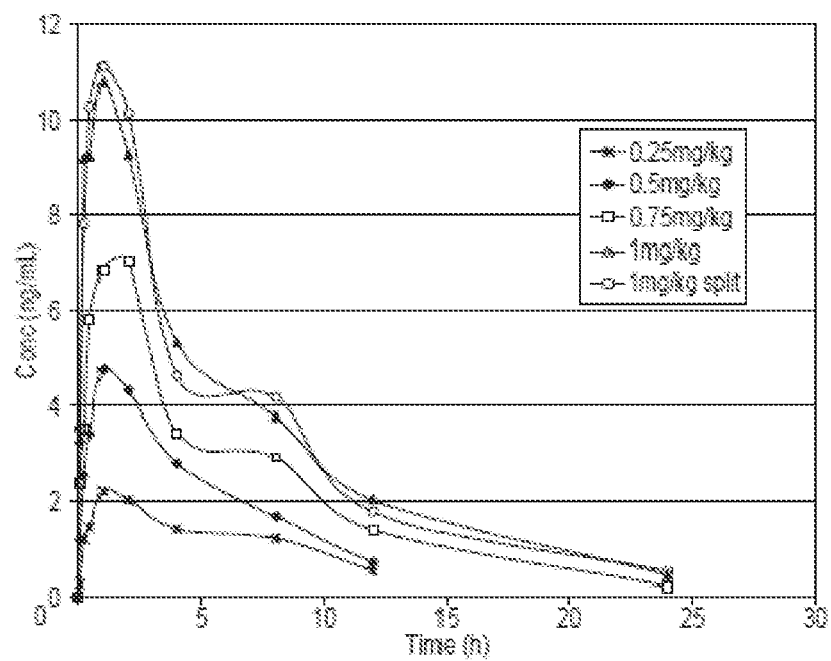
FIG. 45 is a plot showing the mean plasma concentration of clemastine in dogs administered increasing dosages from 0.25 to 1 mg/kg via TMOM™ administrations. Specifically.

Dogs were administered different clemastine doses using multiple TMOM™ administrations. FIG. 45 shows that increasing TMOM™ dose volume (by increased number of sprays) of a formulation containing 13 mg/mL clemastine fumarate provided increasing plasma concentrations. Multiple doses administered to one part of the both, or split between both sides of the mouth gave similar results.

What is claimed is:

1. A spray container comprising:
   a composition comprising meloxicam, or a pharmaceutically acceptable salt thereof, dissolved in an aqueous ethanol solution;
   sodium hydroxide wherein the sodium hydroxide is necessary for dissolving the meloxicam; and
   a metered valve.

2. The spray container of claim 1, wherein the spray container is an aerosol spray container.

3. The spray container of claim 1, wherein the spray container is a pump spray container.

4. The spray container of claim 3 wherein the composition is propellant-free.

5. The spray container of claim 1 wherein the composition comprises a bioadhesive agent.

6. The spray container of claim 1 wherein the composition comprises boric acid.

7. The spray container of claim 1 wherein the composition comprises hydrochloric acid and has a pH greater than 7.2.

8. The spray container of claim 1 wherein the spray container delivers a transmucosal mist of a pharmaceutically effective amount of the meloxicam or pharmaceutically acceptable salt thereof to the oral mucosa of a non-human animal.

9. The spray container of claim 8 wherein the spray container delivers the composition in a dose from about 0.05 mg to about 5 mg per kilogram body weight.

10. The spray container of claim 1 comprising from 7.5 wt % to 15 wt % ethanol based on the total weight of the composition.

11. The spray container of claim 8, wherein the oral mucosa of a non-human animal comprises one or more oral mucosa selected from the group consisting of buccal mucosa, gingival mucosa, lingual mucosa, palatal mucosa, pharyngeal mucosa, and sublingual mucosa.

12. The spray container of claim 11, wherein the oral mucosa comprises the buccal mucosa.

13. The spray container of claim 1, wherein the concentration of meloxicam in the composition is from about 0.01 percent by weight to about 10 percent by weight of the composition.

14. The spray container of claim 1, wherein the concentration of aqueous ethanol in the composition is from about 15 percent by weight to about 99.999 percent by weight of the total composition.

15. The spray container of claim 1, wherein the concentration of meloxicam in the composition is from about 0.01 percent by weight to about 10 percent by weight of the composition and the concentration of aqueous ethanol in the composition is from about 15 percent by weight to about 99.999 percent by weight of the total composition.

16. The spray container of claim 8, wherein the non-human animal is selected from the group consisting of dog, cat, horse, cow, pig, sheep, and poultry.

17. The spray container of claim 1, wherein the composition further comprises at least one therapeutic agent in addition to meloxicam.

18. The spray container of claim 1, wherein the composition is suitable for administration to an anesthetized non-human animal.

* * * * *